US010981957B2

(12) United States Patent
Benjdia et al.

(10) Patent No.: US 10,981,957 B2
(45) Date of Patent: Apr. 20, 2021

(54) PEPTIDES HAVING ANTIMICROBIAL ACTIVITY AND NEW ENZYME CAPABLE OF CONVERTING L-CONFIGURED RESIDUE IN D-CONFIGURED AMINO ACID IN A PEPTIDE

(71) Applicant: INSTITUT NATIONAL DE RECHERCHE POUR L'AGRICULTURE, L'ALIMENTATION ET L'ENVIRONNEMENT, Paris (FR)

(72) Inventors: Alhosna Benjdia, Limeil Brevannes (FR); Alain Guillot, Forges les Bains (FR); Olivier Berteau, Jouy en Josas (FR)

(73) Assignee: INSTITUT NATIONAL DE RECHERCHE POUR L'AGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 0 days.

(21) Appl. No.: 15/781,153

(22) PCT Filed: Dec. 1, 2016

(86) PCT No.: PCT/EP2016/079362
§ 371 (c)(1),
(2) Date: Jun. 4, 2018

(87) PCT Pub. No.: WO2017/093366
PCT Pub. Date: Jun. 8, 2017

(65) Prior Publication Data
US 2018/0346526 A1    Dec. 6, 2018

(30) Foreign Application Priority Data

Dec. 2, 2015  (EP) .................................... 15306909
Aug. 12, 2016 (EP) .................................... 16183955

(51) Int. Cl.
A61K 38/10    (2006.01)
A61K 38/16    (2006.01)
A01N 37/18    (2006.01)
A61K 38/00    (2006.01)
A61P 31/04    (2006.01)
C07K 5/00     (2006.01)
C07K 7/00     (2006.01)
C07K 16/00    (2006.01)
C07K 17/00    (2006.01)
A61K 38/04    (2006.01)
C07K 14/32    (2006.01)
C12N 9/90     (2006.01)
C07K 7/08     (2006.01)

(52) U.S. Cl.
CPC .............. *C07K 14/32* (2013.01); *A61K 38/10* (2013.01); *A61K 38/164* (2013.01); *A61P 31/04* (2018.01); *C07K 7/08* (2013.01); *C12N 9/90* (2013.01)

(58) Field of Classification Search
None
See application file for complete search history.

(56) References Cited

PUBLICATIONS

Morinaka et al., Angew. Chem. Int. Ed. 53:8503-8507 (2014) (Year: 2014).*
"Pharmaceutic," available online at https://www.vocabulary.com/dictionary/pharmaceutical, 2 pages (accessed on Sep. 9, 2019) (Year: 2019).*
"Preservatives," available online at https://www.chemicalsafetyfacts.org/preservatives/, 4 pages (accessed on Sep. 9, 2019) (Year: 2019).*
Merriam-Webster, "Veterinary," available online at https://www.merriam-webster.com/dictionary/veterinary, 12 pages (accessed on Sep. 9, 2019) (Year: 2019).*
"Nonnatural," available online at https://www.vocabulary.com/dictionary/nonnatural, 2 pages (accessed on Sep. 9, 2019) (Year: 2019).*
Adessi et al., Curr. Med. Chem. 9:963-978 (2002) (Year: 2002).*
GenBank Database, Accession No. WP_001867162.1, 1 page (first available 2013) (Year: 2013).*
Benjdia et al., Nat. Chem., Supplemental Information, 52 pages (2017) (Year: 2017).*
Flühe, L. et al. "The radical SAM enzyme AlbA catalyzes thioether bond formation in subtilosin A" *Nature Chemical Biolology*, Apr. 2012, pp. 350-357, correction p. 1, vol. 8.
Benjdia, A. et al. "Post-translational modification of ribosomally synthesized peptides by a radical SAM epimerase in *Bacillus subtilis*" *Nature Chemistry*, 2017, pp. 1-10.
NCBI TIGR04077, Conserved Protein Domain Family expor_sig_YdyF, 2019, p. 1.
Butcher, B. G. et al. "The *yydFGHIJ* Operon of *Bacillus subtilis* Encodes a Peptide That Induces the LiaRS Two-Component System" *Journal of Bacteriology*, Dec. 2007, pp. 8616-8625, vol. 189, No. 23.
Feitelson, M. A. "Parallel epigenetic and genetic changes in the pathogenesis of hepatitis virus-associated hepatocellular carcinoma" *Cancer Letters*, Jul. 28, 2006, pp. 10-20, vol. 239, No. 1.
Database UniProt [Online] Accession No. Q45596, Apr. 14, 2009, XP-055256737, retrieved from the Internet: URL: http://ibis.internal.epo.org/exam/dbfetch.jsp?id=UNIPROT:Q45596, on Mar. 9, 2016, pp. 1-2.
Written Opinion in International Application No. PCT/EP2016/079362, dated Feb. 14, 2017, pp. 1-6.

* cited by examiner

*Primary Examiner* — Thea D'Ambrosio
(74) *Attorney, Agent, or Firm* — Saliwanchik, Lloyd & Eisenschenk

(57) ABSTRACT

The present invention relates to a new class of peptides having antibacterial activity and presenting D-amino acids and their uses. It also relates to a new enzyme presenting a peptide epimerase activity in vitro and in vivo, thereby being useful for modifying peptides in order to change the amino acid configuration from L to D.

11 Claims, 21 Drawing Sheets

Specification includes a Sequence Listing.

Fig 1D

| SEQ ID No | | |
|---|---|---|
| 1 | ------------MKKEITNNETVKNLEFKGLLDESQKLAKVNDLWYFVKSKENRWILGS**GH--- | 49 |
| 2 | ------------MKKENTNNETVKNLEFKGLLDESQKLAKVNDLWYFVKSKENRWILGS**GH--- | 49 |
| 3 | ------------MKKENTNNETVKNLEFKGLLDESQKLAKVNDLWYFVKSQENRWILGS**GH--- | 49 |
| 4 | ------------MKKENTNNEPVKNLEFKGLLDESQKLAKVNDLWYFVKSKENRWILGS**GH--- | 49 |
| 5 | ------------MSKENTQNSNVKNLEFKSLVEESQKLAKVNDLWYFVKSKGNRWIVGS**GH--- | 49 |
| 6 | --------MKKEINSYKSTKENTMKDLEFKKLVNDSEKLAKVNDLWYFVKSQSNRWIVGS**GH--- | 54 |
| 7 | --------MKENLKVEKQNKKEVMKDLEFKTLINDSQKLAKVNDLWYFVKSKQNRWVVGS**GH--- | 54 |
| 8 | MKGKGDIKKNKDVQIQKKDKKDAMKNLEFKNLVNDSEKLAKVNDLWYFVKSKSHRWIVGS**GH--- | 62 |
| 9 | --------MNKDLHNQKNNKQDVMKDLEFKNLVNNSEKLAKVNDLWYFVKSKANRWVVGS**GH--- | 54 |
| 10 | ----------------------MKKLEIKELISKSEKLAKVNDLWYFVRSGEGAWIVGS**GGGSK | 42 |
| 11 | ----------------------MKELEMKELVEKSEKLAKVNDLWYFVKSSSGAWIAGS**GR--- | 39 |
| 12 | ----------------------MKELEMKELVEKSEKLAKINDLWYFVKSKGGAWIAGS**GK--- | 39 |
| 13 | ------------MWNNY--KGDIIMKELEMKELVEKSEKLAKINDLWYFVKSKGGAWIAGS**GK--- | 49 |
| 14 | --------MTIEIKNIQREVKPILNDMSFAKVLTKKNKLDNVNDLWYFVRNSKNRWVAGS**AH--- | 54 |
| 15 | ----------MKQKNIQREVKPILNDMSFAKVLTKKNELDNVNDLWYFVRSSKNRWVAGS**AH--- | 52 |
| 16 | -----------------------MSFAKVLTKKNKLDNVNDLWYFVRNSKNRWVAGS**AH--- | 36 |
| 17 | ------------MCNNY--KGDIIMKELEMKELVEKSEKLAKINDLWYFVKSKGGAWIAGS**GK--- | 49 |
| 18 | ------------MCNNY--KGDIIMK-----ELVEKSEKLAKINDLWYFVKSKGGAWIAGS**GK--- | 44 |
| 19 | ----------------------MEKSSEILNSLQA---NENVIDLEDQDDLWYFIKGG-GNWIMGS**----- | 44 |
|   | .  .* . :*****::   *: ** | |

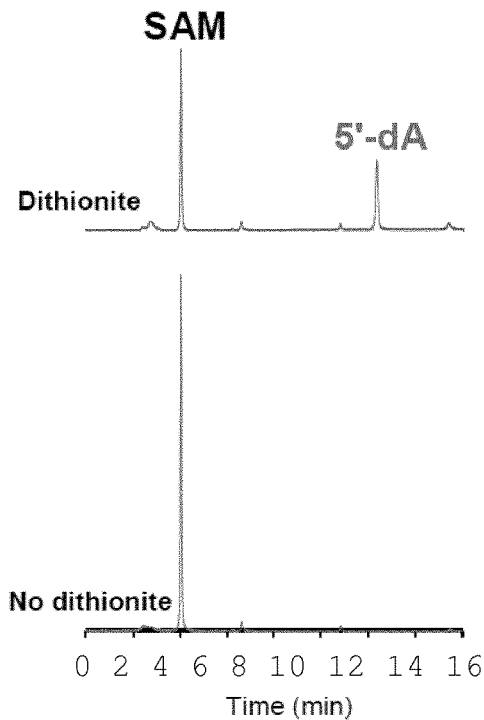

Fig 1E

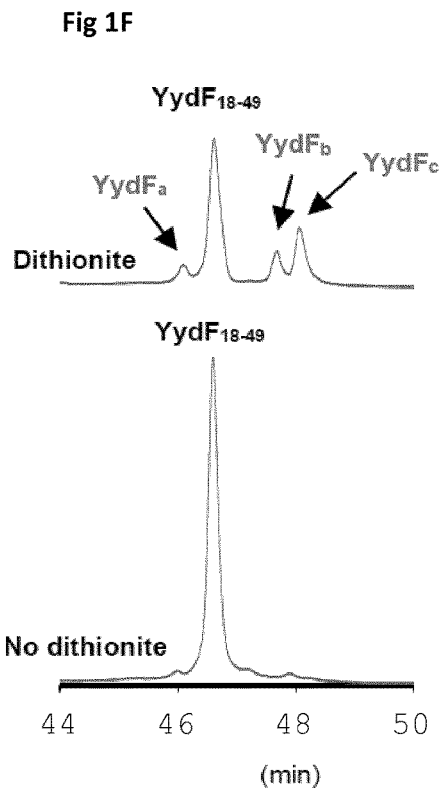

Fig 1F

Ac-MKKEITNNETVKNLEFKGLLDESQKLAKVNDLWYFVKSKENRWILGSGH-NH$_2$ (SEQ ID No 1)

Ac-GLLDESQKLAKVNDLWYFVKSKENRWILGSGH-NH$_2$ (SEQ ID No 20)

Fig 4A
MYNKTVSINLDSR$C_{14}$NAS$C_{18}$DH$C_{21}C_{22}$FSSSPTSTTRMEKEYIRELVTEFAKNKTIQVISFTGGEVFLDYKF
LKELMEIIKPYEKQITLISNGFWGLSKKKVQEYFHDMNSLNVIALTISYDEYHAPFVKSSSIKNILEHSRKY
PDIDISLNMAVTKDKMSNHILEELGDSILGVKITKFPMISVGAAKTRIKQENIHKFYSLEDEDSLHCPGYDI
VYHHDGEIYP$C_{222}C_{223}$SPAIFETKITLREEYNQSFERTVEKLNSNLLLFILRKEGFKWFLNILKENNKIEEFD
IPYEFSSICGVCGSLFNSAEKINYFYPYMEKYYNENFKV (SEQ ID NO 25)

Fig 4B

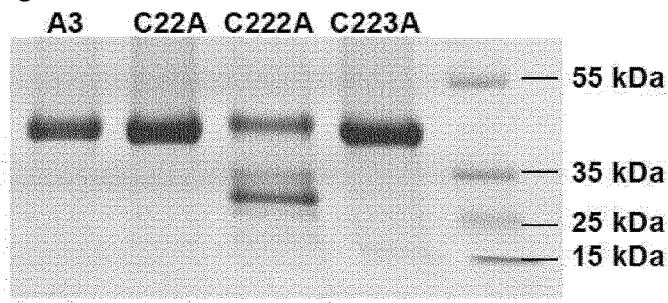

Fig 4C

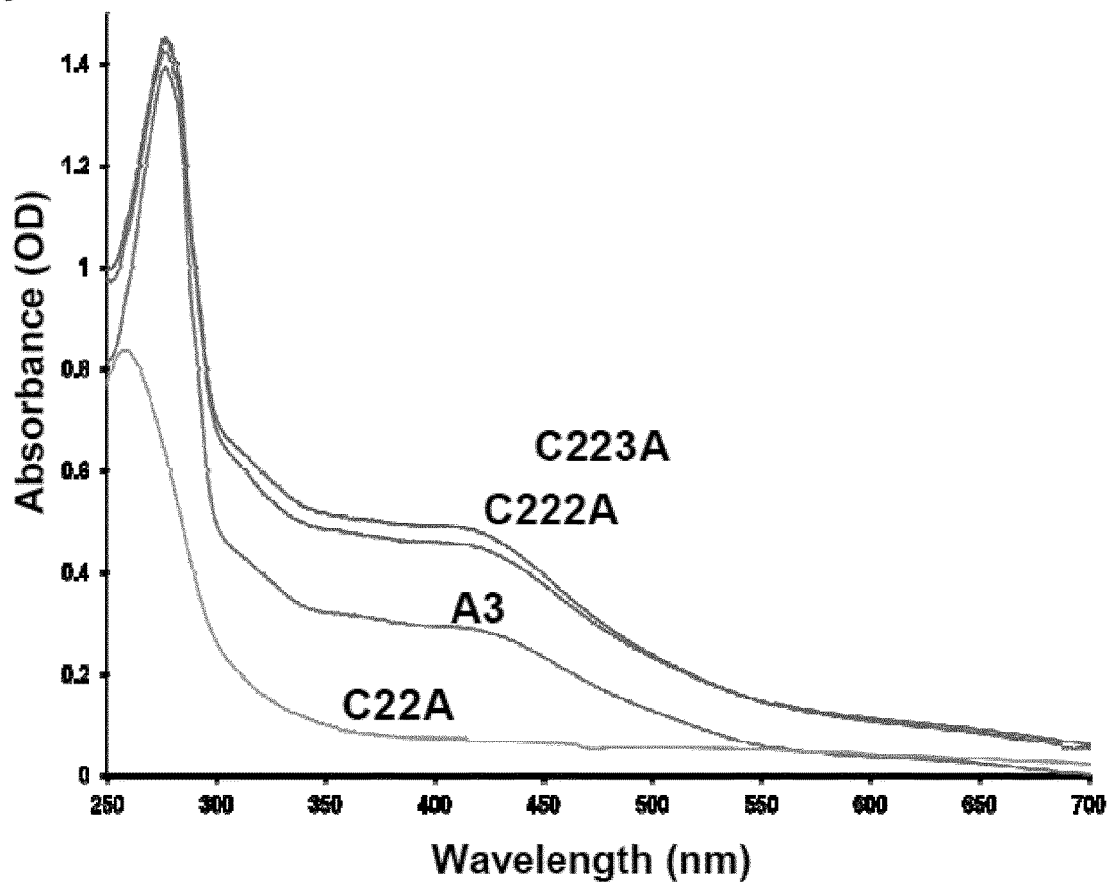

FIGURE 6 (continued)

```
SEQ ID No
25  VTEFAKNKTIQVISFTGGEVFLDYKFLKELMEIIKPYEKQITLISNGFWGLSKKKVQEYF  101
26  VTEFAKNKTIQVISFTGGEVFLDYKFLKELMEIIKPYEKQITLISNGFWGLSKKKVQEYF  101
27  VTEFAKNKTIQVISFTGGEVFLDYKFLKELMEIIKPYEKQITLISNGFWGLSKKKVQEYF  101
28  VTEFAKNKTIQVISFTGGEVFLDYKFLKELMEIIKPYEKQITLISNGFWGLSKKKVQEYF  101
29  VTEFAKNKTIQVISFTGGEVFLDYKFLKELMEIIKPYEKQITLISNGFWGMSKKRVQEYF  101
30  VTEFAKNKTIQVISFTGGEVFLDYKFLKELMEIIKPYEKQITLISNGFWGLSKKKVQEYF  101
31  VTEFAKNKTIQVISFTGGEVFLDYKFLKELMEIIKPYEKQITLISNGFWGISKKKVQEYF  101
32  VTEFAKNKTIQVISFTGGEIFLDYIFLKELMEIIKPYEKQITLISNGFWGVSRKRVQEYF  101
33  VTEFAKNKTIQVISFTGGEIFLDYIFLKELMEIIKPYEKQITLISNGFWGVSRKRVQEYF  101
34  VTEFAENKTIQVISFTGGEVFLDYTFLKELMEIIKPYEKQITLISNGFWGISKKKVQEYF  101
35  VNEFARSKTIEVISFTGGEIFLDYKFLKELMEIIKPYKKQITLISNGFWGGSQNKVEEYF  101
36  VLEFSKNPNIKVISFTGGEIFLNYQFLEELLKITKFYNKKITLISNGFWGASRRLLRKYF  101
37  VLEFAKDSNVEVISFTGGEIFLNYEFLEELLKITKNYNKKVTLISNGFWGNSRKLLEKYF  101
38  VLEFSKNPNIEIISFTGGEIFLNYKFLEELLIITKSYNKKVTLISNGFWGSSRKLLRKFF  101
39  AHELAENKKVNLISFTGGEIFLNYPFLQELLEIIKPHQKRITLISNGFWGMSRKKTEQYF  100
40  AHELAENKKVNLISFTGGEIFLNYPFLQELLEIIKPHQKRITLISNGFWGMSRKKTEQYF  120
41  AHELAENKKVNLISFTGGEIFLNYPFLQELLEIIKPHQKRITLISNGFWGMSRKKTEQYF  120
42  VKSFSNNLKIKVISFTGGEIFLNYSFLKELLEIVHSCGKKSTLISNGFWGANVEKVKIYF  100
43  VENFSNNPKIKTISFTGGEIFLNYPFLYSLLKIVNSSGKISTLISNGFWGREIETVKKYF  103
44  VENFSNNPKIKTISFTGGEIFLNYPFLYNLLKIVNSSGKISTLISNGFWGREIETVKKYF  100
45  VENFSNNPKIKTISFTGGEIFLNYPFLYNLLKIVNSSGKISTLISNGFWGREIETVKKYF  100
46  VENFSNNPKIKTISFTGGEIFLNYPFLYSLLKIVNSSGKISTLISNGFWGREIETVKKYF  100
47  VENFSNNPKIKTISFTGGEIFLNYPFLYSLLKIVNSSGKISTLISNGFWGREIETVKKYF  107
48  VENFSNNPKIKTISFTGGEIFLNYPFLYNLLKIVNSSGKISTLISNGFWGREIETVKKYF  107
49  VENFSNNPKIKTISFTGGEIFLNYPFLYSLLKIVNSSGKISTLISNGFWGREIETVKKYF  107
50  VENFSNNPKIKTISFTGGEIFLNYPFLYNLLKIVNSSGKISTLISNGFWGREIETVKKYF  100
51  VKEGCETPAIDTISLSGGEALLRKPLVLEVLRVAKSYGKAATLVTNGFWGQNKKRAEETL  99
52  VRYAETHEDVELVSLTGGEALLRKSKVLETIHRLSILGKDVTLITNGFWATNDKNTKSLL  99
53  VDDAIANAHVNSIGFSGGEALLHRNLLLSLMKRASEGNLKTTLVSNGFWGHSVANAQNIL  99
           :. :.::***  :*       : . :       **::****.  .  . :
```

FIGURE 6 (continued)

```
SEQ ID No
25  HDMNSLNVIALTISYDEYHAPFVKSSSIKNILEHSRKYP-DIDISLNMAVTKDKMSNHIL  160
26  HDMNSLNVIALTISYDEYHAPFVKSSSIKNILEHSRKYP-DIDISLNMAVTKDKMSNHIL  160
27  HDMSSLNVIALTISYDEYHAPFVKSSSIKNILEHSRKYP-DIDISLNMAVTKDKMSNHIL  160
28  HDMNSLNVIALTISYDEYHAPFVKSSSIKNILEHSRKYP-DIDISLNMAVTKDKMSNHIL  160
29  HDMNSLNVIALTISYDEYHAPFVKSSSIKNILEHSRKYP-DIDISLNMAVTKDKMSNHIL  160
30  HDMNSLNVIALTISYDEYHAPFVKSSSIKNILEHSRKYP-DIDISLNMAVTKDKMSNHIL  160
31  HDMNSLNVIALTISYDEYHAPFVKPSSVKRIFEHSRKYRGSIDISLNMAVTKDKMSNHIL  161
32  YDMNSLNVVALTISYDEYHAPFVKSSSIKNILEHSRKYP-DIDISLNMAVTKDKMSNHIL  160
33  YDMNSLNVVALTISYDEYHAPFVKSSSIKNILEHSRKYP-DIDISLNMAVTKDKMSNHIL  160
34  HDMNTLNVVALTISYDEYHAPFVKPSSIKRIFEHSRKYRGSIDISLNMAVTKDKMSNHIL  161
35  KDMNSLNVVALTISYDEYHAPFVKLSSVKRIFEHSRKYP-DIDVSLNMAVTKDKMSNRIL  160
36  EDFQKYNVVALTISYDEYHSPYVKIKSIKNIFDYRMKYP-EIEVSLNMAVTKEKMSDNIL  160
37  SDFYKYNVVALTISYDEYHSPFVKLKSIKNIFEYRMKYP-EIQVSLNMAVTKDKMSDNIL  160
38  DDFKKYNVIALTISYDEYHEPFIKLKSVKNIFEYRMKYP-EIEVSLNMAVTKDKMSDNIL  160
39  NDMEYYNVTNLTISYDEFHEPYVKADAIKNILECSRDFS-NTSVALNMAVTKSKMSNRIL  159
40  NDMEYYNVTNLTISYDEFHEPYVKADAIKNILECSRDFS-NTSVALNMAVTKSKMSNRIL  179
41  NDMEYYNVTNLTISYDEFHEPYVKADAIKNILECSRDFS-NTSVALNMAVTKSKMSNRIL  179
42  KDMKELGVTNLSISHDDFHAKFVKTDCIKNILEESRKYP-SIRVVVNIAVSKSNMGNKVI  159
43  LDMNRMGVTNLSISHDDFHSKFIKTDYIRNILIESRKYP-DIQITVNIAVSKNSTGDKII  162
44  LDMNRMGVTNLSISHDDFHSKFIKTDYIRNILIESRKYP-DIQITVNIAVSKNSTGDKII  159
45  LDMNRMGVTNLSISHDDFHSKFIKTDYIRNILIESRKYP-DIQITVNIAVSKNSTGDKII  159
46  LDMNRMGVTNLSISHDDFHSKFIKTDYIRNILIESRKYP-DIQITVNIAVSKNSTGDKII  159
47  LDMNRMGVTNLSISHDDFHSKFIKTDYIRNILIESRKYP-DIQITVNIAVSKNSTGDKII  166
48  LDMNRMGVTNLSISHDDFHSKFIKTDYIRNILIESRKYP-DIQITVNIAVSKNSTGDKII  166
49  LDMNRMGVTNLSISHDDFHSKFIKTDYIRNILIESRKYP-DIQITVNIAVSKNSTGDKII  166
50  LDMNRMGVTNLSISHDDFHSKFIKTDYIRNILIESRKYP-DIQITVNIAVSKNSTGDKII  159
51  FELKEAGLCALKISFDDFHQDLLKVEKVKNILDANLSVR--VPIAINVAVSKNFSSDRIL  157
52  TSLRTAGLRYLTVSYDNYHSEYIPVDNIKRLFLHIKKFD--IEVALNMVVDKKNRGVDLL  157
53  TLLKNAGLSTLTLSFDEFHEKFIPTQRIINILQANKYIG--IPCHISMAVTKDHTGEELI  157
         :       :   *.:*.*::*     :   .  :  .::          :..:.* *.  .   ::
```

FIGURE 6 (continued)

```
SEQ ID No
25 EELGDSILGVKITKFPMISVGAAKTRIKQENIHKFYSLEDE-DSLHCP--GYDIVYHHDG 217
26 EELGDSILGVKITKFPMISVGAAKTRIKQENIHKFYSLEDE-DSLHCP--GYDIVYHHDG 217
27 EELGDSILGVKITKFPMISVGAAKTRIKQENIHKFYSLEDE-DSLHCP--GYDIVYHHDG 217
28 EELGDSILGVKITKFPMISVGAAKTRIKQENIHKFYSLEDE-DSLHCP--GYDIVYHHDG 217
29 EELGDSILGVKITKFPMISVGAAKTRIKQENIHKFYSLEDE-DSLHCP--GYDIVYHHDG 217
30 EELGDSILGVKITKFPMISVGAAKTRIKQENIHKFYSLEDE-DSLHCP--GYDIVYHHDG 217
31 EELGDSILGVKITKFPMISVGAAKNRIKQENIHKFYSLEDE-DSLHCP--GYDIVYHHDG 218
32 EELGDSILGVKITKFPMISVGAARTRIRQENIHKFYNLDDE-DSLYCP--GYEIVYHHDG 217
33 EDLGDSILGVKITKFPMISVGAARTRIRPENIHKFHNLDDD-DSLYCP--GYEIVYHHDG 217
34 EELGDSILGVKITKFPMISVGAAKSRIKQENIHKFYSLEDE-DSLQCP--GYDIVYHHDG 218
35 EELGDSILGIKITKFPLIPVGAAKNRISQENIHKFYNLDDE-DSLQCP--GYEIVYHHDG 217
36 RELGSSVLGIKITKFPMITVGAAKKNIAKENIHNFYNVEKDKSILYCP--GYELVYHHDG 218
37 RELGSSILGAKITKFPMISVGAAKDKISKENIHNFYNINKDREVLYCP--GFEIVYHHDG 218
38 SELGSSILGIKITKFPMITVGSAKNKISKNNIHNFYNIEKDKNLLFCP--GYEIVYHHDG 218
39 EYMGESLLGIRVTKFPLMPVGEAKHE-EPDSFQHIYKLSNE-RSLHCP--GFEVVYHFDG 215
40 EYMGESLLGIRVTKFPLMPVGEAKHE-EPDSFQHIYKLSNE-RSLHCP--GFEVVYHFDG 235
41 EYMGESLLGIRVTKFPLMPVGEAKHE-EPDSFQHIYKLSNE-RSLHCP--GFEVVYHFDG 235
42 EELDEAALGIPLTKYPLIAVGEAENM-ADSEFQKIYSIDNL-EQLECP--GYEPVYHFDG 215
43 HDLGEAILGIPVTKFPLIPVGEAKNI-NDDEFQNIYSLSHP-NQLKCP--GFEPVYHFNG 218
44 HDLGEAILGIPVTKFPLIPVGEAKNI-NDDEFQNIYSLSHP-NQLKCP--GFEPVYHFNG 215
45 HDLGEAILGIPVTKFPLIPVGEAKNI-NDDEFQNIYSLSHP-NQLKCP--GFEPVYHFNG 215
46 HDLGEAILGIPVTKFPLIPVGEAKNI-NDDEFQNIYSLSHP-NQLKCP--GFEPVYHFNG 215
47 HDLGEAILGIPVTKFPLIPVGEAKNI-NDDEFQNIYSLSHP-NQLKCP--GFEPVYHFNG 222
48 HDLGEAILGIPVTKFPLIPVGEAKNI-NDDEFQNIYSLSHP-NQLKCP--GFEPVYHFNG 222
49 HDLGEAILGIPVTKFPLIPVGEAKNI-NDDEFQNIYSLSHP-NQLKCP--GFEPVYHFNG 222
50 HDLGEAILGIPVTKFPLIPVGEAKNI-NDDEFQNIYSLSHP-NQLKCP--GFEPVYHFNG 215
51 AALGESLMGVKVIKFPIQRVGAAEQYP-E---ESIIRRHRIEDNLTCP--GFEPTYHYDG 211
52 DKLGESIFGVPITIVPASPVGRAKNLN----MEDLYLKTIDELELTCPATGWEFVIHHDG 213
53 HDLGEAGFTIPITRFPVVPVGAAAQLP-K---ENIYSHYDANDPLICP--GLQITYHFNG 211
     : .: :    :    *   ** *           . :        * **  * : . *.:*
```

FIGURE 6 (continued)

```
SEQ ID No
25 EIYPCCSPAIFETKITLREEYNQSFERTVEKLNSNLLLFILRKEGFKWFLNILKENNKIE 277
26 EIYPCCSPAIFETKITLREEYNQSFERTVEKLNSNLLLFILRKEGFKWFLNILKENNKIE 277
27 EIYPCCSPAIFETKITLREEYNQSFERTVEKLNSNLLLFILRKEGFKWFLNILKENNKIE 277
28 EIYPCCSPAIFETKITLREEYNQSFERTVEKLNSNLLLFILRKEGFKWFLNILKENNKIE 277
29 EIYPCCSPAIFETKITLREEYSQSFERTVEKLNSNLLLFILRKEGFKWFLNILKENNKIE 277
30 EIYPCCSPAIFETKITLREEYNQSFERTVEKLNSNLLLFILRKEGFKWFLNILKENNKIE 277
31 EIYPCCSPAIFETKITLREEYNQSFERTVEKLNSNLLLFILRKEGFKWFLNILKENNKIE 278
32 EIYPCCSPAIFETKITLREEYNQNFERTVEKLNSNLLLFILRKEGFKWFLDILKENNKIE 277
33 EIYPCCSPAIFETKITLREEYNQNFERTVEKLNSNLLLFILRKEGFKWFLDILKENNKIE 277
34 EIYPCCSPAIFETKITLREDYNQNFERTVEKLKSNLLLFILRKEGFKWFLDILKDNNKIE 278
35 EIYPCCSPAIFETKITLREEYSQTYERTVEKLQSNLLLFIIRKEGFKWFLNILKENKKIE 277
36 EIYPCCSPAIFETSITLRESENQTFERTIEKLNSNLLLYIIRKEGFNWFIKILKNNNLMD 278
37 EIYPCCSPAIFETPITLRENKNQTLTRTVEKLNSNLLLYIIRKEGFNWFLDILREENMLH 278
38 EIYPCCSPAIFETKISLREDKYQTLERTIEKLNSNLLLYIVRKEGFNWFLDIVREQDLLN 278
39 QIYPCCSPAVFDTKLHLRESMDQTFDRTIEKLNANLLFYIMRKEGFKWFIDIVQSNPEFN 275
40 QIYPCCSPAVFDTKLHLRESMDQTFDRTIEKLNANLLFYIMRKEGFKWFIDIVQSNPEFN 295
41 QIYPCCSPAVFDTKLHLRESMDQTFDRTIEKLNANLLFYIMRKEGFKWFIDIVQSNPEFN 295
42 NVYPCCSPAVFDTALILNDRACQSFDKTIEKMNANLLLYIMRKEGFRWFIEIVMSNQEFS 275
43 NVYPCCSPAIFDTALILNDELYQDFDKTITKMNSNLLLYIMRREGFSWFINIVSNNNEFS 278
44 NVYPCCSPAIFDTALILNDELYQEFDKTITKMNSNLLLYIMRREGFSWFINIVSNNNEFS 275
45 NVYPCCSPAIFDTALILNDELYQEFDKTITKMNSNLLLYIMRREGFSWFINIVSNNNEFS 275
46 NVYPCCSPAIFDTALILNDELYQDFDKTITKMNSNLLLYIMRREGFSWFINIVSNNNEFS 275
47 NVYPCCSPAIFDTALILNDELYQDFDKTITKMNSNLLLYIMRREGFSWFINIVSNNNEFS 282
48 NVYPCCSPAIFDTALILNDELYQEFDKTITKMNSNLLLYIMRREGFSWFINIVSNNNEFS 282
49 NVYPCCSPAIFDTALILNDELYQYFDKTITKMNSNLLLYIMRREGFSWFINIVSNNNEFS 282
50 NVYPCCSPAIFDTALILNDELYQEFDKTITKMNSNLLLYIMRREGFSWFINIVSNNNEFS 275
51 KVYPCCSPTVFTTGLTFGKAEDLPVERAVSSIERNLLFAAIRQKGFKWLFERCIEERVLD 271
52 YVYPCCSPSVFETNLRIGSIGDADISELEDKFYSNMLLYILKREGFTWFIDKMKLDL--- 270
53 DVYPCCSPAVFHTCLSIGEVSNTPTHTALERVSRNKLFALMQRIGLRGIAEICKEHGI-G 270
   :******::* * : .          . * *:   ::: *:   :  .         .
```

FIGURE 6 (continued)

```
SEQ ID No
25 EFDIPYEFSSICGVCGSLFNSAEKINYFYPYMEKYYNENFKV-------- 319
26 EFDIPYEFSSICGVCGSLFNSAEKINYFYPYMEKYYNENFKV-------- 319
27 EFDIPYEFSSICGVCGSLFNSAEKINYFYPYMEKYYNENFKV-------- 319
28 EFDIPYEFSSICGVCGSLFNSAEKINYFYPYMEKYYNENFKV-------- 319
29 EFDIPYEFSSICGVCGSLFNSAEKINYFYPYMEKYYNENFKV-------- 319
30 EFDIPYEFSSICGVCGSLFNSAEKINYFYPYMEKYYNENFKV-------- 319
31 EFDIPYEFSSICGVCGSLFNSAEKINYFYPYMEKYYNENFKV-------- 320
32 EFDIPYEFSSICGVCGSLFNSAEKINYFYPHMEKYYYENFEV-------- 319
33 EFDIPYEFSSICGVCGSLFNSAEKINYFYPHMEKYYYENFEV-------- 319
34 EFDIPYEFSSICGVCGSLFNSVEKINYFYPYMEKYYHENFEV-------- 320
35 EFGIPYEFSSICSLCVSLFNSEDKINYFHNFMEDYYYANYGNKDHETAKI 327
36 SFEIPEDFPSVCSVCGSLFNSEEKIEFFKPYMEKYYENF-EI-------- 319
37 QFDIPTDFPSVCSICGSLFSTEEKIKFFKPFMEAYYYETIEV-------- 320
38 EFEIPKDFPSVCSICGNLFNTEEKINFFKPYMKEYYYETIKV-------- 320
39 HIKIPEQFSSICNICNILFKTEENIDLLTPYMMNYYENMV---------- 315
40 HIKIPEQFSSICNICNILFKTEENIDLLTPYMMNYYENMV---------- 335
41 HIKIPEQFSSICNICNILFKTEENIDLLTPYMMNYYENMV---------- 335
42 HIQIEEHFSSICTICRQLFKSEENIKLFTPYMREYYEQML---------- 315
43 HIKINKEFSSICSICRQLFKTENNIKLLTPYMRKYYEQML---------- 318
44 HIKINKEFSSICSICRQLFKTENNIKLLTPYMRKYYEQML---------- 315
45 HIKINKEFSSICSICRQLFKTENNIKLLTPYMRKYYEQML---------- 315
46 HIKINKEFSSICSICRQLFKTENNIKLLTPYMRKYYEQML---------- 315
47 HIKINKEFSSICSICRQLFKTENNIKLLTPYMRKYYEQML---------- 322
48 HIKINKEFSSICSICRQLFKTENNIKLLTPYMRKYYEQML---------- 322
49 HIKINKEFSSICSICRQLFKTENNIKLLTPYMRKYYEQML---------- 322
50 HIKINKEFSSICSICRQLFKTENNIKLLTPYMSQVQTPV----------- 314
51 ISYIDRSYVDACEMCQILFSNPHTLKAVVSIVSNEYTSISK--------- 312
52 ---TGKKFVSSCEVCKFIFSDMNKIKSITDDIKEYYVKEFENIGVSKL-- 315
53 PDLTKVPVVDPCDLCRKIFANSKTLEALLPYIDQAYRKTLPDKVQS---- 316
         . * :*   :*   ..:. .   :
```

SEQUENCE LISTING

<160> NUMBER OF SEQ ID NOS: 79

<210> SEQ ID NO 1
<211> LENGTH: 49
<212> TYPE: PRT
<213> ORGANISM: Bacillus subtilis

<400> SEQUENCE: 1

Met Lys Lys Glu Ile Thr Asn Asn Glu Thr Val Lys Asn Leu Glu Phe
1               5                   10                  15

Lys Gly Leu Leu Asp Glu Ser Gln Lys Leu Ala Lys Val Asn Asp Leu
            20                  25                  30

Trp Tyr Phe Val Lys Ser Lys Glu Asn Arg Trp Ile Leu Gly Ser Gly
        35                  40                  45

His

<210> SEQ ID NO 2
<211> LENGTH: 49
<212> TYPE: PRT
<213> ORGANISM: Bacillus subtilis

<400> SEQUENCE: 2

Met Lys Lys Glu Asn Thr Asn Asn Glu Thr Val Lys Asn Leu Glu Phe
1               5                   10                  15

Lys Gly Leu Leu Asp Glu Ser Gln Lys Leu Ala Lys Val Asn Asp Leu
            20                  25                  30

Trp Tyr Phe Val Lys Ser Lys Glu Asn Arg Trp Ile Leu Gly Ser Gly
        35                  40                  45

His

<210> SEQ ID NO 3
<211> LENGTH: 49
<212> TYPE: PRT
<213> ORGANISM: Bacillus sp

<400> SEQUENCE: 3

```
Met Lys Lys Glu Asn Thr Asn Asn Glu Thr Val Lys Asn Leu Glu Phe
1               5                   10                  15

Lys Gly Leu Leu Asp Glu Ser Gln Lys Leu Ala Lys Val Asn Asp Leu
                20                  25                  30

Trp Tyr Phe Val Lys Ser Gln Glu Asn Arg Trp Ile Leu Gly Ser Gly
            35                  40                  45

His

<210> SEQ ID NO 4
<211> LENGTH: 49
<212> TYPE: PRT
<213> ORGANISM: Bacillus subtilis

<400> SEQUENCE: 4

Met Lys Lys Glu Asn Thr Asn Asn Glu Pro Val Lys Asn Leu Glu Phe
1               5                   10                  15

Lys Gly Leu Leu Asp Glu Ser Gln Lys Leu Ala Lys Val Asn Asp Leu
                20                  25                  30

Trp Tyr Phe Val Lys Ser Lys Glu Asn Arg Trp Ile Leu Gly Ser Gly
            35                  40                  45

His

<210> SEQ ID NO 5
<211> LENGTH: 49
<212> TYPE: PRT
<213> ORGANISM: Bacillus coagulans

<400> SEQUENCE: 5

Met Ser Lys Glu Asn Thr Gln Asn Ser Asn Val Lys Asn Leu Glu Phe
1               5                   10                  15

Lys Ser Leu Val Glu Glu Ser Gln Lys Leu Ala Lys Val Asn Asp Leu
                20                  25                  30

Trp Tyr Phe Val Lys Ser Lys Gly Asn Arg Trp Ile Val Gly Ser Gly
            35                  40                  45

His

<210> SEQ ID NO 6
<211> LENGTH: 54
<212> TYPE: PRT
<213> ORGANISM: Staphylococcus pseudintermedius

<400> SEQUENCE: 6

Met Lys Lys Glu Ile Asn Ser Tyr Lys Ser Thr Lys Glu Asn Thr Met
1               5                   10                  15

Lys Asp Leu Glu Phe Lys Lys Leu Val Asn Asp Ser Glu Lys Leu Ala
                20                  25                  30

Lys Val Asn Asp Leu Trp Tyr Phe Val Lys Ser Gln Ser Asn Arg Trp
            35                  40                  45

Ile Val Gly Ser Gly His
    50

<210> SEQ ID NO 7
<211> LENGTH: 54
<212> TYPE: PRT
<213> ORGANISM: Staphylococcus equorum

<400> SEQUENCE: 7

Met Lys Glu Asn Leu Lys Val Glu Lys Gln Asn Lys Lys Glu Val Met
```

```
                1               5                  10                 15
Lys Asp Leu Glu Phe Lys Thr Leu Ile Asn Asp Ser Gln Lys Leu Ala
                 20                 25                 30

Lys Val Asn Asp Leu Trp Tyr Phe Val Lys Ser Lys Gln Asn Arg Trp
         35                 40                 45

Val Val Gly Ser Gly His
     50
```

<210> SEQ ID NO 8
<211> LENGTH: 62
<212> TYPE: PRT
<213> ORGANISM: Staphylococcus condimenti

<400> SEQUENCE: 8

```
Met Lys Gly Lys Gly Asp Ile Lys Lys Asn Lys Asp Val Gln Ile Gln
1               5                  10                 15

Lys Lys Asp Lys Lys Asp Ala Met Lys Asn Leu Glu Phe Lys Asn Leu
                 20                 25                 30

Val Asn Asp Ser Glu Lys Leu Ala Lys Val Asn Asp Leu Trp Tyr Phe
         35                 40                 45

Val Lys Ser Lys Ser His Arg Trp Ile Val Gly Ser Gly His
     50                  55                 60
```

<210> SEQ ID NO 9
<211> LENGTH: 54
<212> TYPE: PRT
<213> ORGANISM: Staphylococcus epidermidis

<400> SEQUENCE: 9

```
Met Asn Lys Asp Leu His Asn Gln Lys Asn Asn Lys Gln Asp Val Met
1               5                  10                 15

Lys Asp Leu Glu Phe Lys Asn Leu Val Asn Asn Ser Glu Lys Leu Ala
                 20                 25                 30

Lys Val Asn Asp Leu Trp Tyr Phe Val Lys Ser Lys Ala Asn Arg Trp
         35                 40                 45

Val Val Gly Ser Gly His
     50
```

<210> SEQ ID NO 10
<211> LENGTH: 42
<212> TYPE: PRT
<213> ORGANISM: Paenibacillus sp

<400> SEQUENCE: 10

```
Met Lys Lys Leu Glu Ile Lys Glu Leu Ile Ser Lys Ser Glu Lys Leu
1               5                  10                 15

Ala Lys Val Asn Asp Leu Trp Tyr Phe Val Arg Ser Gly Glu Gly Ala
                 20                 25                 30

Trp Ile Val Gly Ser Gly Gly Ser Lys
         35                 40
```

<210> SEQ ID NO 11
<211> LENGTH: 39
<212> TYPE: PRT
<213> ORGANISM: Enterococcus caccae

<400> SEQUENCE: 11

```
Met Lys Glu Leu Glu Met Lys Glu Leu Val Glu Lys Ser Glu Lys Leu
1               5                  10                 15
```

Ala Lys Val Asn Asp Leu Trp Tyr Phe Val Lys Ser Ser Gly Ala
            20                  25                  30

Trp Ile Ala Gly Ser Gly Arg
            35

<210> SEQ ID NO 12
<211> LENGTH: 39
<212> TYPE: PRT
<213> ORGANISM: Enterococcus faecalis

<400> SEQUENCE: 12

Met Lys Glu Leu Glu Met Lys Glu Leu Val Glu Lys Ser Glu Lys Leu
1               5                   10                  15

Ala Lys Ile Asn Asp Leu Trp Tyr Phe Val Lys Ser Lys Gly Gly Ala
            20                  25                  30

Trp Ile Ala Gly Ser Gly Lys
            35

<210> SEQ ID NO 13
<211> LENGTH: 49
<212> TYPE: PRT
<213> ORGANISM: Enterococcus faecalis

<400> SEQUENCE: 13

Met Trp Asn Asn Tyr Lys Gly Asp Ile Ile Met Lys Glu Leu Glu Met
1               5                   10                  15

Lys Glu Leu Val Glu Lys Ser Glu Lys Leu Ala Lys Ile Asn Asp Leu
            20                  25                  30

Trp Tyr Phe Val Lys Ser Lys Gly Gly Ala Trp Ile Ala Gly Ser Gly
            35                  40                  45

Lys

<210> SEQ ID NO 14
<211> LENGTH: 54
<212> TYPE: PRT
<213> ORGANISM: Streptococcus agalactiae

<400> SEQUENCE: 14

Met Thr Ile Glu Ile Lys Asn Ile Gln Arg Glu Val Lys Pro Ile Leu
1               5                   10                  15

Asn Asp Met Ser Phe Ala Lys Val Leu Thr Lys Asn Lys Leu Asp
            20                  25                  30

Asn Val Asn Asp Leu Trp Tyr Phe Val Arg Asn Ser Lys Asn Arg Trp
            35                  40                  45

Val Ala Gly Ser Ala His
            50

<210> SEQ ID NO 15
<211> LENGTH: 52
<212> TYPE: PRT
<213> ORGANISM: Streptococcus agalactiae

<400> SEQUENCE: 15

Met Lys Gln Lys Asn Ile Gln Arg Glu Val Lys Pro Ile Leu Asn Asp
1               5                   10                  15

Met Ser Phe Ala Lys Val Leu Thr Lys Lys Asn Glu Leu Asp Asn Val
            20                  25                  30

Asn Asp Leu Trp Tyr Phe Val Arg Ser Ser Lys Asn Arg Trp Val Ala
            35                  40                  45

Gly Ser Ala His
    50

<210> SEQ ID NO 16
<211> LENGTH: 36
<212> TYPE: PRT
<213> ORGANISM: Streptococcus

<400> SEQUENCE: 16

Met Ser Phe Ala Lys Val Leu Thr Lys Lys Asn Lys Leu Asp Asn Val
1               5                   10                  15

Asn Asp Leu Trp Tyr Phe Val Arg Asn Ser Lys Asn Arg Trp Val Ala
            20                  25                  30

Gly Ser Ala His
    35

<210> SEQ ID NO 17
<211> LENGTH: 49
<212> TYPE: PRT
<213> ORGANISM: Enterococcus faecalis

<400> SEQUENCE: 17

Met Cys Asn Asn Tyr Lys Gly Asp Ile Ile Met Lys Glu Leu Glu Met
1               5                   10                  15

Lys Glu Leu Val Glu Lys Ser Glu Lys Leu Ala Lys Ile Asn Asp Leu
            20                  25                  30

Trp Tyr Phe Val Lys Ser Lys Gly Gly Ala Trp Ile Ala Gly Ser Gly
            35                  40                  45

Lys

<210> SEQ ID NO 18
<211> LENGTH: 44
<212> TYPE: PRT
<213> ORGANISM: Enterococcus faecalis

<400> SEQUENCE: 18

Met Cys Asn Asn Tyr Lys Gly Asp Ile Ile Met Lys Glu Leu Val Glu
1               5                   10                  15

Lys Ser Glu Lys Leu Ala Lys Ile Asn Asp Leu Trp Tyr Phe Val Lys
            20                  25                  30

Ser Lys Gly Gly Ala Trp Ile Ala Gly Ser Gly Lys
            35                  40

<210> SEQ ID NO 19
<211> LENGTH: 40
<212> TYPE: PRT
<213> ORGANISM: Bifidobacterium bohemicum

<400> SEQUENCE: 19

Met Glu Lys Ser Ser Glu Ile Leu Asn Ser Leu Gln Ala Asn Glu Asn
1               5                   10                  15

Val Ile Asp Leu Glu Asp Gln Asp Leu Trp Tyr Phe Ile Lys Gly
            20                  25                  30

Gly Gly Asn Trp Ile Met Gly Ser
            35                  40

<210> SEQ ID NO 20
<211> LENGTH: 32
<212> TYPE: PRT
<213> ORGANISM: Artificial Sequence
<220> FEATURE:

<223> OTHER INFORMATION: YyFd18-49

<400> SEQUENCE: 20

Gly Leu Leu Asp Glu Ser Gln Lys Leu Ala Lys Val Asn Asp Leu Trp
1               5                   10                  15

Tyr Phe Val Lys Ser Lys Glu Asn Arg Trp Ile Leu Gly Ser Gly His
            20                  25                  30

<210> SEQ ID NO 21
<211> LENGTH: 7
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa is D or N
<220> FEATURE:
<221> NAME/KEY: MISC_FEATURE
<222> LOCATION: (7)..(7)
<223> OTHER INFORMATION: Xaa is I, V or A

<400> SEQUENCE: 21

Xaa Asp Leu Trp Tyr Phe Xaa
1               5

<210> SEQ ID NO 22
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (2)..(2)
<223> OTHER INFORMATION: Xaa is I or V
<220> FEATURE:
<221> NAME/KEY: MISC_FEATURE
<222> LOCATION: (3)..(3)
<223> OTHER INFORMATION: Xaa is any amino acid

<400> SEQUENCE: 22

Trp Xaa Xaa Gly Ser
1               5

<210> SEQ ID NO 23
<211> LENGTH: 11
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (2)..(2)
<223> OTHER INFORMATION: Xaa is A, D or E
<220> FEATURE:
<221> NAME/KEY: MISC_FEATURE
<222> LOCATION: (3)..(3)
<223> OTHER INFORMATION: Xaa is K, N or D
<220> FEATURE:
<221> NAME/KEY: MISC_FEATURE
<222> LOCATION: (4)..(4)
<223> OTHER INFORMATION: Xaa is V, I or Q
<220> FEATURE:
<221> NAME/KEY: MISC_FEATURE
<222> LOCATION: (11)..(11)
<223> OTHER INFORMATION: Xaa is V or I

<400> SEQUENCE: 23

Leu Xaa Xaa Xaa Asn Asp Leu Trp Tyr Phe Xaa

```
1               5                  10
```

<210> SEQ ID NO 24
<211> LENGTH: 11
<212> TYPE: PRT
<213> ORGANISM: Artificial Sequence
<220> FEATURE:
<223> OTHER INFORMATION: motif

<400> SEQUENCE: 24

```
Leu Ala Lys Val Asn Asp Leu Trp Tyr Phe Val
1               5                  10
```

<210> SEQ ID NO 25
<211> LENGTH: 319
<212> TYPE: PRT
<213> ORGANISM: Bacillus subtilis

<400> SEQUENCE: 25

```
Met Tyr Asn Lys Thr Val Ser Ile Asn Leu Asp Ser Arg Cys Asn Ala
1               5                  10                  15

Ser Cys Asp His Cys Cys Phe Ser Ser Pro Thr Ser Thr Thr Arg
            20                  25                  30

Met Glu Lys Glu Tyr Ile Arg Glu Leu Val Thr Glu Phe Ala Lys Asn
        35                  40                  45

Lys Thr Ile Gln Val Ile Ser Phe Thr Gly Gly Glu Val Phe Leu Asp
    50                  55                  60

Tyr Lys Phe Leu Lys Glu Leu Met Glu Ile Ile Lys Pro Tyr Glu Lys
65                  70                  75                  80

Gln Ile Thr Leu Ile Ser Asn Gly Phe Trp Gly Leu Ser Lys Lys Lys
                85                  90                  95

Val Gln Glu Tyr Phe His Asp Met Asn Ser Leu Asn Val Ile Ala Leu
            100                 105                 110

Thr Ile Ser Tyr Asp Glu Tyr His Ala Pro Phe Val Lys Ser Ser Ser
        115                 120                 125

Ile Lys Asn Ile Leu Glu His Ser Arg Lys Tyr Pro Asp Ile Asp Ile
    130                 135                 140

Ser Leu Asn Met Ala Val Thr Lys Asp Lys Met Ser Asn His Ile Leu
145                 150                 155                 160

Glu Glu Leu Gly Asp Ser Ile Leu Gly Val Lys Ile Thr Lys Phe Pro
                165                 170                 175

Met Ile Ser Val Gly Ala Ala Lys Thr Arg Ile Lys Gln Glu Asn Ile
            180                 185                 190

His Lys Phe Tyr Ser Leu Glu Asp Glu Asp Ser Leu His Cys Pro Gly
        195                 200                 205

Tyr Asp Ile Val Tyr His His Asp Gly Glu Ile Tyr Pro Cys Cys Ser
    210                 215                 220

Pro Ala Ile Phe Glu Thr Lys Ile Thr Leu Arg Glu Glu Tyr Asn Gln
225                 230                 235                 240

Ser Phe Glu Arg Thr Val Glu Lys Leu Asn Ser Asn Leu Leu Leu Phe
                245                 250                 255

Ile Leu Arg Lys Glu Gly Phe Lys Trp Phe Leu Asn Ile Leu Lys Glu
            260                 265                 270

Asn Asn Lys Ile Glu Glu Phe Asp Ile Pro Tyr Glu Phe Ser Ser Ile
        275                 280                 285

Cys Gly Val Cys Gly Ser Leu Phe Asn Ser Ala Glu Lys Ile Asn Tyr
    290                 295                 300
```

```
Phe Tyr Pro Tyr Met Glu Lys Tyr Tyr Asn Glu Asn Phe Lys Val
305                 310                 315
```

```
<210> SEQ ID NO 26
<211> LENGTH: 319
<212> TYPE: PRT
<213> ORGANISM: Bacillus subtilis

<400> SEQUENCE: 26

Met Tyr Asn Lys Thr Val Ser Ile Asn Leu Asp Ser Arg Cys Asn Ala
1               5                   10                  15

Ser Cys Asp His Cys Cys Phe Ser Ser Pro Ser Ser Thr Thr Arg
            20                  25                  30

Met Glu Lys Glu Tyr Ile Arg Glu Leu Val Thr Glu Phe Ala Lys Asn
            35                  40                  45

Lys Thr Ile Gln Val Ile Ser Phe Thr Gly Gly Glu Val Phe Leu Asp
        50                  55                  60

Tyr Lys Phe Leu Lys Glu Leu Met Glu Ile Ile Lys Pro Tyr Glu Lys
65                  70                  75                  80

Gln Ile Thr Leu Ile Ser Asn Gly Phe Trp Gly Leu Ser Lys Lys Lys
                85                  90                  95

Val Gln Glu Tyr Phe His Asp Met Asn Ser Leu Asn Val Ile Ala Leu
            100                 105                 110

Thr Ile Ser Tyr Asp Glu Tyr His Ala Pro Phe Val Lys Ser Ser Ser
            115                 120                 125

Ile Lys Asn Ile Leu Glu His Ser Arg Lys Tyr Pro Asp Ile Asp Ile
130                 135                 140

Ser Leu Asn Met Ala Val Thr Lys Asp Lys Met Ser Asn His Ile Leu
145                 150                 155                 160

Glu Glu Leu Gly Asp Ser Ile Leu Gly Val Lys Ile Thr Lys Phe Pro
                165                 170                 175

Met Ile Ser Val Gly Ala Ala Lys Thr Arg Ile Lys Gln Glu Asn Ile
            180                 185                 190

His Lys Phe Tyr Ser Leu Glu Asp Glu Asp Ser Leu His Cys Pro Gly
            195                 200                 205

Tyr Asp Ile Val Tyr His His Asp Gly Glu Ile Tyr Pro Cys Cys Ser
        210                 215                 220

Pro Ala Ile Phe Glu Thr Lys Ile Thr Leu Arg Glu Glu Tyr Asn Gln
225                 230                 235                 240

Ser Phe Glu Arg Thr Val Glu Lys Leu Asn Ser Asn Leu Leu Leu Phe
                245                 250                 255

Ile Leu Arg Lys Glu Gly Phe Lys Trp Phe Leu Asn Ile Leu Lys Glu
            260                 265                 270

Asn Asn Lys Ile Glu Glu Phe Asp Ile Pro Tyr Glu Phe Ser Ser Ile
            275                 280                 285

Cys Gly Val Cys Gly Ser Leu Phe Asn Ser Ala Glu Lys Ile Asn Tyr
        290                 295                 300

Phe Tyr Pro Tyr Met Glu Lys Tyr Tyr Asn Glu Asn Phe Lys Val
305                 310                 315
```

```
<210> SEQ ID NO 27
<211> LENGTH: 319
<212> TYPE: PRT
<213> ORGANISM: Bacillus subtilis

<400> SEQUENCE: 27
```

Met Tyr Asn Lys Thr Val Ser Ile Asn Leu Asp Ser Arg Cys Asn Ala
1               5                   10                  15

Ser Cys Asp His Cys Cys Phe Ser Ser Pro Thr Ser Thr Thr Arg
            20                  25                  30

Met Glu Lys Glu Tyr Ile Arg Glu Leu Val Thr Glu Phe Ala Lys Asn
            35                  40                  45

Lys Thr Ile Gln Val Ile Ser Phe Thr Gly Gly Glu Val Phe Leu Asp
        50                  55                  60

Tyr Lys Phe Leu Lys Glu Leu Met Glu Ile Ile Lys Pro Tyr Glu Lys
65                  70                  75                  80

Gln Ile Thr Leu Ile Ser Asn Gly Phe Trp Gly Leu Ser Lys Lys Lys
                85                  90                  95

Val Gln Glu Tyr Phe His Asp Met Ser Ser Leu Asn Val Ile Ala Leu
            100                 105                 110

Thr Ile Ser Tyr Asp Glu Tyr His Ala Pro Phe Val Lys Ser Ser Ser
        115                 120                 125

Ile Lys Asn Ile Leu Glu His Ser Arg Lys Tyr Pro Asp Ile Asp Ile
    130                 135                 140

Ser Leu Asn Met Ala Val Thr Lys Asp Lys Met Ser Asn His Ile Leu
145                 150                 155                 160

Glu Glu Leu Gly Asp Ser Ile Leu Gly Val Lys Ile Thr Lys Phe Pro
                165                 170                 175

Met Ile Ser Val Gly Ala Ala Lys Thr Arg Ile Lys Gln Glu Asn Ile
            180                 185                 190

His Lys Phe Tyr Ser Leu Glu Asp Glu Asp Ser Leu His Cys Pro Gly
        195                 200                 205

Tyr Asp Ile Val Tyr His His Asp Gly Glu Ile Tyr Pro Cys Cys Ser
    210                 215                 220

Pro Ala Ile Phe Glu Thr Lys Ile Thr Leu Arg Glu Glu Tyr Asn Gln
225                 230                 235                 240

Ser Phe Glu Arg Thr Val Glu Lys Leu Asn Ser Asn Leu Leu Leu Phe
                245                 250                 255

Ile Leu Arg Lys Glu Gly Phe Lys Trp Phe Leu Asn Ile Leu Lys Glu
            260                 265                 270

Asn Asn Lys Ile Glu Glu Phe Asp Ile Pro Tyr Glu Phe Ser Ser Ile
        275                 280                 285

Cys Gly Val Cys Gly Ser Leu Phe Asn Ser Ala Glu Lys Ile Asn Tyr
    290                 295                 300

Phe Tyr Pro Tyr Met Glu Lys Tyr Tyr Asn Glu Asn Phe Lys Val
305                 310                 315

<210> SEQ ID NO 28
<211> LENGTH: 319
<212> TYPE: PRT
<213> ORGANISM: Bacillus subtilis

<400> SEQUENCE: 28

Met Tyr Asn Lys Thr Val Ser Ile Asn Leu Asp Ser Arg Cys Asn Ala
1               5                   10                  15

Ser Cys Asp His Cys Cys Phe Ser Ser Pro Thr Ser Thr Ile Arg
            20                  25                  30

Met Glu Lys Glu Tyr Ile Arg Glu Leu Val Thr Glu Phe Ala Lys Asn
            35                  40                  45

Lys Thr Ile Gln Val Ile Ser Phe Thr Gly Gly Glu Val Phe Leu Asp

```
            50                  55                  60
Tyr Lys Phe Leu Lys Glu Leu Met Glu Ile Ile Lys Pro Tyr Glu Lys
 65                  70                  75                  80

Gln Ile Thr Leu Ile Ser Asn Gly Phe Trp Gly Leu Ser Lys Lys Lys
                 85                  90                  95

Val Gln Glu Tyr Phe His Asp Met Asn Ser Leu Asn Val Ile Ala Leu
            100                 105                 110

Thr Ile Ser Tyr Asp Glu Tyr His Ala Pro Phe Val Lys Ser Ser Ser
            115                 120                 125

Ile Lys Asn Ile Leu Glu His Ser Arg Lys Tyr Pro Asp Ile Asp Ile
        130                 135                 140

Ser Leu Asn Met Ala Val Thr Lys Asp Lys Met Ser Asn His Ile Leu
145                 150                 155                 160

Glu Glu Leu Gly Asp Ser Ile Leu Gly Val Lys Ile Thr Lys Phe Pro
                165                 170                 175

Met Ile Ser Val Gly Ala Ala Lys Thr Arg Ile Lys Gln Glu Asn Ile
            180                 185                 190

His Lys Phe Tyr Ser Leu Glu Asp Glu Asp Ser Leu His Cys Pro Gly
        195                 200                 205

Tyr Asp Ile Val Tyr His His Asp Gly Glu Ile Tyr Pro Cys Cys Ser
210                 215                 220

Pro Ala Ile Phe Glu Thr Lys Ile Thr Leu Arg Glu Glu Tyr Asn Gln
225                 230                 235                 240

Ser Phe Glu Arg Thr Val Glu Lys Leu Asn Ser Asn Leu Leu Leu Phe
                245                 250                 255

Ile Leu Arg Lys Glu Gly Phe Lys Trp Phe Leu Asn Ile Leu Lys Glu
            260                 265                 270

Asn Asn Lys Ile Glu Glu Phe Asp Ile Pro Tyr Glu Phe Ser Ser Ile
        275                 280                 285

Cys Gly Val Cys Gly Ser Leu Phe Asn Ser Ala Glu Lys Ile Asn Tyr
    290                 295                 300

Phe Tyr Pro Tyr Met Glu Lys Tyr Tyr Asn Glu Asn Phe Lys Val
305                 310                 315

<210> SEQ ID NO 29
<211> LENGTH: 319
<212> TYPE: PRT
<213> ORGANISM: Bacillus subtilis

<400> SEQUENCE: 29

Met Tyr Asn Lys Thr Val Ser Ile Asn Leu Asp Ser Arg Cys Asn Ala
  1               5                  10                  15

Ser Cys Asp His Cys Cys Phe Ser Ser Pro Thr Ser Thr Thr Arg
             20                  25                  30

Met Glu Lys Glu Tyr Ile Arg Glu Leu Val Thr Glu Phe Ala Lys Asn
         35                  40                  45

Lys Thr Ile Gln Val Ile Ser Phe Thr Gly Gly Glu Val Phe Leu Asp
     50                  55                  60

Tyr Lys Phe Leu Lys Glu Leu Met Glu Ile Ile Lys Pro Tyr Glu Lys
 65                  70                  75                  80

Gln Ile Thr Leu Ile Ser Asn Gly Phe Trp Gly Met Ser Lys Lys Arg
                 85                  90                  95

Val Gln Glu Tyr Phe His Asp Met Asn Ser Leu Asn Val Ile Ala Leu
            100                 105                 110
```

```
Thr Ile Ser Tyr Asp Glu Tyr His Ala Pro Phe Val Lys Ser Ser Ser
            115                 120                 125

Ile Lys Asn Ile Leu Glu His Ser Arg Lys Tyr Pro Asp Ile Asp Ile
        130                 135                 140

Ser Leu Asn Met Ala Val Thr Lys Asp Lys Met Ser Asn His Ile Leu
145                 150                 155                 160

Glu Glu Leu Gly Asp Ser Ile Leu Gly Val Lys Ile Thr Lys Phe Pro
                165                 170                 175

Met Ile Ser Val Gly Ala Ala Lys Thr Arg Ile Lys Gln Glu Asn Ile
            180                 185                 190

His Lys Phe Tyr Ser Leu Glu Asp Glu Asp Ser Leu His Cys Pro Gly
        195                 200                 205

Tyr Asp Ile Val Tyr His His Asp Gly Glu Ile Tyr Pro Cys Cys Ser
    210                 215                 220

Pro Ala Ile Phe Glu Thr Lys Ile Thr Leu Arg Glu Glu Tyr Ser Gln
225                 230                 235                 240

Ser Phe Glu Arg Thr Val Glu Lys Leu Asn Ser Asn Leu Leu Leu Phe
                245                 250                 255

Ile Leu Arg Lys Glu Gly Phe Lys Trp Phe Leu Asn Ile Leu Lys Glu
            260                 265                 270

Asn Asn Lys Ile Glu Glu Phe Asp Ile Pro Tyr Glu Phe Ser Ser Ile
        275                 280                 285

Cys Gly Val Cys Gly Ser Leu Phe Asn Ser Ala Glu Lys Ile Asn Tyr
    290                 295                 300

Phe Tyr Pro Tyr Met Glu Lys Tyr Tyr Asn Glu Asn Phe Lys Val
305                 310                 315

<210> SEQ ID NO 30
<211> LENGTH: 319
<212> TYPE: PRT
<213> ORGANISM: Bacillus sp

<400> SEQUENCE: 30

Met Tyr Asn Lys Thr Val Ser Ile Asn Leu Asp Ser Arg Cys Asn Ala
1               5                   10                  15

Ser Cys Asp His Cys Cys Phe Ser Ser Pro Ser Ser Thr Thr Met
            20                  25                  30

Met Glu Lys Glu Tyr Ile Arg Glu Leu Val Thr Glu Phe Ala Lys Asn
        35                  40                  45

Lys Thr Ile Gln Val Ile Ser Phe Thr Gly Gly Glu Val Phe Leu Asp
50                  55                  60

Tyr Lys Phe Leu Lys Glu Leu Met Glu Ile Ile Lys Pro Tyr Glu Lys
65                  70                  75                  80

Gln Ile Thr Leu Ile Ser Asn Gly Phe Trp Gly Leu Ser Lys Lys Lys
                85                  90                  95

Val Gln Glu Tyr Phe His Asp Met Asn Ser Leu Asn Val Ile Ala Leu
            100                 105                 110

Thr Ile Ser Tyr Asp Glu Tyr His Ala Pro Phe Val Lys Ser Ser Ser
        115                 120                 125

Ile Lys Asn Ile Leu Glu His Ser Arg Lys Tyr Pro Asp Ile Asp Ile
    130                 135                 140

Ser Leu Asn Met Ala Val Thr Lys Asp Lys Met Ser Asn His Ile Leu
145                 150                 155                 160

Glu Glu Leu Gly Asp Ser Ile Leu Gly Val Lys Ile Thr Lys Phe Pro
                165                 170                 175
```

```
Met Ile Ser Val Gly Ala Ala Lys Thr Arg Ile Lys Gln Glu Asn Ile
            180                 185                 190

His Lys Phe Tyr Ser Leu Glu Asp Glu Asp Ser Leu His Cys Pro Gly
        195                 200                 205

Tyr Asp Ile Val Tyr His His Asp Gly Glu Ile Tyr Pro Cys Cys Ser
    210                 215                 220

Pro Ala Ile Phe Glu Thr Lys Ile Thr Leu Arg Glu Glu Tyr Asn Gln
225                 230                 235                 240

Ser Phe Glu Arg Thr Val Glu Lys Leu Asn Ser Asn Leu Leu Leu Phe
                245                 250                 255

Ile Leu Arg Lys Glu Gly Phe Lys Trp Phe Leu Asn Ile Leu Lys Glu
            260                 265                 270

Asn Asn Lys Ile Glu Glu Phe Asp Ile Pro Tyr Glu Phe Ser Ser Ile
        275                 280                 285

Cys Gly Val Cys Gly Ser Leu Phe Asn Ser Ala Glu Lys Ile Asn Tyr
    290                 295                 300

Phe Tyr Pro Tyr Met Glu Lys Tyr Tyr Asn Glu Asn Phe Lys Val
305                 310                 315

<210> SEQ ID NO 31
<211> LENGTH: 320
<212> TYPE: PRT
<213> ORGANISM: Salinibacillus aidingensis

<400> SEQUENCE: 31

Met Tyr Asn Lys Thr Val Ser Ile Asn Leu Asp Ser Arg Cys Asn Ala
1               5                   10                  15

Ser Cys Asp His Cys Cys Phe Ser Ser Pro Thr Ser Thr Thr Arg
            20                  25                  30

Met Glu Lys Glu Tyr Ile Arg Glu Leu Val Thr Glu Phe Ala Lys Asn
        35                  40                  45

Lys Thr Ile Gln Val Ile Ser Phe Thr Gly Gly Glu Val Phe Leu Asp
    50                  55                  60

Tyr Lys Phe Leu Lys Glu Leu Met Glu Ile Ile Lys Pro Tyr Glu Lys
65                  70                  75                  80

Gln Ile Thr Leu Ile Ser Asn Gly Phe Trp Gly Ile Ser Lys Lys Lys
                85                  90                  95

Val Gln Glu Tyr Phe His Asp Met Asn Ser Leu Asn Val Ile Ala Leu
            100                 105                 110

Thr Ile Ser Tyr Asp Glu Tyr His Ala Pro Phe Val Lys Pro Ser Ser
        115                 120                 125

Val Lys Arg Ile Phe Glu His Ser Arg Lys Tyr Arg Gly Ser Ile Asp
    130                 135                 140

Ile Ser Leu Asn Met Ala Val Thr Lys Asp Lys Met Ser Asn His Ile
145                 150                 155                 160

Leu Glu Glu Leu Gly Asp Ser Ile Leu Gly Val Lys Ile Thr Lys Phe
                165                 170                 175

Pro Met Ile Ser Val Gly Ala Ala Lys Asn Arg Ile Lys Gln Glu Asn
            180                 185                 190

Ile His Lys Phe Tyr Ser Leu Glu Asp Glu Asp Ser Leu His Cys Pro
        195                 200                 205

Gly Tyr Asp Ile Val Tyr His His Asp Gly Glu Ile Tyr Pro Cys Cys
    210                 215                 220

Ser Pro Ala Ile Phe Glu Thr Lys Ile Thr Leu Arg Glu Glu Tyr Asn
```

```
            225                 230                 235                 240
Gln Ser Phe Glu Arg Thr Val Glu Lys Leu Asn Ser Asn Leu Leu Leu
                245                 250                 255

Phe Ile Leu Arg Lys Glu Gly Phe Lys Trp Phe Leu Asn Ile Leu Lys
                260                 265                 270

Glu Asn Asn Lys Ile Glu Glu Phe Asp Ile Pro Tyr Glu Phe Ser Ser
                275                 280                 285

Ile Cys Gly Val Cys Gly Ser Leu Phe Asn Ser Ala Glu Lys Ile Asn
            290                 295                 300

Tyr Phe Tyr Pro Tyr Met Glu Lys Tyr Asn Glu Asn Phe Lys Val
305                 310                 315                 320

<210> SEQ ID NO 32
<211> LENGTH: 319
<212> TYPE: PRT
<213> ORGANISM: Bacillus subtilis

<400> SEQUENCE: 32

Met Tyr Asp Lys Thr Val Ser Ile Asn Leu Asp Ser Lys Cys Asn Ala
1               5                   10                  15

Ser Cys Asp His Cys Cys Phe Ser Ser Pro Thr Thr Ile Lys
            20                  25                  30

Met Glu Lys Asp Tyr Ile Arg Asp Leu Val Thr Glu Phe Ala Lys Asn
            35                  40                  45

Lys Thr Ile Gln Val Ile Ser Phe Thr Gly Gly Glu Ile Phe Leu Asp
        50                  55                  60

Tyr Ile Phe Leu Lys Glu Leu Met Glu Ile Ile Lys Pro Tyr Glu Lys
65                  70                  75                  80

Gln Ile Thr Leu Ile Ser Asn Gly Phe Trp Gly Val Ser Arg Lys Arg
                85                  90                  95

Val Gln Glu Tyr Phe Tyr Asp Met Asn Ser Leu Asn Val Val Ala Leu
            100                 105                 110

Thr Ile Ser Tyr Asp Glu Tyr His Ala Pro Phe Val Lys Ser Ser Ser
        115                 120                 125

Ile Lys Asn Ile Leu Glu His Ser Arg Lys Tyr Pro Asp Ile Asp Ile
    130                 135                 140

Ser Leu Asn Met Ala Val Thr Lys Asp Lys Met Ser Asn His Ile Leu
145                 150                 155                 160

Glu Glu Leu Gly Asp Ser Ile Leu Gly Val Lys Ile Thr Lys Phe Pro
                165                 170                 175

Met Ile Ser Val Gly Ala Ala Arg Thr Arg Ile Arg Gln Glu Asn Ile
            180                 185                 190

His Lys Phe Tyr Asn Leu Asp Asp Glu Asp Ser Leu Tyr Cys Pro Gly
        195                 200                 205

Tyr Glu Ile Val Tyr His His Asp Gly Glu Ile Tyr Pro Cys Cys Ser
    210                 215                 220

Pro Ala Ile Phe Glu Thr Lys Ile Thr Leu Arg Glu Gly Tyr Asn Gln
225                 230                 235                 240

Asn Phe Glu Arg Thr Val Glu Lys Leu Asn Ser Asn Leu Leu Leu Phe
                245                 250                 255

Ile Leu Arg Lys Glu Gly Phe Lys Trp Phe Leu Asp Ile Leu Lys Glu
                260                 265                 270

Asn Asn Lys Ile Glu Glu Phe Asp Ile Pro Tyr Glu Phe Ser Ser Ile
                275                 280                 285
```

Cys Gly Val Cys Gly Ser Leu Phe Asn Ser Ala Glu Lys Ile Asn Tyr
            290                 295                 300

Phe Tyr Pro His Met Glu Lys Tyr Tyr Tyr Glu Asn Phe Glu Val
305                 310                 315

<210> SEQ ID NO 33
<211> LENGTH: 319
<212> TYPE: PRT
<213> ORGANISM: Bacillus tequilensis

<400> SEQUENCE: 33

Met Tyr Asp Lys Thr Val Ser Ile Asn Leu Asp Ser Lys Cys Asn Ala
1               5                   10                  15

Ser Cys Asp His Cys Cys Phe Ser Ser Ser Pro Thr Ser Thr Ile Lys
            20                  25                  30

Met Glu Lys Asp Tyr Ile Arg Asp Leu Val Thr Glu Phe Ala Lys Asn
35 40 45

Lys Thr Ile Gln Val Ile Ser Phe Thr Gly Gly Glu Ile Phe Leu Asp
50 55 60

Tyr Ile Phe Leu Lys Glu Leu Met Glu Ile Ile Lys Pro Tyr Glu Lys
65 70 75 80

Gln Ile Thr Leu Ile Ser Asn Gly Phe Trp Gly Val Ser Arg Lys Arg
85 90 95

Val Gln Glu Tyr Phe Tyr Asp Met Asn Ser Leu Asn Val Val Ala Leu
100 105 110

Thr Ile Ser Tyr Asp Glu Tyr His Ala Pro Phe Val Lys Ser Ser Ser
115 120 125

Ile Lys Asn Ile Leu Glu His Ser Arg Lys Tyr Pro Asp Ile Asp Ile
130 135 140

Ser Leu Asn Met Ala Val Thr Lys Asp Lys Met Ser Asn His Ile Leu
145 150 155 160

Glu Asp Leu Gly Asp Ser Ile Leu Gly Val Lys Ile Thr Lys Phe Pro
165 170 175

Met Ile Ser Val Gly Ala Ala Arg Thr Arg Ile Arg Pro Glu Asn Ile
180 185 190

His Lys Phe His Asn Leu Asp Asp Asp Asp Ser Leu Tyr Cys Pro Gly
195 200 205

Tyr Glu Ile Val Tyr His His Asp Gly Glu Ile Tyr Pro Cys Cys Ser
210 215 220

Pro Ala Ile Phe Glu Thr Lys Ile Thr Leu Arg Glu Glu Tyr Asn Gln
225 230 235 240

Asn Phe Glu Arg Thr Val Glu Lys Leu Asn Ser Asn Leu Leu Leu Phe
245 250 255

Ile Leu Arg Lys Glu Gly Phe Lys Trp Phe Leu Asp Ile Leu Lys Glu
260 265 270

Asn Asn Lys Ile Glu Glu Phe Asp Ile Pro Tyr Glu Phe Ser Ser Ile
275 280 285

Cys Gly Val Cys Gly Ser Leu Phe Asn Ser Ala Glu Lys Ile Asn Tyr
290 295 300

Phe Tyr Pro His Met Glu Lys Tyr Tyr Tyr Glu Asn Phe Glu Val
305 310 315

<210> SEQ ID NO 34
<211> LENGTH: 320
<212> TYPE: PRT
<213> ORGANISM: Bacillus

<400> SEQUENCE: 34

```
Met Tyr Asp Lys Thr Val Ser Ile Asn Leu Asp Ser Lys Cys Asn Ala
1               5                   10                  15

Gln Cys Asp His Cys Cys Phe Ser Ser Ser Pro Thr Ser Thr Ile Lys
            20                  25                  30

Met Glu Lys Asp Tyr Ile Arg Lys Leu Val Thr Glu Phe Ala Glu Asn
        35                  40                  45

Lys Thr Ile Gln Val Ile Ser Phe Thr Gly Gly Glu Val Phe Leu Asp
    50                  55                  60

Tyr Thr Phe Leu Lys Glu Leu Met Glu Ile Ile Lys Pro Tyr Glu Lys
65                  70                  75                  80

Gln Ile Thr Leu Ile Ser Asn Gly Phe Trp Gly Ile Ser Lys Lys Lys
                85                  90                  95

Val Gln Glu Tyr Phe His Asp Met Asn Thr Leu Asn Val Val Ala Leu
            100                 105                 110

Thr Ile Ser Tyr Asp Glu Tyr His Ala Pro Phe Val Lys Pro Ser Ser
        115                 120                 125

Ile Lys Arg Ile Phe Glu His Ser Arg Lys Tyr Arg Gly Ser Ile Asp
    130                 135                 140

Ile Ser Leu Asn Met Ala Val Thr Lys Asp Lys Met Ser Asn His Ile
145                 150                 155                 160

Leu Glu Glu Leu Gly Asp Ser Ile Leu Gly Val Lys Ile Thr Lys Phe
                165                 170                 175

Pro Met Ile Ser Val Gly Ala Ala Lys Ser Arg Ile Lys Gln Glu Asn
            180                 185                 190

Ile His Lys Phe Tyr Ser Leu Glu Asp Glu Asp Ser Leu Gln Cys Pro
        195                 200                 205

Gly Tyr Asp Ile Val Tyr His His Asp Gly Glu Ile Tyr Pro Cys Cys
    210                 215                 220

Ser Pro Ala Ile Phe Glu Thr Lys Ile Thr Leu Arg Glu Asp Tyr Asn
225                 230                 235                 240

Gln Asn Phe Glu Arg Thr Val Glu Lys Leu Lys Ser Asn Leu Leu Leu
                245                 250                 255

Phe Ile Leu Arg Lys Glu Gly Phe Lys Trp Phe Leu Asp Ile Leu Lys
            260                 265                 270

Asp Asn Asn Lys Ile Glu Glu Phe Asp Ile Pro Tyr Glu Phe Ser Ser
        275                 280                 285

Ile Cys Gly Val Cys Gly Ser Leu Phe Asn Ser Val Glu Lys Ile Asn
    290                 295                 300

Tyr Phe Tyr Pro Tyr Met Glu Lys Tyr Tyr His Glu Asn Phe Glu Val
305                 310                 315                 320
```

<210> SEQ ID NO 35
<211> LENGTH: 327
<212> TYPE: PRT
<213> ORGANISM: Bacillus coagulans

<400> SEQUENCE: 35

```
Met Tyr Asn Lys Thr Val Ala Ile Asn Leu Asp Ser Lys Cys Asn Ala
1               5                   10                  15

Ser Cys Asp His Cys Cys Phe Ser Ser Ser Pro Thr Ser Glu Val Lys
            20                  25                  30

Met Glu Lys Asp Tyr Ile Arg Asn Leu Val Asn Glu Phe Ala Arg Ser
        35                  40                  45
```

Lys Thr Ile Glu Val Ile Ser Phe Thr Gly Gly Glu Ile Phe Leu Asp
            50                  55                  60

Tyr Lys Phe Leu Lys Glu Leu Met Glu Ile Ile Lys Pro Tyr Lys Lys
65                  70                  75                  80

Gln Ile Thr Leu Ile Ser Asn Gly Phe Trp Gly Gly Ser Gln Asn Lys
            85                  90                  95

Val Glu Glu Tyr Phe Lys Asp Met Asn Ser Leu Asn Val Val Ala Leu
            100                 105                 110

Thr Ile Ser Tyr Asp Glu Tyr His Ala Pro Phe Val Lys Leu Ser Ser
            115                 120                 125

Val Lys Arg Ile Phe Glu His Ser Arg Lys Tyr Pro Asp Ile Asp Val
            130                 135                 140

Ser Leu Asn Met Ala Val Thr Lys Asp Lys Met Ser Asn Arg Ile Leu
145                 150                 155                 160

Glu Glu Leu Gly Asp Ser Ile Leu Gly Ile Lys Ile Thr Lys Phe Pro
            165                 170                 175

Leu Ile Pro Val Gly Ala Ala Lys Asn Arg Ile Ser Gln Glu Asn Ile
            180                 185                 190

His Lys Phe Tyr Asn Leu Asp Asp Glu Asp Ser Leu Gln Cys Pro Gly
            195                 200                 205

Tyr Glu Ile Val Tyr His His Asp Gly Glu Ile Tyr Pro Cys Cys Ser
            210                 215                 220

Pro Ala Ile Phe Glu Thr Lys Ile Thr Leu Arg Glu Glu Tyr Ser Gln
225                 230                 235                 240

Thr Tyr Glu Arg Thr Val Glu Lys Leu Gln Ser Asn Leu Leu Phe
            245                 250                 255

Ile Ile Arg Lys Glu Gly Phe Lys Trp Phe Leu Asn Ile Leu Lys Glu
            260                 265                 270

Asn Lys Lys Ile Glu Glu Phe Gly Ile Pro Tyr Glu Phe Ser Ser Ile
            275                 280                 285

Cys Ser Leu Cys Val Ser Leu Phe Asn Ser Glu Asp Lys Ile Asn Tyr
            290                 295                 300

Phe His Asn Phe Met Glu Asp Tyr Tyr Tyr Ala Asn Tyr Gly Asn Lys
305                 310                 315                 320

Asp His Glu Thr Ala Lys Ile
            325

<210> SEQ ID NO 36
<211> LENGTH: 319
<212> TYPE: PRT
<213> ORGANISM: Staphylococcus equorum

<400> SEQUENCE: 36

Met Tyr Ile Asn Ser Val Ser Ile Asn Leu Asp Ser Lys Cys Asn Ala
1               5                   10                  15

Ala Cys Asp His Cys Cys Phe Ser Cys Ser Pro Gln Ser Thr Ile Lys
            20                  25                  30

Met Glu Asp Ser Tyr Ile Arg Lys Gln Val Leu Glu Phe Ser Lys Asn
            35                  40                  45

Pro Asn Ile Lys Val Ile Ser Phe Thr Gly Gly Glu Ile Phe Leu Asn
            50                  55                  60

Tyr Gln Phe Leu Glu Glu Leu Leu Lys Ile Thr Lys Phe Tyr Asn Lys
65                  70                  75                  80

Lys Ile Thr Leu Ile Ser Asn Gly Phe Trp Gly Ala Ser Arg Arg Leu 85                  90                  95
Leu Arg Lys Tyr Phe Glu Asp Phe Gln Lys Tyr Asn Val Val Ala Leu
            100                 105                 110

Thr Ile Ser Tyr Asp Glu Tyr His Ser Pro Tyr Val Lys Ile Lys Ser
            115                 120                 125

Ile Lys Asn Ile Phe Asp Tyr Arg Met Lys Tyr Pro Glu Ile Glu Val
        130                 135                 140

Ser Leu Asn Met Ala Val Thr Lys Glu Lys Met Ser Asp Asn Ile Leu
145                 150                 155                 160

Arg Glu Leu Gly Ser Ser Val Leu Gly Ile Lys Ile Thr Lys Phe Pro
                165                 170                 175

Met Ile Thr Val Gly Ala Ala Lys Lys Asn Ile Ala Lys Glu Asn Ile
            180                 185                 190

His Asn Phe Tyr Asn Val Glu Lys Asp Lys Ser Ile Leu Tyr Cys Pro
        195                 200                 205

Gly Tyr Glu Leu Val Tyr His His Asp Gly Glu Ile Tyr Pro Cys Cys
    210                 215                 220

Ser Pro Ala Ile Phe Glu Thr Ser Ile Thr Leu Arg Glu Ser Glu Asn
225                 230                 235                 240

Gln Thr Phe Glu Arg Thr Ile Glu Lys Leu Asn Ser Asn Leu Leu Leu
                245                 250                 255

Tyr Ile Ile Arg Lys Glu Gly Phe Asn Trp Phe Ile Lys Ile Leu Lys
            260                 265                 270

Asn Asn Asn Leu Met Asp Ser Phe Glu Ile Pro Glu Asp Phe Pro Ser
        275                 280                 285

Val Cys Ser Val Cys Gly Ser Leu Phe Asn Ser Glu Glu Lys Ile Glu
    290                 295                 300

Phe Phe Lys Pro Tyr Met Glu Lys Tyr Tyr Glu Asn Phe Glu Ile
305                 310                 315

<210> SEQ ID NO 37
<211> LENGTH: 320
<212> TYPE: PRT
<213> ORGANISM: Staphylococcus pseudintermedius

<400> SEQUENCE: 37

Met Tyr Asp Lys Ser Val Ser Ile Asn Leu Thr Ser Lys Cys Asn Ala
1               5                   10                  15

Thr Cys Asp His Cys Cys Phe Ser Cys Ser Pro Lys Ser Thr Ile Lys
            20                  25                  30

Met Glu Asp Phe Tyr Ile Arg Glu Thr Val Leu Glu Phe Ala Lys Asp
        35                  40                  45

Ser Asn Val Glu Val Ile Ser Phe Thr Gly Gly Glu Ile Phe Leu Asn
    50                  55                  60

Tyr Glu Phe Leu Glu Glu Leu Leu Lys Ile Thr Lys Asn Tyr Asn Lys
65                  70                  75                  80

Lys Val Thr Leu Ile Ser Asn Gly Phe Trp Gly Asn Ser Arg Lys Leu
                85                  90                  95

Leu Glu Lys Tyr Phe Ser Asp Phe Tyr Lys Tyr Asn Val Val Ala Leu
            100                 105                 110

Thr Ile Ser Tyr Asp Glu Tyr His Ser Pro Phe Val Lys Leu Lys Ser
            115                 120                 125

Ile Lys Asn Ile Phe Glu Tyr Arg Met Lys Tyr Pro Glu Ile Gln Val
        130                 135                 140

```
Ser Leu Asn Met Ala Val Thr Lys Asp Lys Met Ser Asp Asn Ile Leu
145                 150                 155                 160

Arg Glu Leu Gly Ser Ser Ile Leu Gly Ala Lys Ile Thr Lys Phe Pro
            165                 170                 175

Met Ile Ser Val Gly Ala Ala Lys Asp Lys Ile Ser Lys Glu Asn Ile
                180                 185                 190

His Asn Phe Tyr Asn Ile Asn Lys Asp Arg Glu Val Leu Tyr Cys Pro
            195                 200                 205

Gly Phe Glu Ile Val Tyr His His Asp Gly Glu Ile Tyr Pro Cys Cys
    210                 215                 220

Ser Pro Ala Ile Phe Glu Thr Pro Ile Thr Leu Arg Glu Asn Lys Asn
225                 230                 235                 240

Gln Thr Leu Thr Arg Thr Val Glu Lys Leu Asn Ser Asn Leu Leu Leu
                245                 250                 255

Tyr Ile Ile Arg Lys Glu Gly Phe Asn Trp Phe Leu Asp Ile Leu Arg
                260                 265                 270

Glu Glu Asn Met Leu His Gln Phe Asp Ile Pro Thr Asp Phe Pro Ser
            275                 280                 285

Val Cys Ser Ile Cys Gly Ser Leu Phe Ser Thr Glu Glu Lys Ile Lys
    290                 295                 300

Phe Phe Lys Pro Phe Met Glu Ala Tyr Tyr Tyr Glu Thr Ile Glu Val
305                 310                 315                 320

<210> SEQ ID NO 38
<211> LENGTH: 320
<212> TYPE: PRT
<213> ORGANISM: Staphylococcus epidermidis

<400> SEQUENCE: 38

Met Tyr Gly Lys Ser Val Ser Ile Asn Leu Asn Ser Lys Cys Asn Ala
1               5                   10                  15

Met Cys Asp His Cys Cys Phe Ser Cys Ser Pro Lys Ser Thr Ile Lys
                20                  25                  30

Met Lys Asp Ser Tyr Ile Lys Asp Thr Val Leu Glu Phe Ser Lys Asn
            35                  40                  45

Pro Asn Ile Glu Ile Ile Ser Phe Thr Gly Gly Glu Ile Phe Leu Asn
        50                  55                  60

Tyr Lys Phe Leu Glu Glu Leu Leu Ile Ile Thr Lys Ser Tyr Asn Lys
65                  70                  75                  80

Lys Val Thr Leu Ile Ser Asn Gly Phe Trp Gly Ser Ser Arg Lys Leu
                85                  90                  95

Leu Arg Lys Phe Phe Asp Asp Phe Lys Lys Tyr Asn Val Ile Ala Leu
            100                 105                 110

Thr Ile Ser Tyr Asp Glu Tyr His Glu Pro Phe Ile Lys Leu Lys Ser
        115                 120                 125

Val Lys Asn Ile Phe Glu Tyr Arg Met Lys Tyr Pro Glu Ile Glu Val
    130                 135                 140

Ser Leu Asn Met Ala Val Thr Lys Asp Lys Met Ser Asp Asn Ile Leu
145                 150                 155                 160

Ser Glu Leu Gly Ser Ser Ile Leu Gly Ile Lys Ile Thr Lys Phe Pro
            165                 170                 175

Met Ile Thr Val Gly Ser Ala Lys Asn Lys Ile Ser Lys Asn Asn Ile
                180                 185                 190

His Asn Phe Tyr Asn Ile Glu Lys Asp Lys Asn Leu Leu Phe Cys Pro
            195                 200                 205
```

Gly Tyr Glu Ile Val Tyr His His Asp Gly Glu Ile Tyr Pro Cys Cys
210                 215                 220

Ser Pro Ala Ile Phe Glu Thr Lys Ile Ser Leu Arg Glu Asp Lys Tyr
225                 230                 235                 240

Gln Thr Leu Glu Arg Thr Ile Glu Lys Leu Asn Ser Asn Leu Leu Leu
            245                 250                 255

Tyr Ile Val Arg Lys Glu Gly Phe Asn Trp Phe Leu Asp Ile Val Arg
            260                 265                 270

Glu Gln Asp Leu Leu Asn Glu Phe Glu Ile Pro Lys Asp Phe Pro Ser
        275                 280                 285

Val Cys Ser Ile Cys Gly Asn Leu Phe Asn Thr Glu Glu Lys Ile Asn
        290                 295                 300

Phe Phe Lys Pro Tyr Met Lys Glu Tyr Tyr Glu Thr Ile Lys Val
305                 310                 315                 320

<210> SEQ ID NO 39
<211> LENGTH: 315
<212> TYPE: PRT
<213> ORGANISM: Paenibacillus sp

<400> SEQUENCE: 39

Met Tyr Asn Asn Ala Val Ile Asn Leu Gly Ala Lys Cys Asn Ala Ala
1               5                   10                  15

Cys Ala His Cys Cys Phe Ser Cys Ser Pro Ala Ser Thr Gln Ser Met
            20                  25                  30

Glu Pro Asn Tyr Ile Arg Gln Leu Ala His Glu Leu Ala Glu Asn Lys
        35                  40                  45

Lys Val Asn Leu Ile Ser Phe Thr Gly Gly Glu Ile Phe Leu Asn Tyr
50                  55                  60

Pro Phe Leu Gln Glu Leu Leu Glu Ile Ile Lys Pro His Gln Lys Arg
65                  70                  75                  80

Ile Thr Leu Ile Ser Asn Gly Phe Trp Gly Met Ser Arg Lys Lys Thr
                85                  90                  95

Glu Gln Tyr Phe Asn Asp Met Glu Tyr Tyr Asn Val Thr Asn Leu Thr
            100                 105                 110

Ile Ser Tyr Asp Glu Phe His Glu Pro Tyr Val Lys Ala Asp Ala Ile
        115                 120                 125

Lys Asn Ile Leu Glu Cys Ser Arg Asp Phe Ser Asn Thr Ser Val Ala
130                 135                 140

Leu Asn Met Ala Val Thr Lys Ser Lys Met Ser Asn Arg Ile Leu Glu
145                 150                 155                 160

Tyr Met Gly Glu Ser Leu Leu Gly Ile Arg Val Thr Lys Phe Pro Leu
                165                 170                 175

Met Pro Val Gly Glu Ala Lys His Glu Glu Pro Asp Ser Phe Gln His
            180                 185                 190

Ile Tyr Lys Leu Ser Asn Glu Arg Ser Leu His Cys Pro Gly Phe Glu
        195                 200                 205

Val Val Tyr His Phe Asp Gly Gln Ile Tyr Pro Cys Cys Ser Pro Ala
210                 215                 220

Val Phe Asp Thr Lys Leu His Leu Arg Glu Ser Met Asp Gln Thr Phe
225                 230                 235                 240

Asp Arg Thr Ile Glu Lys Leu Asn Ala Asn Leu Leu Phe Tyr Ile Met
                245                 250                 255

Arg Lys Glu Gly Phe Lys Trp Phe Ile Asp Ile Val Gln Ser Asn Pro

```
                    260                 265                 270
Glu Phe Asn His Ile Lys Ile Pro Glu Gln Phe Ser Ser Ile Cys Asn
            275                 280                 285

Ile Cys Asn Ile Leu Phe Lys Thr Glu Glu Asn Ile Asp Leu Leu Thr
        290                 295                 300

Pro Tyr Met Met Asn Tyr Tyr Glu Asn Met Val
305                 310                 315

<210> SEQ ID NO 40
<211> LENGTH: 335
<212> TYPE: PRT
<213> ORGANISM: Paenibacillus sp

<400> SEQUENCE: 40

Met Tyr Lys Ile Thr Leu Leu His Leu Thr Ser Phe Lys Asn Gly Arg
1               5                   10                  15

Lys Glu Met Phe Met Tyr Asn Asn Ala Val Ile Asn Leu Gly Ala Lys
            20                  25                  30

Cys Asn Ala Ala Cys Ala His Cys Cys Phe Ser Cys Ser Pro Ala Ser
        35                  40                  45

Thr Gln Ser Met Glu Pro Asn Tyr Ile Arg Gln Leu Ala His Glu Leu
    50                  55                  60

Ala Glu Asn Lys Lys Val Asn Leu Ile Ser Phe Thr Gly Gly Glu Ile
65                  70                  75                  80

Phe Leu Asn Tyr Pro Phe Leu Gln Glu Leu Leu Glu Ile Ile Lys Pro
                85                  90                  95

His Gln Lys Arg Ile Thr Leu Ile Ser Asn Gly Phe Trp Gly Met Ser
            100                 105                 110

Arg Lys Lys Thr Glu Gln Tyr Phe Asn Asp Met Glu Tyr Tyr Asn Val
        115                 120                 125

Thr Asn Leu Thr Ile Ser Tyr Asp Glu Phe His Glu Pro Tyr Val Lys
    130                 135                 140

Ala Asp Ala Ile Lys Asn Ile Leu Glu Cys Ser Arg Asp Phe Ser Asn
145                 150                 155                 160

Thr Ser Val Ala Leu Asn Met Ala Val Thr Lys Ser Lys Met Ser Asn
                165                 170                 175

Arg Ile Leu Glu Tyr Met Gly Glu Ser Leu Leu Gly Ile Arg Val Thr
            180                 185                 190

Lys Phe Pro Leu Met Pro Val Gly Glu Ala Lys His Glu Glu Pro Asp
        195                 200                 205

Ser Phe Gln His Ile Tyr Lys Leu Ser Asn Glu Arg Ser Leu His Cys
    210                 215                 220

Pro Gly Phe Glu Val Val Tyr His Phe Asp Gly Gln Ile Tyr Pro Cys
225                 230                 235                 240

Cys Ser Pro Ala Val Phe Asp Thr Lys Leu His Leu Arg Glu Ser Met
                245                 250                 255

Asp Gln Thr Phe Asp Arg Thr Ile Glu Lys Leu Asn Ala Asn Leu Leu
            260                 265                 270

Phe Tyr Ile Met Arg Lys Glu Gly Phe Lys Trp Phe Ile Asp Ile Val
        275                 280                 285

Gln Ser Asn Pro Glu Phe Asn His Ile Lys Ile Pro Glu Gln Phe Ser
    290                 295                 300

Ser Ile Cys Asn Ile Cys Asn Ile Leu Phe Lys Thr Glu Glu Asn Ile
305                 310                 315                 320
```

Asp Leu Leu Thr Pro Tyr Met Met Asn Tyr Tyr Glu Asn Met Val
            325                 330                 335

<210> SEQ ID NO 41
<211> LENGTH: 335
<212> TYPE: PRT
<213> ORGANISM: Enterococcus caccae

<400> SEQUENCE: 41

Met Tyr Glu Ile Thr Leu Leu His Leu Thr Ser Phe Lys Asn Gly Arg
1               5                   10                  15

Lys Glu Met Phe Met Tyr Asn Asn Ala Val Ile Asn Leu Gly Ala Lys
            20                  25                  30

Cys Asn Ala Ala Cys Ala His Cys Cys Phe Ser Cys Ser Pro Ala Ser
        35                  40                  45

Thr Gln Ser Met Glu Pro Asn Tyr Ile Arg Gln Leu Ala His Glu Leu
    50                  55                  60

Ala Glu Asn Lys Lys Val Asn Leu Ile Ser Phe Thr Gly Gly Glu Ile
65                  70                  75                  80

Phe Leu Asn Tyr Pro Phe Leu Gln Glu Leu Leu Glu Ile Ile Lys Pro
                85                  90                  95

His Gln Lys Arg Ile Thr Leu Ile Ser Asn Gly Phe Trp Gly Met Ser
            100                 105                 110

Arg Lys Lys Thr Glu Gln Tyr Phe Asn Asp Met Glu Tyr Tyr Asn Val
        115                 120                 125

Thr Asn Leu Thr Ile Ser Tyr Asp Glu Phe His Glu Pro Tyr Val Lys
    130                 135                 140

Ala Asp Ala Ile Lys Asn Ile Leu Glu Cys Ser Arg Asp Phe Ser Asn
145                 150                 155                 160

Thr Ser Val Ala Leu Asn Met Ala Val Thr Lys Ser Lys Met Ser Asn
                165                 170                 175

Arg Ile Leu Glu Tyr Met Gly Glu Ser Leu Leu Gly Ile Arg Val Thr
            180                 185                 190

Lys Phe Pro Leu Met Pro Val Gly Glu Ala Lys His Glu Glu Pro Asp
        195                 200                 205

Ser Phe Gln His Ile Tyr Lys Leu Ser Asn Glu Arg Ser Leu His Cys
    210                 215                 220

Pro Gly Phe Glu Val Val Tyr His Phe Asp Gly Gln Ile Tyr Pro Cys
225                 230                 235                 240

Cys Ser Pro Ala Val Phe Asp Thr Lys Leu His Leu Arg Glu Ser Met
                245                 250                 255

Asp Gln Thr Phe Asp Arg Thr Ile Glu Lys Leu Asn Ala Asn Leu Leu
            260                 265                 270

Phe Tyr Ile Met Arg Lys Glu Gly Phe Lys Trp Phe Ile Asp Ile Val
        275                 280                 285

Gln Ser Asn Pro Glu Phe Asn His Ile Lys Ile Pro Glu Gln Phe Ser
    290                 295                 300

Ser Ile Cys Asn Ile Cys Asn Ile Leu Phe Lys Thr Glu Glu Asn Ile
305                 310                 315                 320

Asp Leu Leu Thr Pro Tyr Met Met Asn Tyr Tyr Glu Asn Met Val
                325                 330                 335

<210> SEQ ID NO 42
<211> LENGTH: 315
<212> TYPE: PRT
<213> ORGANISM: Enterococcus faecalis

<400> SEQUENCE: 42

```
Met Tyr Glu Ser Val Val Ile Asn Leu Gly Ala Arg Cys Asn Ala Thr
1               5                   10                  15

Cys Glu His Cys Cys Phe Ser Cys Ser Pro Ser Lys Lys Thr Ser Met
            20                  25                  30

Glu Lys Ser Glu Ile Ile Glu Leu Val Lys Ser Phe Ser Asn Asn Leu
        35                  40                  45

Lys Ile Lys Val Ile Ser Phe Thr Gly Gly Glu Ile Phe Leu Asn Tyr
    50                  55                  60

Ser Phe Leu Lys Glu Leu Leu Glu Ile Val His Ser Cys Gly Lys Lys
65                  70                  75                  80

Ser Thr Leu Ile Ser Asn Gly Phe Trp Gly Ala Asn Val Glu Lys Val
                85                  90                  95

Lys Ile Tyr Phe Lys Asp Met Lys Glu Leu Gly Val Thr Asn Leu Ser
            100                 105                 110

Ile Ser His Asp Asp Phe His Ala Lys Phe Val Lys Thr Asp Cys Ile
        115                 120                 125

Lys Asn Ile Leu Glu Glu Ser Arg Lys Tyr Pro Ser Ile Arg Val Val
    130                 135                 140

Val Asn Ile Ala Val Ser Lys Ser Asn Met Gly Asn Lys Val Ile Glu
145                 150                 155                 160

Glu Leu Asp Glu Ala Ala Leu Gly Ile Pro Leu Thr Lys Tyr Pro Leu
                165                 170                 175

Ile Ala Val Gly Glu Ala Glu Asn Met Ala Asp Ser Glu Phe Gln Lys
            180                 185                 190

Ile Tyr Ser Ile Asp Asn Leu Glu Gln Leu Glu Cys Pro Gly Tyr Glu
        195                 200                 205

Pro Val Tyr His Phe Asp Gly Asn Val Tyr Pro Cys Cys Ser Pro Ala
    210                 215                 220

Val Phe Asp Thr Ala Leu Ile Leu Asn Asp Arg Ala Cys Gln Ser Phe
225                 230                 235                 240

Asp Lys Thr Ile Glu Lys Met Asn Ala Asn Leu Leu Leu Tyr Ile Met
                245                 250                 255

Arg Lys Glu Gly Phe Arg Trp Phe Ile Glu Ile Val Met Ser Asn Gln
            260                 265                 270

Glu Phe Ser His Ile Gln Ile Glu Glu His Phe Ser Ser Ile Cys Thr
        275                 280                 285

Ile Cys Arg Gln Leu Phe Lys Ser Glu Glu Asn Ile Lys Leu Phe Thr
    290                 295                 300

Pro Tyr Met Arg Glu Tyr Tyr Glu Gln Met Leu
305                 310                 315
```

<210> SEQ ID NO 43
<211> LENGTH: 318
<212> TYPE: PRT
<213> ORGANISM: Enterococcus faecalis

<400> SEQUENCE: 43

```
Met Asn Leu Leu Tyr Glu Ser Val Val Asn Leu Gly Ala Arg Cys
1               5                   10                  15

Asn Ala Ser Cys Glu His Cys Cys Phe Ser Cys Ser Pro Thr Lys Lys
            20                  25                  30

Glu Ala Leu Asp Lys Asn Glu Val Ile Asn Leu Val Glu Asn Phe Ser
        35                  40                  45
```

```
Asn Asn Pro Lys Ile Lys Thr Ile Ser Phe Thr Gly Gly Glu Ile Phe
         50                  55                  60

Leu Asn Tyr Pro Phe Leu Tyr Ser Leu Leu Lys Ile Val Asn Ser Ser
 65                  70                  75                  80

Gly Lys Ile Ser Thr Leu Ile Ser Asn Gly Phe Trp Gly Arg Glu Ile
                 85                  90                  95

Glu Thr Val Lys Lys Tyr Phe Leu Asp Met Asn Arg Met Gly Val Thr
            100                 105                 110

Asn Leu Ser Ile Ser His Asp Asp Phe His Ser Lys Phe Ile Lys Thr
        115                 120                 125

Asp Tyr Ile Arg Asn Ile Leu Ile Glu Ser Arg Lys Tyr Pro Asp Ile
    130                 135                 140

Gln Ile Thr Val Asn Ile Ala Val Ser Lys Asn Ser Thr Gly Asp Lys
145                 150                 155                 160

Ile Ile His Asp Leu Gly Glu Ala Ile Leu Gly Ile Pro Val Thr Lys
                165                 170                 175

Phe Pro Leu Ile Pro Val Gly Glu Ala Lys Asn Ile Asn Asp Asp Glu
            180                 185                 190

Phe Gln Asn Ile Tyr Ser Leu Ser His Pro Asn Gln Leu Lys Cys Pro
        195                 200                 205

Gly Phe Glu Pro Val Tyr His Phe Asn Gly Asn Val Tyr Pro Cys Cys
    210                 215                 220

Ser Pro Ala Ile Phe Asp Thr Ala Leu Ile Leu Asn Asp Glu Leu Tyr
225                 230                 235                 240

Gln Asp Phe Asp Lys Thr Ile Thr Lys Met Asn Ser Asn Leu Leu Leu
                245                 250                 255

Tyr Ile Met Arg Arg Glu Gly Phe Ser Trp Phe Ile Asn Ile Val Ser
            260                 265                 270

Asn Asn Asn Glu Phe Ser His Ile Lys Ile Asn Lys Glu Phe Ser Ser
        275                 280                 285

Ile Cys Ser Ile Cys Arg Gln Leu Phe Lys Thr Glu Asn Asn Ile Lys
    290                 295                 300

Leu Leu Thr Pro Tyr Met Arg Lys Tyr Tyr Glu Gln Met Leu
305                 310                 315

<210> SEQ ID NO 44
<211> LENGTH: 315
<212> TYPE: PRT
<213> ORGANISM: Enterococcus faecalis

<400> SEQUENCE: 44

Met Tyr Asp Ser Val Val Val Asn Leu Gly Ala Arg Cys Asn Ala Ser
 1               5                  10                  15

Cys Glu His Cys Cys Phe Ser Cys Ser Pro Thr Lys Lys Glu Ala Leu
                20                  25                  30

Asp Lys Lys Glu Val Ile Asn Leu Val Glu Asn Phe Ser Asn Asn Pro
            35                  40                  45

Lys Ile Lys Thr Ile Ser Phe Thr Gly Gly Glu Ile Phe Leu Asn Tyr
         50                  55                  60

Pro Phe Leu Tyr Asn Leu Leu Lys Ile Val Asn Ser Ser Gly Lys Ile
 65                  70                  75                  80

Ser Thr Leu Ile Ser Asn Gly Phe Trp Gly Arg Glu Ile Glu Thr Val
                 85                  90                  95

Lys Lys Tyr Phe Leu Asp Met Asn Arg Met Gly Val Thr Asn Leu Ser
```

```
                100             105             110
Ile Ser His Asp Asp Phe His Ser Lys Phe Ile Lys Thr Asp Tyr Ile
            115                 120                 125
Arg Asn Ile Leu Ile Glu Ser Arg Lys Tyr Pro Asp Ile Gln Ile Thr
            130                 135                 140
Val Asn Ile Ala Val Ser Lys Asn Ser Thr Gly Asp Lys Ile Ile His
145                 150                 155                 160
Asp Leu Gly Glu Ala Ile Leu Gly Ile Pro Val Thr Lys Phe Pro Leu
                165                 170                 175
Ile Pro Val Gly Glu Ala Lys Asn Ile Asn Asp Asp Glu Phe Gln Asn
                180                 185                 190
Ile Tyr Ser Leu Ser His Pro Asn Gln Leu Lys Cys Pro Gly Phe Glu
                195                 200                 205
Pro Val Tyr His Phe Asn Gly Asn Val Tyr Pro Cys Cys Ser Pro Ala
                210                 215                 220
Ile Phe Asp Thr Ala Leu Ile Leu Asn Asp Glu Leu Tyr Gln Glu Phe
225                 230                 235                 240
Asp Lys Thr Ile Thr Lys Met Asn Ser Asn Leu Leu Leu Tyr Ile Met
                245                 250                 255
Arg Arg Glu Gly Phe Ser Trp Phe Ile Asn Ile Val Ser Asn Asn Asn
                260                 265                 270
Glu Phe Ser His Ile Lys Ile Asn Lys Glu Phe Ser Ser Ile Cys Ser
                275                 280                 285
Ile Cys Arg Gln Leu Phe Lys Thr Glu Asn Asn Ile Lys Leu Leu Thr
                290                 295                 300
Pro Tyr Met Arg Lys Tyr Tyr Glu Gln Met Leu
305                 310                 315

<210> SEQ ID NO 45
<211> LENGTH: 315
<212> TYPE: PRT
<213> ORGANISM: Enterococcus faecalis

<400> SEQUENCE: 45

Met Tyr Asp Ser Val Val Asn Leu Gly Ala Arg Cys Asn Ala Ser
1               5                   10                  15
Cys Glu His Cys Cys Phe Ser Cys Ser Pro Thr Lys Lys Glu Ala Leu
                20                  25                  30
Asp Lys Asn Glu Val Ile Asn Leu Val Glu Asn Phe Ser Asn Asn Pro
            35                  40                  45
Lys Ile Lys Thr Ile Ser Phe Thr Gly Gly Glu Ile Phe Leu Asn Tyr
            50                  55                  60
Pro Phe Leu Tyr Asn Leu Leu Lys Ile Val Asn Ser Ser Gly Lys Ile
65                  70                  75                  80
Ser Thr Leu Ile Ser Asn Gly Phe Trp Gly Arg Glu Ile Glu Thr Val
                85                  90                  95
Lys Lys Tyr Phe Leu Asp Met Asn Arg Met Gly Val Thr Asn Leu Ser
                100                 105                 110
Ile Ser His Asp Asp Phe His Ser Lys Phe Ile Lys Thr Asp Tyr Ile
            115                 120                 125
Arg Asn Ile Leu Ile Glu Ser Arg Lys Tyr Pro Asp Ile Gln Ile Thr
            130                 135                 140
Val Asn Ile Ala Val Ser Lys Asn Ser Thr Gly Asp Lys Ile Ile His
145                 150                 155                 160
```

```
Asp Leu Gly Glu Ala Ile Leu Gly Ile Pro Val Thr Lys Phe Pro Leu
            165                 170                 175

Ile Pro Val Gly Glu Ala Lys Asn Ile Asn Asp Asp Glu Phe Gln Asn
        180                 185                 190

Ile Tyr Ser Leu Ser His Pro Asn Gln Leu Lys Cys Pro Gly Phe Glu
    195                 200                 205

Pro Val Tyr His Phe Asn Gly Asn Val Tyr Pro Cys Cys Ser Pro Ala
210                 215                 220

Ile Phe Asp Thr Ala Leu Ile Leu Asn Asp Glu Leu Tyr Gln Glu Phe
225                 230                 235                 240

Asp Lys Thr Ile Thr Lys Met Asn Ser Asn Leu Leu Leu Tyr Ile Met
                245                 250                 255

Arg Arg Glu Gly Phe Ser Trp Phe Ile Asn Ile Val Ser Asn Asn Asn
            260                 265                 270

Glu Phe Ser His Ile Lys Ile Asn Lys Glu Phe Ser Ser Ile Cys Ser
        275                 280                 285

Ile Cys Arg Gln Leu Phe Lys Thr Glu Asn Asn Ile Lys Leu Leu Thr
    290                 295                 300

Pro Tyr Met Arg Lys Tyr Tyr Glu Gln Met Leu
305                 310                 315

<210> SEQ ID NO 46
<211> LENGTH: 315
<212> TYPE: PRT
<213> ORGANISM: Enterococcus faecalis

<400> SEQUENCE: 46

Met Tyr Glu Ser Val Val Asn Leu Gly Ala Arg Cys Asn Ala Ser
1               5                   10                  15

Cys Glu His Cys Cys Phe Ser Cys Ser Pro Thr Lys Lys Glu Ala Leu
            20                  25                  30

Asp Lys Asn Glu Val Ile Asn Leu Val Glu Asn Phe Ser Asn Pro
        35                  40                  45

Lys Ile Lys Thr Ile Ser Phe Thr Gly Gly Glu Ile Phe Leu Asn Tyr
    50                  55                  60

Pro Phe Leu Tyr Ser Leu Leu Lys Ile Val Asn Ser Ser Gly Lys Ile
65                  70                  75                  80

Ser Thr Leu Ile Ser Asn Gly Phe Trp Gly Arg Glu Ile Glu Thr Val
                85                  90                  95

Lys Lys Tyr Phe Leu Asp Met Asn Arg Met Gly Val Thr Asn Leu Ser
            100                 105                 110

Ile Ser His Asp Asp Phe His Ser Lys Phe Ile Lys Thr Asp Tyr Ile
        115                 120                 125

Arg Asn Ile Leu Ile Glu Ser Arg Lys Tyr Pro Asp Ile Gln Ile Thr
    130                 135                 140

Val Asn Ile Ala Val Ser Lys Asn Ser Thr Gly Asp Lys Ile Ile His
145                 150                 155                 160

Asp Leu Gly Glu Ala Ile Leu Gly Ile Pro Val Thr Lys Phe Pro Leu
                165                 170                 175

Ile Pro Val Gly Glu Ala Lys Asn Ile Asn Asp Asp Glu Phe Gln Asn
            180                 185                 190

Ile Tyr Ser Leu Ser His Pro Asn Gln Leu Lys Cys Pro Gly Phe Glu
        195                 200                 205

Pro Val Tyr His Phe Asn Gly Asn Val Tyr Pro Cys Cys Ser Pro Ala
    210                 215                 220
```

```
Ile Phe Asp Thr Ala Leu Ile Leu Asn Asp Glu Leu Tyr Gln Asp Phe
225                 230                 235                 240

Asp Lys Thr Ile Thr Lys Met Asn Ser Asn Leu Leu Leu Tyr Ile Met
            245                 250                 255

Arg Arg Glu Gly Phe Ser Trp Phe Ile Asn Ile Val Ser Asn Asn Asn
        260                 265                 270

Glu Phe Ser His Ile Lys Ile Asn Lys Glu Phe Ser Ser Ile Cys Ser
            275                 280                 285

Ile Cys Arg Gln Leu Phe Lys Thr Glu Asn Asn Ile Lys Leu Leu Thr
        290                 295                 300

Pro Tyr Met Arg Lys Tyr Tyr Glu Gln Met Leu
305                 310                 315

<210> SEQ ID NO 47
<211> LENGTH: 322
<212> TYPE: PRT
<213> ORGANISM: Enterococcus faecalis

<400> SEQUENCE: 47

Met Lys Glu Gly Val Asn Leu Leu Tyr Glu Ser Val Val Asn Leu
1               5                   10                  15

Gly Ala Arg Cys Asn Ala Ser Cys Glu His Cys Cys Phe Ser Cys Ser
            20                  25                  30

Pro Thr Lys Lys Glu Ala Leu Asp Lys Asn Glu Val Ile Asn Leu Val
            35                  40                  45

Glu Asn Phe Ser Asn Asn Pro Lys Ile Lys Thr Ile Ser Phe Thr Gly
50                  55                  60

Gly Glu Ile Phe Leu Asn Tyr Pro Phe Tyr Ser Leu Leu Lys Ile
65                  70                  75                  80

Val Asn Ser Ser Gly Lys Ile Ser Thr Leu Ile Ser Asn Gly Phe Trp
                85                  90                  95

Gly Arg Glu Ile Glu Thr Val Lys Lys Tyr Phe Leu Asp Met Asn Arg
            100                 105                 110

Met Gly Val Thr Asn Leu Ser Ile Ser His Asp Asp Phe His Ser Lys
            115                 120                 125

Phe Ile Lys Thr Asp Tyr Ile Arg Asn Ile Leu Ile Glu Ser Arg Lys
130                 135                 140

Tyr Pro Asp Ile Gln Ile Thr Val Asn Ile Ala Val Ser Lys Asn Ser
145                 150                 155                 160

Thr Gly Asp Lys Ile Ile His Asp Leu Gly Glu Ala Ile Leu Gly Ile
                165                 170                 175

Pro Val Thr Lys Phe Pro Leu Ile Pro Val Gly Glu Ala Lys Asn Ile
            180                 185                 190

Asn Asp Asp Glu Phe Gln Asn Ile Tyr Ser Leu Ser His Pro Asn Gln
        195                 200                 205

Leu Lys Cys Pro Gly Phe Glu Pro Val Tyr His Phe Asn Gly Asn Val
    210                 215                 220

Tyr Pro Cys Cys Ser Pro Ala Ile Phe Asp Thr Ala Leu Ile Leu Asn
225                 230                 235                 240

Asp Glu Leu Tyr Gln Asp Phe Asp Lys Thr Ile Thr Lys Met Asn Ser
                245                 250                 255

Asn Leu Leu Leu Tyr Ile Met Arg Arg Glu Gly Phe Ser Trp Phe Ile
            260                 265                 270

Asn Ile Val Ser Asn Asn Asn Glu Phe Ser His Ile Lys Ile Asn Lys
```

```
                275                 280                 285
Glu Phe Ser Ser Ile Cys Ser Ile Cys Arg Gln Leu Phe Lys Thr Glu
    290                 295                 300

Asn Asn Ile Lys Leu Leu Thr Pro Tyr Met Arg Lys Tyr Tyr Glu Gln
305                 310                 315                 320

Met Leu

<210> SEQ ID NO 48
<211> LENGTH: 322
<212> TYPE: PRT
<213> ORGANISM: Enterococcus faecalis

<400> SEQUENCE: 48

Met Lys Glu Gly Val Asn Leu Leu Tyr Asp Ser Val Val Asn Leu
1               5                   10                  15

Gly Ala Arg Cys Asn Ala Ser Cys Glu His Cys Cys Phe Ser Cys Ser
                20                  25                  30

Pro Thr Lys Lys Glu Ala Leu Asp Lys Asn Glu Val Ile Asn Leu Val
            35                  40                  45

Glu Asn Phe Ser Asn Asn Pro Lys Ile Lys Thr Ile Ser Phe Thr Gly
    50                  55                  60

Gly Glu Ile Phe Leu Asn Tyr Pro Phe Leu Tyr Asn Leu Leu Lys Ile
65                  70                  75                  80

Val Asn Ser Ser Gly Lys Ile Ser Thr Leu Ile Ser Asn Gly Phe Trp
                85                  90                  95

Gly Arg Glu Ile Glu Thr Val Lys Lys Tyr Phe Leu Asp Met Asn Arg
            100                 105                 110

Met Gly Val Thr Asn Leu Ser Ile Ser His Asp Asp Phe His Ser Lys
        115                 120                 125

Phe Ile Lys Thr Asp Tyr Ile Arg Asn Ile Leu Ile Glu Ser Arg Lys
    130                 135                 140

Tyr Pro Asp Ile Gln Ile Thr Val Asn Ile Ala Val Ser Lys Asn Ser
145                 150                 155                 160

Thr Gly Asp Lys Ile Ile His Asp Leu Gly Glu Ala Ile Leu Gly Ile
                165                 170                 175

Pro Val Thr Lys Phe Pro Leu Ile Pro Val Gly Glu Ala Lys Asn Ile
            180                 185                 190

Asn Asp Asp Glu Phe Gln Asn Ile Tyr Ser Leu Ser His Pro Asn Gln
        195                 200                 205

Leu Lys Cys Pro Gly Phe Glu Pro Val Tyr His Phe Asn Gly Asn Val
    210                 215                 220

Tyr Pro Cys Cys Ser Pro Ala Ile Phe Asp Thr Ala Leu Ile Leu Asn
225                 230                 235                 240

Asp Glu Leu Tyr Gln Glu Phe Asp Lys Thr Ile Thr Lys Met Asn Ser
                245                 250                 255

Asn Leu Leu Leu Tyr Ile Met Arg Arg Glu Gly Phe Ser Trp Phe Ile
            260                 265                 270

Asn Ile Val Ser Asn Asn Glu Phe Ser His Ile Lys Ile Asn Lys
        275                 280                 285

Glu Phe Ser Ser Ile Cys Ser Ile Cys Arg Gln Leu Phe Lys Thr Glu
    290                 295                 300

Asn Asn Ile Lys Leu Leu Thr Pro Tyr Met Arg Lys Tyr Tyr Glu Gln
305                 310                 315                 320

Met Leu
```

<210> SEQ ID NO 49
<211> LENGTH: 322
<212> TYPE: PRT
<213> ORGANISM: Enterococcus faecalis

<400> SEQUENCE: 49

Met Lys Glu Gly Val Asn Leu Leu Tyr Glu Ser Val Val Asn Leu
1               5                   10                  15

Gly Ala Arg Cys Asn Ala Ser Cys Glu His Cys Cys Phe Ser Cys Ser
            20                  25                  30

Pro Thr Lys Lys Glu Ala Leu Asp Lys Asn Glu Val Ile Asn Leu Val
        35                  40                  45

Glu Asn Phe Ser Asn Asn Pro Lys Ile Lys Thr Ile Ser Phe Thr Gly
    50                  55                  60

Gly Glu Ile Phe Leu Asn Tyr Pro Phe Leu Tyr Ser Leu Leu Lys Ile
65                  70                  75                  80

Val Asn Ser Ser Gly Lys Ile Ser Thr Leu Ile Ser Asn Gly Phe Trp
                85                  90                  95

Gly Arg Glu Ile Glu Thr Val Lys Lys Tyr Phe Leu Asp Met Asn Arg
            100                 105                 110

Met Gly Val Thr Asn Leu Ser Ile Ser His Asp Asp Phe His Ser Lys
        115                 120                 125

Phe Ile Lys Thr Asp Tyr Ile Arg Asn Ile Leu Ile Glu Ser Arg Lys
    130                 135                 140

Tyr Pro Asp Ile Gln Ile Thr Val Asn Ile Ala Val Ser Lys Asn Ser
145                 150                 155                 160

Thr Gly Asp Lys Ile Ile His Asp Leu Gly Glu Ala Ile Leu Gly Ile
                165                 170                 175

Pro Val Thr Lys Phe Pro Leu Ile Pro Val Gly Glu Ala Lys Asn Ile
            180                 185                 190

Asn Asp Asp Glu Phe Gln Asn Ile Tyr Ser Leu Ser His Pro Asn Gln
        195                 200                 205

Leu Lys Cys Pro Gly Phe Glu Pro Val Tyr His Phe Asn Gly Asn Val
    210                 215                 220

Tyr Pro Cys Cys Ser Pro Ala Ile Phe Asp Thr Ala Leu Ile Leu Asn
225                 230                 235                 240

Asp Glu Leu Tyr Gln Tyr Phe Asp Lys Thr Ile Thr Lys Met Asn Ser
                245                 250                 255

Asn Leu Leu Leu Tyr Ile Met Arg Arg Glu Gly Phe Ser Trp Phe Ile
            260                 265                 270

Asn Ile Val Ser Asn Asn Asn Glu Phe Ser His Ile Lys Ile Asn Lys
        275                 280                 285

Glu Phe Ser Ser Ile Cys Ser Ile Cys Arg Gln Leu Phe Lys Thr Glu
    290                 295                 300

Asn Asn Ile Lys Leu Leu Thr Pro Tyr Met Arg Lys Tyr Tyr Glu Gln
305                 310                 315                 320

Met Leu

<210> SEQ ID NO 50
<211> LENGTH: 314
<212> TYPE: PRT
<213> ORGANISM: Enterococcus faecalis

<400> SEQUENCE: 50

-continued

```
Met Tyr Asp Ser Val Val Val Asn Leu Gly Ala Arg Cys Asn Ala Ser
1               5                   10                  15

Cys Glu His Cys Cys Phe Ser Cys Ser Pro Thr Lys Lys Glu Ala Leu
            20                  25                  30

Asp Lys Asn Glu Val Ile Asn Leu Val Glu Asn Phe Ser Asn Asn Pro
        35                  40                  45

Lys Ile Lys Thr Ile Ser Phe Thr Gly Gly Glu Ile Phe Leu Asn Tyr
    50                  55                  60

Pro Phe Leu Tyr Asn Leu Leu Lys Ile Val Asn Ser Ser Gly Lys Ile
65                  70                  75                  80

Ser Thr Leu Ile Ser Asn Gly Phe Trp Gly Arg Glu Ile Glu Thr Val
                85                  90                  95

Lys Lys Tyr Phe Leu Asp Met Asn Arg Met Gly Val Thr Asn Leu Ser
            100                 105                 110

Ile Ser His Asp Asp Phe His Ser Lys Phe Ile Lys Thr Asp Tyr Ile
        115                 120                 125

Arg Asn Ile Leu Ile Glu Ser Arg Lys Tyr Pro Asp Ile Gln Ile Thr
    130                 135                 140

Val Asn Ile Ala Val Ser Lys Asn Ser Thr Gly Asp Lys Ile Ile His
145                 150                 155                 160

Asp Leu Gly Glu Ala Ile Leu Gly Ile Pro Val Thr Lys Phe Pro Leu
                165                 170                 175

Ile Pro Val Gly Glu Ala Lys Asn Ile Asn Asp Asp Glu Phe Gln Asn
            180                 185                 190

Ile Tyr Ser Leu Ser His Pro Asn Gln Leu Lys Cys Pro Gly Phe Glu
        195                 200                 205

Pro Val Tyr His Phe Asn Gly Asn Val Tyr Pro Cys Cys Ser Pro Ala
    210                 215                 220

Ile Phe Asp Thr Ala Leu Ile Leu Asn Asp Glu Leu Tyr Gln Glu Phe
225                 230                 235                 240

Asp Lys Thr Ile Thr Lys Met Asn Ser Asn Leu Leu Leu Tyr Ile Met
                245                 250                 255

Arg Arg Glu Gly Phe Ser Trp Phe Ile Asn Ile Val Ser Asn Asn Asn
            260                 265                 270

Glu Phe Ser His Ile Lys Ile Asn Lys Glu Phe Ser Ser Ile Cys Ser
        275                 280                 285

Ile Cys Arg Gln Leu Phe Lys Thr Glu Asn Asn Ile Lys Leu Leu Thr
    290                 295                 300

Pro Tyr Met Ser Gln Val Gln Thr Pro Val
305                 310

<210> SEQ ID NO 51
<211> LENGTH: 312
<212> TYPE: PRT
<213> ORGANISM: Corynebacterium diphtheriae

<400> SEQUENCE: 51

Met Val Ala Leu Gly Ile Val Ile Asp Arg Lys Cys Asn Ile Arg Cys
1               5                   10                  15

Gly His Cys Cys Phe Ser Ser Thr Pro Gln Ala Glu Glu His Leu Thr
            20                  25                  30

Asp Glu Gln Ile Leu Arg Ile Val Lys Glu Gly Cys Glu Thr Pro Ala
        35                  40                  45

Ile Asp Thr Ile Ser Leu Ser Gly Gly Glu Ala Leu Leu Arg Lys Pro
    50                  55                  60
```

```
Leu Val Leu Glu Val Leu Arg Val Ala Lys Ser Tyr Gly Lys Ala Ala
 65                  70                  75                  80

Thr Leu Val Thr Asn Gly Phe Trp Gly Gln Asn Lys Lys Arg Ala Glu
                 85                  90                  95

Glu Thr Leu Phe Glu Leu Lys Glu Ala Gly Leu Cys Ala Leu Lys Ile
            100                 105                 110

Ser Phe Asp Asp Phe His Gln Asp Leu Leu Lys Val Glu Lys Val Lys
        115                 120                 125

Asn Ile Leu Asp Ala Asn Leu Ser Val Arg Val Pro Ile Ala Ile Asn
130                 135                 140

Val Ala Val Ser Lys Asn Phe Ser Ser Asp Arg Ile Leu Ala Ala Leu
145                 150                 155                 160

Gly Glu Ser Leu Met Gly Val Lys Val Ile Lys Phe Pro Ile Gln Arg
                165                 170                 175

Val Gly Ala Ala Glu Gln Tyr Pro Glu Glu Ser Ile Ile Arg Arg His
            180                 185                 190

Arg Ile Glu Asp Asn Leu Thr Cys Pro Gly Phe Glu Pro Thr Tyr His
        195                 200                 205

Tyr Asp Gly Lys Val Tyr Pro Cys Cys Ser Pro Thr Val Phe Thr Thr
210                 215                 220

Gly Leu Thr Phe Gly Lys Ala Glu Asp Leu Pro Val Glu Arg Ala Val
225                 230                 235                 240

Ser Ser Ile Glu Arg Asn Leu Leu Phe Ala Ala Ile Arg Gln Lys Gly
                245                 250                 255

Phe Lys Trp Leu Phe Glu Arg Cys Ile Glu Glu Arg Val Leu Asp Ile
            260                 265                 270

Ser Tyr Ile Asp Arg Ser Tyr Val Asp Ala Cys Glu Met Cys Gln Ile
        275                 280                 285

Leu Phe Ser Asn Pro His Thr Leu Lys Ala Val Val Ser Ile Val Ser
290                 295                 300

Asn Glu Tyr Thr Ser Ile Ser Lys
305                 310

<210> SEQ ID NO 52
<211> LENGTH: 315
<212> TYPE: PRT
<213> ORGANISM: Streptococcus agalactiae

<400> SEQUENCE: 52

Met Lys Ser Leu Val Ile Asn Leu Ser Gln Lys Cys Asn Ala Lys Cys
  1               5                  10                  15

Asp His Cys Cys Phe Ser Cys Leu Pro Asn Ser Val Asn Cys Leu Thr
                 20                  25                  30

Asp Glu Glu Ile Glu Ala Val Val Arg Tyr Ala Glu Thr His Glu Asp
             35                  40                  45

Val Glu Leu Val Ser Leu Thr Gly Gly Glu Ala Leu Leu Arg Lys Ser
         50                  55                  60

Lys Val Leu Glu Thr Ile His Arg Leu Ser Ile Leu Gly Lys Asp Val
 65                  70                  75                  80

Thr Leu Ile Thr Asn Gly Phe Trp Ala Thr Asn Asp Lys Asn Thr Lys
                 85                  90                  95

Ser Leu Leu Thr Ser Leu Arg Thr Ala Gly Leu Arg Tyr Leu Thr Val
            100                 105                 110

Ser Tyr Asp Asn Tyr His Ser Glu Tyr Ile Pro Val Asp Asn Ile Lys
```

```
            115                 120                 125
Arg Leu Phe Leu His Ile Lys Lys Phe Asp Ile Glu Val Ala Leu Asn
        130                 135                 140

Met Val Val Asp Lys Lys Asn Arg Gly Val Asp Leu Leu Asp Lys Leu
145                 150                 155                 160

Gly Glu Ser Ile Phe Gly Val Pro Ile Thr Ile Val Pro Ala Ser Pro
                165                 170                 175

Val Gly Arg Ala Lys Asn Leu Asn Met Glu Asp Leu Tyr Leu Lys Thr
            180                 185                 190

Ile Asp Glu Leu Glu Leu Thr Cys Pro Ala Thr Gly Trp Glu Phe Val
        195                 200                 205

Ile His His Asp Gly Tyr Val Tyr Pro Cys Cys Ser Pro Ser Val Phe
    210                 215                 220

Glu Thr Asn Leu Arg Ile Gly Ser Ile Gly Asp Ala Asp Ile Ser Glu
225                 230                 235                 240

Leu Glu Asp Lys Phe Tyr Ser Asn Met Leu Leu Tyr Ile Leu Lys Arg
                245                 250                 255

Glu Gly Phe Thr Trp Phe Ile Asp Lys Met Lys Leu Asp Leu Thr Gly
            260                 265                 270

Lys Lys Phe Val Ser Ser Cys Glu Val Cys Lys Phe Ile Phe Ser Asp
        275                 280                 285

Met Asn Lys Ile Lys Ser Ile Thr Asp Asp Ile Lys Glu Tyr Tyr Val
    290                 295                 300

Lys Glu Phe Glu Asn Ile Gly Val Ser Lys Leu
305                 310                 315

<210> SEQ ID NO 53
<211> LENGTH: 316
<212> TYPE: PRT
<213> ORGANISM: Bifidobacterium bohemicum

<400> SEQUENCE: 53

Met Thr Ser Ile Cys Leu Thr Phe Ser Ser Lys Cys Asn Ile Ser Cys
1               5                   10                  15

Ala His Cys Cys Phe Ser Cys Gly Pro His Ser Glu Asp His Leu Ser
                20                  25                  30

Glu Glu Gln Ser Val Lys Ile Val Asp Asp Ala Ile Ala Asn Ala His
            35                  40                  45

Val Asn Ser Ile Gly Phe Ser Gly Gly Glu Ala Leu Leu His Arg Asn
    50                  55                  60

Leu Leu Leu Ser Leu Met Lys Arg Ala Ser Glu Gly Asn Leu Lys Thr
65                  70                  75                  80

Thr Leu Val Ser Asn Gly Phe Trp Gly His Ser Val Ala Asn Ala Gln
                85                  90                  95

Asn Ile Leu Thr Leu Leu Lys Asn Ala Gly Leu Ser Thr Leu Thr Leu
            100                 105                 110

Ser Phe Asp Glu Phe His Glu Lys Phe Ile Pro Thr Gln Arg Ile Ile
    115                 120                 125

Asn Ile Leu Gln Ala Asn Lys Tyr Ile Gly Ile Pro Cys His Ile Ser
130                 135                 140

Met Ala Val Thr Lys Asp His Thr Gly Glu Glu Leu Ile His Asp Leu
145                 150                 155                 160

Gly Glu Ala Gly Phe Thr Ile Pro Ile Thr Arg Phe Pro Val Val Pro
                165                 170                 175
```

Val Gly Ala Ala Ala Gln Leu Pro Lys Glu Asn Ile Tyr Ser His Tyr
            180                 185                 190

Asp Ala Asn Asp Pro Leu Ile Cys Pro Gly Leu Gln Ile Thr Tyr His
            195                 200                 205

Phe Asn Gly Asp Val Tyr Pro Cys Cys Ser Pro Ala Val Phe His Thr
        210                 215                 220

Cys Leu Ser Ile Gly Glu Val Ser Asn Thr Pro Thr His Thr Ala Leu
225                 230                 235                 240

Glu Arg Val Ser Arg Asn Lys Leu Phe Ala Leu Met Gln Arg Ile Gly
                245                 250                 255

Leu Arg Gly Ile Ala Glu Ile Cys Lys Glu His Gly Ile Gly Pro Asp
            260                 265                 270

Leu Thr Lys Val Pro Val Val Asp Pro Cys Asp Leu Cys Arg Lys Ile
        275                 280                 285

Phe Ala Asn Ser Lys Thr Leu Glu Ala Leu Leu Pro Tyr Ile Asp Gln
290                 295                 300

Ala Tyr Arg Lys Thr Leu Pro Asp Lys Val Gln Ser
305                 310                 315

<210> SEQ ID NO 54
<211> LENGTH: 27
<212> TYPE: PRT
<213> ORGANISM: Artificial Sequence
<220> FEATURE:
<223> OTHER INFORMATION: peptide

<400> SEQUENCE: 54

Gly Leu Leu Asp Glu Ser Gln Lys Leu Ala Lys Val Asn Asp Leu Trp
1               5                   10                  15

Tyr Phe Val Lys Ser Lys Glu Asn Arg Trp Ile
            20                  25

<210> SEQ ID NO 55
<211> LENGTH: 19
<212> TYPE: PRT
<213> ORGANISM: Artificial Sequence
<220> FEATURE:
<223> OTHER INFORMATION: peptide

<400> SEQUENCE: 55

Gly Leu Leu Asp Glu Ser Gln Lys Leu Ala Lys Val Asn Asp Leu Trp
1               5                   10                  15

Tyr Phe Val

<210> SEQ ID NO 56
<211> LENGTH: 5
<212> TYPE: PRT
<213> ORGANISM: Artificial Sequence
<220> FEATURE:
<223> OTHER INFORMATION: peptide

<400> SEQUENCE: 56

Leu Gly Ser Gly His
1               5

<210> SEQ ID NO 57
<211> LENGTH: 5
<212> TYPE: PRT
<213> ORGANISM: Artificial Sequence
<220> FEATURE:
<223> OTHER INFORMATION: segment
<220> FEATURE:

```
<221> NAME/KEY: MISC_FEATURE
<222> LOCATION: (3)..(3)
<223> OTHER INFORMATION: Xaa is any amino acid

<400> SEQUENCE: 57

Trp Ile Xaa Gly Ser
1               5

<210> SEQ ID NO 58
<211> LENGTH: 5
<212> TYPE: PRT
<213> ORGANISM: Artificial Sequence
<220> FEATURE:
<223> OTHER INFORMATION: segment
<220> FEATURE:
<221> NAME/KEY: MISC_FEATURE
<222> LOCATION: (3)..(3)
<223> OTHER INFORMATION: Xaa is any amino acid

<400> SEQUENCE: 58

Trp Val Xaa Gly Ser
1               5

<210> SEQ ID NO 59
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is N or D
<220> FEATURE:
<221> NAME/KEY: MISC_FEATURE
<222> LOCATION: (7)..(7)
<223> OTHER INFORMATION: Xaa is V or I
<220> FEATURE:
<221> NAME/KEY: MISC_FEATURE
<222> LOCATION: (8)..(12)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is V or I
<220> FEATURE:
<221> NAME/KEY: MISC_FEATURE
<222> LOCATION: (15)..(15)
<223> OTHER INFORMATION: Xaa is any amino acid

<400> SEQUENCE: 59

Xaa Asp Leu Trp Tyr Phe Xaa Xaa Xaa Xaa Xaa Xaa Trp Xaa Xaa Gly
1               5                   10                  15

Ser

<210> SEQ ID NO 60
<211> LENGTH: 18
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is N or D
<220> FEATURE:
<221> NAME/KEY: MISC_FEATURE
<222> LOCATION: (7)..(7)
<223> OTHER INFORMATION: Xaa is V or I
<220> FEATURE:
<221> NAME/KEY: MISC_FEATURE
<222> LOCATION: (8)..(13)
```

```
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is I or V
<220> FEATURE:
<221> NAME/KEY: MISC_FEATURE
<222> LOCATION: (16)..(16)
<223> OTHER INFORMATION: Xaa is any amino acid

<400> SEQUENCE: 60

Xaa Asp Leu Trp Tyr Phe Xaa Xaa Xaa Xaa Xaa Xaa Xaa Trp Xaa Xaa
1               5                   10                  15

Gly Ser

<210> SEQ ID NO 61
<211> LENGTH: 17
<212> TYPE: PRT
<213> ORGANISM: Artificial Sequence
<220> FEATURE:
<223> OTHER INFORMATION: YydF33_49

<400> SEQUENCE: 61

Trp Tyr Phe Val Lys Ser Lys Glu Asn Arg Trp Ile Leu Gly Ser Gly
1               5                   10                  15

His

<210> SEQ ID NO 62
<211> LENGTH: 17
<212> TYPE: PRT
<213> ORGANISM: Artificial Sequence
<220> FEATURE:
<223> OTHER INFORMATION: Peptide-SA1

<400> SEQUENCE: 62

Trp Tyr Phe Val Arg Ser Ser Lys Asn Arg Trp Val Ala Gly Ser Ala
1               5                   10                  15

His

<210> SEQ ID NO 63
<211> LENGTH: 17
<212> TYPE: PRT
<213> ORGANISM: Artificial Sequence
<220> FEATURE:
<223> OTHER INFORMATION: Peptide-SA2

<400> SEQUENCE: 63

Trp Tyr Phe Val Arg Asn Ser Lys Asn Arg Trp Val Ala Gly Ser Ala
1               5                   10                  15

His

<210> SEQ ID NO 64
<211> LENGTH: 17
<212> TYPE: PRT
<213> ORGANISM: Artificial Sequence
<220> FEATURE:
<223> OTHER INFORMATION: Peptide-SE

<400> SEQUENCE: 64

Trp Tyr Phe Val Lys Ser Lys Gln Asn Arg Trp Val Val Gly Ser Gly
1               5                   10                  15

His

<210> SEQ ID NO 65
```

-continued

```
<211> LENGTH: 17
<212> TYPE: PRT
<213> ORGANISM: Artificial Sequence
<220> FEATURE:
<223> OTHER INFORMATION: Peptide-SP

<400> SEQUENCE: 65

Trp Tyr Phe Val Lys Ser Gln Ser Asn Arg Trp Ile Val Gly Ser Gly
1               5                   10                  15

His

<210> SEQ ID NO 66
<211> LENGTH: 17
<212> TYPE: PRT
<213> ORGANISM: Artificial Sequence
<220> FEATURE:
<223> OTHER INFORMATION: YydF33_49AA

<400> SEQUENCE: 66

Trp Tyr Phe Ala Lys Ser Lys Glu Asn Arg Trp Ala Leu Gly Ser Gly
1               5                   10                  15

His

<210> SEQ ID NO 67
<211> LENGTH: 17
<212> TYPE: PRT
<213> ORGANISM: Artificial Sequence
<220> FEATURE:
<223> OTHER INFORMATION: YydF33_49VV

<400> SEQUENCE: 67

Trp Tyr Phe Val Lys Ser Lys Glu Asn Arg Trp Val Leu Gly Ser Gly
1               5                   10                  15

His

<210> SEQ ID NO 68
<211> LENGTH: 17
<212> TYPE: PRT
<213> ORGANISM: Artificial Sequence
<220> FEATURE:
<223> OTHER INFORMATION: YydF33_49II

<400> SEQUENCE: 68

Trp Tyr Phe Ile Lys Ser Lys Glu Asn Arg Trp Ile Leu Gly Ser Gly
1               5                   10                  15

His

<210> SEQ ID NO 69
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (2)..(2)
<223> OTHER INFORMATION: Xaa is V, I or A
<220> FEATURE:
<221> NAME/KEY: MISC_FEATURE
<222> LOCATION: (3)..(3)
<223> OTHER INFORMATION: Xaa is any amino acid

<400> SEQUENCE: 69

Trp Xaa Xaa Gly Ser
1               5
```

```
<210> SEQ ID NO 70
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (3)..(3)
<223> OTHER INFORMATION: Xaa is any amino acid

<400> SEQUENCE: 70

Trp Ala Xaa Gly Ser
1               5

<210> SEQ ID NO 71
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: Xaa is V, I or A

<400> SEQUENCE: 71

Trp Tyr Phe Xaa
1

<210> SEQ ID NO 72
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: Xaa is V, I or A
<220> FEATURE:
<221> NAME/KEY: MISC_FEATURE
<222> LOCATION: (5)..(5)
<223> OTHER INFORMATION: Xaa is K or R
<220> FEATURE:
<221> NAME/KEY: MISC_FEATURE
<222> LOCATION: (6)..(8)
<223> OTHER INFORMATION: Xaa is a polar amino acid
<220> FEATURE:
<221> NAME/KEY: MISC_FEATURE
<222> LOCATION: (12)..(12)
<223> OTHER INFORMATION: Xaa is V, I or A
<220> FEATURE:
<221> NAME/KEY: MISC_FEATURE
<222> LOCATION: (13)..(13)
<223> OTHER INFORMATION: Xaa is an aliphatic amino acid
<220> FEATURE:
<221> NAME/KEY: MISC_FEATURE
<222> LOCATION: (16)..(16)
<223> OTHER INFORMATION: Xaa is any amino acid

<400> SEQUENCE: 72

Trp Tyr Phe Xaa Xaa Xaa Xaa Xaa Asn Arg Trp Xaa Xaa Gly Ser Xaa
1               5                   10                  15

His

<210> SEQ ID NO 73
<211> LENGTH: 17
<212> TYPE: PRT
<213> ORGANISM: Artificial Sequence
<220> FEATURE:
```

```
<223> OTHER INFORMATION: peptide
<220> FEATURE:
<221> NAME/KEY: MISC_FEATURE
<222> LOCATION: (4)..(4)
<223> OTHER INFORMATION: Xaa is V, I or A
<220> FEATURE:
<221> NAME/KEY: MISC_FEATURE
<222> LOCATION: (5)..(5)
<223> OTHER INFORMATION: Xaa is R or K
<220> FEATURE:
<221> NAME/KEY: MISC_FEATURE
<222> LOCATION: (6)..(6)
<223> OTHER INFORMATION: Xaa is S or N
<220> FEATURE:
<221> NAME/KEY: MISC_FEATURE
<222> LOCATION: (7)..(7)
<223> OTHER INFORMATION: Xaa is S, Q or K
<220> FEATURE:
<221> NAME/KEY: MISC_FEATURE
<222> LOCATION: (8)..(8)
<223> OTHER INFORMATION: Xaa is E, K, S or Q
<220> FEATURE:
<221> NAME/KEY: MISC_FEATURE
<222> LOCATION: (12)..(12)
<223> OTHER INFORMATION: Xaa is V, I or A
<220> FEATURE:
<221> NAME/KEY: MISC_FEATURE
<222> LOCATION: (13)..(13)
<223> OTHER INFORMATION: Xaa is L, V or A
<220> FEATURE:
<221> NAME/KEY: MISC_FEATURE
<222> LOCATION: (16)..(16)
<223> OTHER INFORMATION: Xaa is A or G

<400> SEQUENCE: 73

Trp Tyr Phe Xaa Xaa Xaa Xaa Xaa Asn Arg Trp Xaa Xaa Gly Ser Xaa
1               5                   10                  15

His

<210> SEQ ID NO 74
<211> LENGTH: 17
<212> TYPE: PRT
<213> ORGANISM: Artificial Sequence
<220> FEATURE:
<223> OTHER INFORMATION: peptide

<400> SEQUENCE: 74

Trp Tyr Phe Val Lys Ser Lys Glu Asn Arg Trp Ile Leu Gly Ser Gly
1               5                   10                  15

His

<210> SEQ ID NO 75
<211> LENGTH: 17
<212> TYPE: PRT
<213> ORGANISM: Artificial Sequence
<220> FEATURE:
<223> OTHER INFORMATION: synthetic YydF33-44DD peptide containing two
    D-amino acids

<400> SEQUENCE: 75

Trp Tyr Phe Val Lys Ser Lys Glu Asn Arg Trp Ile Leu Gly Ser Gly
1               5                   10                  15

His

<210> SEQ ID NO 76
<211> LENGTH: 17
<212> TYPE: PRT
<213> ORGANISM: Artificial Sequence
<220> FEATURE:
<223> OTHER INFORMATION: synthetic YydF33-49 peptide
```

<400> SEQUENCE: 76

Trp Tyr Phe Val Lys Ser Lys Glu Asn Arg Trp Ile Leu Gly Ser Gly
1               5                   10                  15

His

<210> SEQ ID NO 77
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (5)..(5)
<223> OTHER INFORMATION: Xaa is K or R
<220> FEATURE:
<221> NAME/KEY: MISC_FEATURE
<222> LOCATION: (6)..(6)
<223> OTHER INFORMATION: Xaa is S or N
<220> FEATURE:
<221> NAME/KEY: MISC_FEATURE
<222> LOCATION: (7)..(7)
<223> OTHER INFORMATION: Xaa is S, Q or K
<220> FEATURE:
<221> NAME/KEY: MISC_FEATURE
<222> LOCATION: (8)..(8)
<223> OTHER INFORMATION: Xaa is E, K, S or Q
<220> FEATURE:
<221> NAME/KEY: MISC_FEATURE
<222> LOCATION: (12)..(12)
<223> OTHER INFORMATION: Xaa is V, I or A
<220> FEATURE:
<221> NAME/KEY: MISC_FEATURE
<222> LOCATION: (13)..(13)
<223> OTHER INFORMATION: Xaa is L, V or A
<220> FEATURE:
<221> NAME/KEY: MISC_FEATURE
<222> LOCATION: (16)..(16)
<223> OTHER INFORMATION: Xaa is A or G

<400> SEQUENCE: 77

Trp Tyr Phe Ala Xaa Xaa Xaa Xaa Asn Arg Trp Xaa Xaa Gly Ser Xaa
1               5                   10                  15

His

<210> SEQ ID NO 78
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: Xaa is V, I or A
<220> FEATURE:
<221> NAME/KEY: MISC_FEATURE
<222> LOCATION: (5)..(5)
<223> OTHER INFORMATION: Xaa is K or R
<220> FEATURE:
<221> NAME/KEY: MISC_FEATURE
<222> LOCATION: (6)..(6)
<223> OTHER INFORMATION: Xaa is S or N
<220> FEATURE:
<221> NAME/KEY: MISC_FEATURE
<222> LOCATION: (7)..(7)
<223> OTHER INFORMATION: Xaa is S, Q or K
<220> FEATURE:
<221> NAME/KEY: MISC_FEATURE
<222> LOCATION: (8)..(8)
<223> OTHER INFORMATION: Xaa is E, K, S or Q
<220> FEATURE:

```
<221> NAME/KEY: MISC_FEATURE
<222> LOCATION: (13)..(13)
<223> OTHER INFORMATION: Xaa is L, V or A
<220> FEATURE:
<221> NAME/KEY: MISC_FEATURE
<222> LOCATION: (16)..(16)
<223> OTHER INFORMATION: Xaa is A or G

<400> SEQUENCE: 78

Trp Tyr Phe Xaa Xaa Xaa Xaa Xaa Asn Arg Trp Ala Xaa Gly Ser Xaa
1               5                   10                  15
His

<210> SEQ ID NO 79
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (5)..(5)
<223> OTHER INFORMATION: Xaa is K or R
<220> FEATURE:
<221> NAME/KEY: MISC_FEATURE
<222> LOCATION: (6)..(6)
<223> OTHER INFORMATION: Xaa is S or N
<220> FEATURE:
<221> NAME/KEY: MISC_FEATURE
<222> LOCATION: (7)..(7)
<223> OTHER INFORMATION: Xaa is S, Q or K
<220> FEATURE:
<221> NAME/KEY: MISC_FEATURE
<222> LOCATION: (8)..(8)
<223> OTHER INFORMATION: Xaa is E, K, S or Q
<220> FEATURE:
<221> NAME/KEY: MISC_FEATURE
<222> LOCATION: (12)..(12)
<223> OTHER INFORMATION: Xaa is V or I
<220> FEATURE:
<221> NAME/KEY: MISC_FEATURE
<222> LOCATION: (13)..(13)
<223> OTHER INFORMATION: Xaa is L, V or A
<220> FEATURE:
<221> NAME/KEY: MISC_FEATURE
<222> LOCATION: (16)..(16)
<223> OTHER INFORMATION: Xaa is A or G

<400> SEQUENCE: 79

Trp Tyr Phe Ile Xaa Xaa Xaa Xaa Asn Arg Trp Xaa Xaa Gly Ser Xaa
1               5                   10                  15
His
```

US 10,981,957 B2

PEPTIDES HAVING ANTIMICROBIAL ACTIVITY AND NEW ENZYME CAPABLE OF CONVERTING L-CONFIGURED RESIDUE IN D-CONFIGURED AMINO ACID IN A PEPTIDE

CROSS-REFERENCE TO RELATED APPLICATION

This application is the U.S. national stage application of International Patent Application No. PCT/EP2016/079362, filed Dec. 1, 2016.

The Sequence Listing for this application is labeled "Sect-List-replace-2.txt" which was created on Jul. 16, 2020 and is 101 KB. The entire content of the sequence listing is incorporated herein by reference in its entirety.

FIELD OF THE INVENTION

The present invention relates to the medicine, in particular the antimicrobial activity of peptides and to the enzymology.

BACKGROUND OF THE INVENTION

Antimicrobial resistance threatens the effective prevention and treatment of an ever-increasing range of infections caused by bacteria, parasites, viruses and fungi. It is an increasingly serious threat to global public health that requires action across all government sectors and society. Antimicrobial resistance is present in all parts of the world. New resistance mechanisms emerge and spread globally.

In consideration of the constant problems due to the antimicrobial resistance, there is a strong need of new classes of antimicrobials. In particular, antimicrobial peptides are of high interest. These peptides are generally potent. In addition, they often offer a better selectivity and specificity than small molecules generally used as therapeutics.

Nevertheless, a major limitation to their use and therapeutic development is associated with their half-life. Indeed, it is commonly decreased by the action of proteases and peptidases which are present in organisms.

Therefore, numerous strategies have been developed in order to reduce the peptide degradation such as C-amidation and N-acetylation against exopeptidase, introduction of non-natural amino acids or of D-configured amino acids. However, these strategies can only be used in the context of synthesized peptides and are not suitable for recombinant production of peptides. In particular, there is no easy way for introducing D-configured amino acid in a peptide, despite the interest of such a modification. Indeed, D-configured amino acid presents the same properties than natural amino acids but are usually more resistant to proteases and even could be less immunogen.

In conclusion, any new class of antimicrobials is of great interest, especially antimicrobial peptides. In addition, any process suitable for modifying L-configured amino acid into D-configured amino acid in a peptide would be highly valuable in this context.

SUMMARY OF THE INVENTION

The inventors identified an antimicrobial peptide derived from bacteria, namely from Bacillus subtilis which possesses D-amino acid residues. Therefore, the inventors discovered a new class of bacteriocins. This peptide has the specificity to present the antimicrobial effect only when some of its amino acids are in D-configuration. This peptide can be prepared by an enzyme derived from the same bacteria which presents the property of changing the configuration of amino acids in a peptide from an L-configuration to a D-configuration. Therefore, this enzyme can be useful for converting L-configured amino acids into D-configured amino acid in peptides, in particular those prepared by recombinant production.

Accordingly the present invention relates to an antimicrobial peptide having at least two D-configured amino acids, comprising a sequence of 17 residues having at least 40% of identity with the sequence in positions 33 to 49 of SEQ ID No 1 and said sequence comprising the sequences W-Y-F-[V/I/A] (SEQ ID No 71) and W-[I/V/A]-X4-G-S (SEQ ID No 69), wherein X4 is any amino acid, and a connecting sequence between SEQ ID No 69 and SEQ ID No 71 of 4-8 amino acids, wherein the residues [V/I/A] of SEQ ID Nos 69 and 71 have a D-configuration.

Preferably, the peptide comprises, essentially consists in or consists in a sequence of W-Y-F-[V/I/A]-[K/R]-Xa-Xb-Xc-N-R-W-[V/I/A]-Xd-G-S-Xe-H (SEQ ID No 72), wherein Xa, Xb and Xc are a polar amino acid, Xd is an aliphatic amino acid and Xe any amino acid. More preferably, the peptide comprises, essentially consists in or consists a sequence of W-Y-F-[V/I/A]-[K/R]-[S/N]-[S/Q/K]-[E/K/S/Q]-N-R-W-[V/I/A]-[L/V/A]-G-S-[A/G]-H (SEQ ID No 73).

In a preferred embodiment, the peptide comprises, essentially consists in or consists in a sequence selected from the group consisting of SEQ ID Nos 61-68.

In one embodiment, the peptide comprises a sequence of 24 residues having at least 40% of identity with the sequence in positions 26 to 49 of SEQ ID No 1 and said sequence comprising the sequences N/D-D-L-W-Y-F-[V/I/A] (SEQ ID No 21) and W-[I/V/A]-X4-G-S (SEQ ID No 69), wherein X4 is any amino acid, and a connecting sequence between SEQ ID No 21 and SEQ ID No 69 of 4-7 amino acids.

Preferably, the peptide comprises the sequences L-X1-X2-X3-N-D-L-W-Y-F-V/I (SEQ ID No 23), and W-I/V-X4-G-S (SEQ ID No 22), wherein X1, X2, X3 and X4 are any amino acid. More preferably, X1 is Alanine, Aspartic acid or Glutamic acid, X2 is Lysine, Asparagine or Aspartic acid and X3 is Valine, Isoleucine or Glutamine.

Preferably, the peptide comprises the sequences L-A-K-V-N-D-L-W-Y-F-V (SEQ ID No 24), and W-I/V-X4-G-S (SEQ ID No 22), wherein X4 is a hydrophobic amino acid, preferably Leucine, Valine, Alanine or Methionine.

Preferably, the Valine or Isoleucine in the sequence N/D-D-L-W-Y-F-[V/I/A] (SEQ ID No 21) has a D-configuration and the Isoleucine or Valine in the sequence W-I/V-X4-G-S (SEQ ID No 22) has a D-configuration.

In a preferred embodiment, the peptide comprises, consists essentially of or consists of the sequence of SEQ ID No 20 and the Valine in position 19 is in D-configuration and the isoleucine in position 27 is in D-configuration.

The present invention also relates to a pharmaceutical composition comprising a peptide according to the present invention.

The present invention further relates to a peptide according to the present invention for use as a drug, preferable as antimicrobial, more preferably as antibacterial. It relates to the use of a peptide according to the present invention for the manufacture of a medicament, preferably an antimicrobial, more preferably an antibacterial. The present invention relates to a method for treating a subject in need thereof, comprising administering a therapeutic amount of a peptide according to the present invention.

The present invention relates to an in vitro method for preparing a peptide according to the present invention, wherein the method comprises a step of contacting a peptide comprising a sequence of 17 residues having at least 40% of identity with the sequence in positions 33 to 49 of SEQ ID No 1 and said sequence comprising the sequences W-Y-F-[V/I/A] (SEQ ID No 71) and W-[I/V/A]-X4-G-S (SEQ ID No 69), wherein X4 is any amino acid, and a connecting sequence between SEQ ID No 69 and SEQ ID No 71 of 4-8 amino acids, with a radical SAM peptide epimerase having an amino acid sequence having at least 30% of identity with SEQ ID No 25 and in which 70% of the positions 14-15, 18, 20-24, 27, 58-60, 63, 83, 84, 87-90, 112, 115, 117, 120, 150, 152, 169, 176, 180, 181, 183, 204, 206-208, 214, 217, 220-225, 228, 230, 252, 254, 262, 289, 292, 296, and 309 of SEQ ID No 25 are conserved.

In one embodiment, the peptide comprises a sequence of 24 residues having at least 40% of identity with the sequence in positions 26 to 49 of SEQ ID No 1 and said sequence comprising the sequences N/D-D-L-W-Y-F-[V/I/A] (SEQ ID No 21) and W-I/V-X4-G-S (SEQ ID No 22), wherein X4 is any amino acid, and a connecting sequence between SEQ ID No 21 and SEQ ID No 22 of 4-7 amino acids.

It further relates to the use of a radical SAM peptide epimerase having an amino acid sequence having at least 30% of identity with SEQ ID No 25 and in which 70% of the positions 14-15, 18, 20-24, 27, 58-60, 63, 83, 84, 87-90, 112, 115, 117, 120, 150, 152, 169, 176, 180, 181, 183, 204, 206-208, 214, 217, 220-225, 228, 230, 252, 254, 262, 289, 292, 296, and 309 of SEQ ID No 25 are conserved for preparing a peptide according to the present invention.

The present invention also relates to a recombinant host cell comprising a heterologous nucleic acid encoding a peptide comprising a sequence of 17 residues having at least 40% of identity with the sequence in positions 33 to 49 of SEQ ID No 1 and said sequence comprising the sequences W-Y-F-[V/I/A] (SEQ ID No 71) and W-[I/V/A]-X4-G-S (SEQ ID No 69), wherein X4 is any amino acid, and a connecting sequence between SEQ ID No 69 and SEQ ID No 71 of 4-8 amino acids, and a heterologous nucleic acid encoding a epimerase having an amino acid sequence having at least 30% of identity with SEQ ID No 25 and in which 70% of the positions 14-15, 18, 20-24, 27, 58-60, 63, 83, 84, 87-90, 112, 115, 117, 120, 150, 152, 169, 176, 180, 181, 183, 204, 206-208, 214, 217, 220-225, 228, 230, 252, 254, 262, 289, 292, 296, and 309 of SEQ ID No 25 and being able to co-express the peptide and the epimerase. In one embodiment, the peptide comprises a sequence of 24 residues having at least 40% of identity with the sequence in positions 26 to 49 of SEQ ID No 1 and said sequence comprising the sequences N/D-D-L-W-Y-F-[V/I/A] (SEQ ID No 21) and W-I/V-X4-G-S (SEQ ID No 22), wherein X4 is any amino acid, and a connecting sequence between SEQ ID No 21 and SEQ ID No 22 of 4-7 amino acids.

Finally, the present invention relates to a method for preparing a peptide according to the present invention, wherein the method comprises culturing a recombinant host cell according to the present invention in conditions suitable for the co-expression the peptide and the epimerase and recovering the peptide having at least one D-configured amino acid or synthetic methods used for peptide synthesis, which allow the assembly of L- and D-configured amino acids.

DETAILED DESCRIPTION OF THE INVENTION

By studying the yydFGHIJ operon of *Bacillus subtilis*, the inventors identified firstly a new class of antimicrobial peptides and, secondly, an epimerase capable of converting in vitro L-configured amino acid into D-configured residue in the peptide. Therefore, this epimerase is useful for peptides engineering.

Antimicrobial Peptide

In a search for genes involved in the regulation of the two-component system LiaRS presumably involved in sensing bacterial cell-wall integrity, Butcher et al (2007, *J Bacteriol*, 189, 8616) identified an operon YydFGHIJ which appeared to induce LiaRS expression. However, no component of this operon could be isolated or investigated in vitro.

The inventors showed that the operon produces a peptide YydF and that this peptide is post-translationaly modified by the YydG enzyme which, very surprisingly, encodes a novel class of radical SAM epimerase. In addition, the inventors discovered that the YydF peptide has antimicrobial activity but only if it comprises D-configured amino acids. In absence of D-configured amino acids, the peptide is devoid of this antimicrobial activity, a feature unknow to date in bioactive peptides. More particularly, two D-configured amino acids are required for this antimicrobial activity.

Accordingly, in one embodiment, the present invention relates to a peptide having at least one D-configured amino acid, preferably two D-configured amino acids, comprising a sequence of 17 residues having at least 40% of identity with the sequence in positions 33 to 49 of SEQ ID No 1. In particular, the peptide may comprise a sequence of 17 residues having at least 45, 50, 55, 60, 70, 80, 85, 90, 95, 98 or 99% of identity with the sequence in positions 33 to 49 of SEQ ID No 1. Alternatively, the peptide may comprise a sequence of 17 residues in positions 33 to 49 of SEQ ID No 1, and 1, 2, 3, 4, 5, 6, 7, 8, 9 or 10 substitutions, additions or deletions.

In one preferred embodiment, the peptide comprises a sequence in which the residues in positions 33-35, 40-43, 46 and 47 of SEQ ID No 1 are conserved. In an additional aspect, residues in positions 36 and 44 of SEQ ID No 1 are selected from the group consisting of V, I and A, preferably V and I.

In a preferred embodiment, the present invention relates to a peptide having at least two D-configured amino acids, comprising a sequence of 17 residues having at least 40% of identity with the sequence in positions 33 to 49 of SEQ ID No 1 and including the sequence W-[I/V/A]-X4-G-S (SEQ ID No 69), wherein X4 is a hydrophobic amino acid, preferably Leucine, Valine or Alanine. In particular, the peptide may comprise a sequence of 17 residues having at least 40, 45, 50, 55, 60, 70, 80, 85, 90 or 95% of identity with the sequence in positions 33 to 49 of SEQ ID No 1. Optionally, the peptide further comprises the sequence W-Y-F-[V/I/A] (SEQ ID No 71). Preferably, the amino acids [V/I/A] of SEQ ID Nos 69 and 71 are D-configured amino acids. In the peptide sequence, when considering orientation from the N-terminal end to the C-terminal end, the sequence W-Y-F-[V/I/A] (SEQ ID No 71) is before the sequence W-[I/V/A]-X4-G-S (SEQ ID No 69), preferably W-[I/V]-X4-G-S (SEQ ID No 22). In a preferred embodiment, the motif W-Y-F-[V/I/A] (SEQ ID No 71) is separated from the motif W-[I/V/A]-X4-G-S (SEQ ID No 69), preferably W-[I/V]-X4-G-S (SEQ ID No 22), by a linking sequence comprising from four to eight amino acids, preferably a linking sequence of five or seven amino acids, preferably of six amino acids. In a most prefered embodiment, the peptide comprises a sequence of W-Y-F-[V/I/A]-[K/R]-Xa-Xb-Xc-N-R-W-[V/I/A]-Xd-G-S-Xe-H (SEQ ID No 72), wherein Xa, Xb and Xc are a polar amino acid, Xd is an aliphatic amino acid and Xe is any amino acid. Preferably, Xa is selected from the group consisting of S, N, C and T, more preferably is S or N. Preferably, Xb is selected from the group consisting of S, N, T, Q, D, E, K, R and H, more preferably selected from the group consisting of S, N, Q and K, still more preferably S, Q and K. Preferably, Xc is selected from the group consisting of S, N, T, Q, D, E, K, R and H, more preferably selected from the group consisting of S, N, Q, E, R and K, still more preferably E, K, S and Q. Preferably, Xd is selected from the group consisting of L, I, V A, more preferably L, V and A. Preferably, Xe is selected from the group consisting of A, G or S, more preferably A or G.

In a very specific embodiment, the peptide essentially consists in or consists in a sequence of W-Y-F-[V/I/A]-[K/R]-[S/N]-[S/Q/K]-[E/K/S/Q]-N-R-W-[V/I/A]-[L/V/A]-G-S-[A/G]-H (SEQ ID No 73).

In an aspect of the invention, the peptide comprises, essentially consists in or consists in a sequence selected from the group consisting of SEQ ID Nos 61-68.

In one embodiment, the present invention relates to a peptide having at least one D-configured amino acid, preferably two D-configured amino acids, comprising a sequence of 24 residues having at least 40% of identity with the sequence in positions 26 to 49 of SEQ ID No 1. In particular, the peptide may comprise a sequence of 24 residues having at least 45, 50, 60, 70, 80, 85, 90, 95, 98 or 99% of identity with the sequence in positions 26 to 49 of SEQ ID No 1. Alternatively, the peptide may comprise a sequence of 24 residues in positions 26 to 49 of SEQ ID No 1, and 1, 2, 3, 4, 5, 6, 7, 8, 9 or 10 substitutions, additions or deletions.

In a preferred embodiment, the peptide comprises a sequence in which the residues in positions 26, 31-35, 43, 46 and 47 of SEQ ID No 1 are conserved. In an additional aspect, one or several residues in positions 23, 25, 27-30, 36, 37, 38, 41, 42, 44, 48 and 49 of SEQ ID No 1 are also conserved. For instance, 1-11 residues in positions 23, 25, 27-30, 36, 37, 38, 41, 42, 44, 48 and 49 of SEQ ID No 1 can be conserved, especially 1, 2, 3, 4, 5, 6, 7, 8, 9, 10 or 11 residues. More preferably, the residues in positions 23, 25, 27-30, 36, 37, 38, 41, 42, 44, 48 and 49 of SEQ ID No 1 are conserved. Still more preferably, the residues in positions 25, 29, and 38 of SEQ ID No 1 are conserved.

Then, a peptide according to the present invention comprises the sequences N/D-D-L-W-Y-F-[V/I/A] (SEQ ID No 21), in particular L-X1-X2-X3-N-D-L-W-Y-F-V/I (SEQ ID No 23), or/and W-I/V/A-X4-G-S (SEQ ID No 22), wherein X1, X2, X3 and X4 are any amino acid. Optionally, the peptide comprises both sequences. Optionally, the sequence W-I/V/A-X4-G-S (SEQ ID No 69) is the sequence W-I/V-X4-G-S (SEQ ID No 22). Preferably, X1 is Alanine, Aspartic acid or Glutamic acid, preferably Alanine and Aspartic acid, more preferably Alanine. Preferably, X2 is Lysine, Asparagine or Aspartic acid, preferably Lysine or Asparagine, more preferably Lysine. Preferably, X3 is Valine, Isoleucine or Glutamine, preferably Valine or Isoleucine, more preferably Valine. Preferably, X4 is a hydrophobic amino acid, preferably Leucine, Valine, Alanine or Methionine. In a particular embodiment, X1 is Alanine and Aspartic acid, preferable Alanine, X2 is Lysine or Asparagine, preferably Lysine, X3 is Valine or Isoleucine, preferably Valine, and X4 is a hydrophobic amino acid, preferably Leucine, Valine or Alanine. In a preferred embodiment, the peptide comprises the sequences L-A-K-V-N-D-L-W-Y-F-V (SEQ ID No 24), and W-I/V-X4-G-S (SEQ ID No 22), wherein X4 is a hydrophobic amino acid, preferably Leucine, Valine or Alanine. "I/V" or "V/I" means herein Isoleucine or Valine.

"N/D "means herein Asparagine or Aspartic Acid. "I/V/A" means herein Isoleucine, Valine or Alanine.

In a preferred aspect, in the sequence W-I/V-X4-G-S (SEQ ID No 22), I/V is an Isoleucine (SEQ ID No 57). Alternatively, in the sequence W-I/V-X4-G-S (SEQ ID No 22), I/V is a Valine (SEQ ID No 58). In another aspect, W-I/V/A-X4-G-S (SEQ ID No 69) is W-A-X4-G-S (SEQ ID No 70). Preferably, X4 is a hydrophobic amino acid, more preferably Leucine, Valine, Alanine or Methionine, still more preferably Leucine, Valine, or Alanine.

In a preferred aspect, in the sequence N/D-D-L-W-Y-F-[V/I/A] (SEQ ID No 21), and N/D is an Asparagine and I/V is a Valine. Alternatively, in the sequence N/D-D-L-W-Y-F-[V/I/A] (SEQ ID No 21), and N/D is an Aspartic Acid and I/V is an Isoleucine.

In the peptide sequence, when considering orientation from the N-terminal end to the C-terminal end, the sequence N/D-D-L-W-Y-F-[V/I/A] (SEQ ID No 21), in particular L-X1-X2-X3-N-D-L-W-Y-F-V/I (SEQ ID No 23), is before the sequence W-I/V-X4-G-S (SEQ ID No 22).

In a preferred embodiment, the motif N/D-D-L-W-Y-F-[V/I/A] (SEQ ID No 21) is separated from the motif W-I/V-X4-G-S (SEQ ID No 22) by a linking sequence comprising from four to seven amino acids, preferably a linking sequence of five or six amino acids, preferably of five amino acids. In a most prefered embodiment, the peptide comprises a sequence of N/D-D-L-W-Y-F-V/I-(X)$_5$-W-I/V-X4-G-S (SEQ ID No 59) or N/D-D-L-W-Y-F-V/I-(X)$_6$-W-I/V-X4-G-S (SEQ ID No 60), X4 having the same meaning than above.

Then, in a preferred embodiment, the present invention relates to a peptide having at least one D-configured amino acid, comprising a sequence of 24 residues having at least 40% of identity with the sequence in positions 26 to 49 of SEQ ID No 1 and including the sequences L-A-K-V-N-D-L-W-Y-F-V (SEQ ID No 24), and/or W-I/V-X4-G-S (SEQ ID No 22), wherein X4 is a hydrophobic amino acid, preferably Leucine, Valine or Alanine. In particular, the peptide may comprise a sequence of 24 residues having at least 45, 50, 60, 70, 80, 85, 90 or 95% of identity with the sequence in positions 26 to 49 of SEQ ID No 1. In a preferred embodiment, one or several residues in positions 23, 25, 27-30, 36, 37, 38, 41, 42, 44, 48 and 49 of SEQ ID No 1 are also conserved, especially 1, 2, 3, 4, 5, 6, 7, 8, 9, 10 or 11 residues.

The peptide comprises at least one D-configured amino acid, preferably two D-configured amino acids. For instance, it may comprise 1, 2, 3, 4 or 5 D-configured amino acids. Optionally, the D-configured amino acids can be any amino acid, preferably an amino acid selected from the group consisting of I, V, A, N, S and T, more preferably selected from the group consisting of I, V and A, still more preferably selected from the group consisting of I and V.

In a particular embodiment, the Valine, Isoleucine or Alanine in the sequence N/D-D-L-W-Y-F-[V/I/A] (SEQ ID No 21) has a D-configuration and/or the Isoleucine, Valine or Alanine in the sequence W-[V/I/A]-X4-G-S (SEQ ID No 69), preferably W-I/V-X4-G-S (SEQ ID No 22), has a D-configuration. In a preferred embodiment, the Valine, Isoleucine or Alanine in the sequence N/D-D-L-W-Y-F-[V/I/A] (SEQ ID No 21) and the Isoleucine, Valine or Alanine in the sequence W-[I/V/A]-X4-G-S (SEQ ID No 69), preferably W-I/V-X4-G-S (SEQ ID No 22), have a D-configuration. In a preferred aspect, the Valine or Isoleucine in the sequence of N/D-D-L-W-Y-F-V/I-(X)$_5$-W-I/V-X4-G-S (SEQ ID No 59) or N/D-D-L-W-Y-F-V/I-(X)$_6$-W-

I/V-X4-G-S (SEQ ID No 60) have a D-configuration. Optionally, the peptide may comprise additional D-configured amino acid.

Preferably, the length of the peptide is no more about 65 amino acids, more preferably no more than 50 amino acids, in particular can be from about 15 to about 50 amino acids, for instance from about 17 to about 50 amino acids, from about 18 to about 50 amino acids, from about 17 to about 40, from about 20 to about 40 or from about 25 to about 35 amino acids.

The peptide can comprise, consist essentially of or consist of a sequence selected from the group consisting of the amino acid sequences shown in SEQ ID Nos 1-19 or a functional fragment thereof comprising the sequences N/D-D-L-W-Y-F-[V/I/A] (SEQ ID No 21), in particular L-X1-X2-X3-N-D-L-W-Y-F-V/I (SEQ ID No 23), and/or W-I/V-X4-G-S (SEQ ID No 22), more preferably L-A-K-V-N-D-L-W-Y-F-V (SEQ ID No 24), and W-I/V-X4-G-S (SEQ ID No 22). By functional is intended having an antimicrobial activity, especially an antibacterial activity.

In a very particular embodiment, the peptide comprises, consists essentially of or consists of the sequence of SEQ ID No 20 and the Valine in position 19 is in D-configuration and/or the isoleucine in position 27 is in D-configuration. Preferably, both the Valine in position 19 and the isoleucine in position 27 are in D-configuration.

In another very particular embodiment, the peptide has the sequence of SEQ ID No 1 and the Valine in position 36 is in D-configuration and/or the isoleucine in position 44 is in D-configuration. Preferably, both the Valine in position 36 and the isoleucine in position 44 are in D-configuration.

In a particular embodiment, the peptide is not found in nature. The peptide is a non-natural peptide.

The N- and C-termini of the peptides described herein may be optionally protected against proteolysis. In a preferred embodiment, the N-terminus may be in the form of an acetyl group, and/or the C-terminus may be in the form of an amide group. In a preferred embodiment, the peptide has a free C-terminal end.

Alternatively or in addition, internal modifications of the peptides to be resistant to proteolysis are also envisioned, e.g. wherein at least a —CONH— peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH=CH-bond.

For instance, the peptide may be modified by acetylation, acylation, amidation, cross-linking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The peptide according to the invention may comprise one or more amino acids which are rare amino acids in particular hydroxyproline, hydroxylysine, allohydroxylysine, 6-N-methylysine, N-ethylglycine, N-methylglycine, N-ethyl-asparagine, allo-isoleucine, N-methylisoleucine, N-methyl-valine, pyroglutamine, aminobutyric acid; or synthetic amino acids in particular ornithine, norleucine, norvaline and cyclohexyl-alanine.

Optionally, the peptide can be linked to additional moiety, optionally through a linker or spacer (e.g., diglycine). Optionally, the peptide can be part of a protein fusion. The additional moiety can be a moiety facilitating its cellular uptake or entry, in particular a PTD (protein transduction domain) or Cell Penetrating Peptide; a homing peptide; a stabilizing agent such as PEG (polyethyleneglycol), oligo-N-methoxy-ethylglycine (NMEG), albumin, an albumin-binding protein or an immunoglobulin Fc domain; an affinity tag such as an immune-tag, biotin, lectin, or chelator; a purification tag such as a His-tag; a detectable label such as an optical tag, a chelated lanthamide, a fluorescent dye, or a FRET acceptor/donor; a targeting moiety; a secretion signal peptide; or a combination thereof.

The additional moiety can be added either at the N-terminal end or C-terminal end of the peptide. Preferably, the additional moiety is added either at the N-terminal end of the peptide.

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

The invention also encompasses the pharmaceutically acceptable salts of a peptide according to the invention. Pharmaceutically acceptable salts may, for example, be salts of pharmaceutically acceptable mineral acids such as hydrochloric acid, hydrobromic acid, sulphuric acid and phosphoric acid; salts of pharmaceutically acceptable organic acids such as acetic acid, citric acid, maleic acid, malic acid, succinic acid, ascorbic acid and tartaric acid; salts of pharmaceutically acceptable mineral bases such as salts of sodium, potassium, calcium, magnesium or ammonium; or salts of organic bases which contain a salifiable nitrogen, commonly used in pharmaceutical technique. The methods for preparing said salts are well known to one of skill in the art.

In a preferred embodiment, the peptide is isolated.

Use of the Antimicrobial Peptide

The present invention relates to a pharmaceutical composition comprising a peptide as defined above. The pharmaceutical composition may further comprise a pharmaceutically acceptable carrier and/or excipient. By pharmaceutical use is also contemplated the veterinary use. Optionally, the pharmaceutical composition may further comprise another active ingredient, preferably another antimicrobial, more preferably another antibacterial or an anti-inflammatory agent.

The pharmaceutical composition comprising the molecule is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

The present invention also relates to a peptide as defined above for use as a drug, in particular as an antimicrobial, more preferably as an antibacterial. It further relates to the use of a peptide as defined above for the manufacture of a medicament for use as an antimicrobial, more preferably as an antibacterial. In addition, it relates to a method for treating or preventing an infection, especially a bacterial infection, comprising administering a therapeutically effective amount of a peptide as defined above, thereby treating or preventing an infection.

In a preferred embodiment, the peptide as defined above is such that the Valine, Isoleucine or Alanine in the sequence N/D-D-L-W-Y-F-[V/I/A] (SEQ ID No 21) and the Isoleucine, Valine or Alanine in the sequence W-[I/V/A]-X4-G-S (SEQ ID No 69), preferably W-I/V-X4-G-S (SEQ ID No 22), have a D-configuration. In a very specific embodiment, the peptide comprises, consists essentially of or consists of the sequence of SEQ ID No 20 and the Valine in position 19 and the isoleucine in position 27 are in D-configuration. In another very particular embodiment, the peptide has the sequence of SEQ ID No 1 and the Valine in position 36 and the isoleucine in position 44 are in D-configuration. In another very particular embodiment, the peptide comprises, essentially consists in or consists in a sequence selected from the group consisting of SEQ ID Nos 61-68, wherein the residues in positions 4 and 12 are in D-configuration.

Optionally, the peptide as defined above can be used in combination with another drug, preferably another antimicrobial, more preferably another antibacterial, or an anti-inflammatory agent.

By "treat" or "treatment" is intended that the disease is cured, alleviated or delayed. It includes the preventive or curative treatment.

The term "therapeutically effective amount" as used in the present application is intended an amount of therapeutic agent, administered to a patient that is sufficient to constitute a treatment of infection.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

In a particular embodiment, the pharmaceutical composition according to the invention comprises 0.001 mg to 10 g of the molecule of the invention. Preferably, pharmaceutical composition according to the invention comprises 0.01 mg to 1 g of the molecule of the invention.

In still another aspect, the present invention relates to the use of a peptide according to the invention as disinfectant, preservative or pesticide. The term "disinfectant" refers to an antimicrobial activity of the peptide on a surface (for example, walls, doors, medical equipment), a liquid (for example, water) or a gas (for example, an anaesthetic gas). According to one embodiment, the peptide according to the invention is used for elimination of bacterial biofilms. According to a preferred embodiment, the peptide according to the invention is used in particular for disinfecting surgical or prosthetic equipment.

In another aspect, the present invention relates to a medical device or implant comprising a body having at least one surface coated with or including a peptide according to the invention. The present invention also relates to a method for preparing a medical device or implant comprising applying a coating of peptide according to the invention, or placing in contact, with at least one surface of the device or implant.

This type of medical device or implant and the uses and methods of preparation thereof are described for example in patent application WO 2005/006938.

The surface coated with or including a peptide according to the invention may be composed of thermoplastic or polymeric materials such as polyethylene, Dacron, nylon, polyesters, polytetrafluoroethylene, polyurethane, latex, silicone elastomers and the like, or of metallic materials such as gold. In a particular embodiment, the peptide of the invention is covalently attached to a functionalized surface, preferably a metallic surface, via its N-terminal or C-terminal end. Optionally, the peptide may be attached to the surface through a spacer arm.

Preferably, the surface may be coated with a peptide at a density of 0.4 to 300 mg/cm$^2$.

Alternatively, the device or implant, in particular bone and joint prosthetic device, may be coated with a cement mixture comprising a peptide according to the invention.

The peptide may be combined with another active molecule, preferably an antibiotic.

The device or implant may be, for example, intravascular, peritoneal, pleural and urological catheters; heart valves; cardiac pacemakers; vascular shunts; coronary stunts; dental implants or orthopaedic or intraocular prosthesis.

Preparation of the Peptide

Peptides described herein can be synthesized using standard synthetic methods known to those skilled in the art, for example chemical synthesis or genetic recombination. In particular, the peptides can be synthesized according to the method originally described by Merrifield.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N- terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl—Z (2-chlorobenzyloxycarbonyl), Br—Z (2-bromobenzyloyycarbonyl), BzI (benzyl), Fmoc (9-fluorenylmcthoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; NO2 (nitro) and Pmc (2,2, 5,7, 8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or trifluoromethane sulfonic acid for the Boc method, and with TFA for the Fmoc method.

Alternatively, the peptide may be synthesized using recombinant techniques. In this case, a nucleic acid and/or a genetic construct comprising a nucleotide sequence encoding a peptide according to the invention is used. Therefore, the present invention relates to a nucleic acid and/or a genetic construct comprising a nucleotide sequence encoding a peptide according to the invention. The genetic construct comprises a polynucleotide encoding a peptide according to the invention as defined herein, and regulatory sequences (such as a suitable promoter(s), enhancer(s), terminator(s), etc.) allowing the expression (e.g. transcription and translation) of a peptide according to the invention in a host cell. Thus, in another aspect, the invention relates to a host or host cell that expresses (or that under suitable circumstances is capable of expressing) a peptide of the invention; and/or that contains a polynucleotide of the invention or genetic construct of the invention.

In order to obtain the D-amino acid containing peptide, the peptide can be co-expressed with the peptide epimerase described in this invention.

The method of producing the peptide may optionally comprise the steps of purifying said peptide, chemically modifying said peptide, and/or formulating said peptide into a pharmaceutical composition. For instance, the peptide described herein can be prepared by recombinant techniques as a protein fusion with a secretion signal peptide or a purification tag. This secretion signal peptide or purification tag can been cleaved or removed at a further stage of production.

In a particular object of the present invention, the method for preparing the peptide comprises providing or synthetizing a peptide as described above with L-configured amino acids and contacting the peptide with an enzyme (i.e., an epimerase), thereby converting at least one L-configured amino acid into D-configured amino acid of said peptide, the epimerase being as defined below.

Radical SAM Epimerase

The inventors identified a radical SAM epimerase called YydG in Bacillus subtilis which is able to modify the configuration of amino acids contained in a peptide from a L-configuration to a D-configuration. This enzyme is capable of carrying out the conversion, even in in vitro conditions. Its sequence is shown in SEQ ID No 18. In addition, this enzyme is unrelated to other know epimerases, even within the radical SAM enzyme superfamily.

Therefore, the present invention relates to an epimerase capable of modifying the configuration of amino acids contained in a peptide from a L-configuration to a D-configuration and comprising an amino sequence having at least 30% of identity with SEQ ID No 25. Preferably, the epimerase comprises an amino sequence having at least 35, 40, 50, 60, 70, 80, 85, 90, 95, 97.5 or 99% identity with SEQ ID No 25.

YydG of *Bacillus subtilis* is described in public databases under the following identification numbers: UniProt Q45595; GeneID 937720; GenBank NP_391897.1 and NC_000964.3.

Based on the teaching of the present disclosure, the one skilled in the art can identify other enzymes from microorganisms having the radical SAM epimerase. The polypeptide may be identified and obtained from other sources including microorganisms isolated from nature (e.g., soil, composts, water, etc.) or DNA samples obtained directly from natural materials (e.g., soil, composts, water, etc.) using the probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected, the polynucleotide can be isolated or cloned by utilizing techniques that are known to those of ordinary skill in the art (see, e.g., Sambrook et al., 1989). The one skilled in the art could also use the sequences data already available in databasis. In addition, the person skilled in the art can prepare variants of the epimerase having the amino acid sequence of SEQ ID No 25 by currently used methods. In particular, variants with advantageous properties such as an increased stability (e.g., thermostability), increased production of D-configured amino acid, modifying the specificity and/or the selectivity of the epimerase, and the like.

100% identical sequences in comparison to SEQ ID No 25 are disclosed in Uniprot AOAOC2UHS5, AOAOA1MJP5 and L8AWU7. Other *Bacillus subtilis* strains present sequences with high identity (up to 90% of identity) and are disclosed in SEQ ID Nos 26-29 and 32. Other *Bacillus* strains present sequences with high identity and are disclosed in SEQ ID Nos 30 and 33-35. Sequences with a significant identity have been identified in *Salinibacillus aidiingensis, Staphylococcus equorum, Staphylococcus pseudintermedius, Staphylococcus epidermidis, Paenibacillus sp, Enterococcus caccae, Enterococcus faecalis, Corynebacterium diphtheria, Streptococcus agalactiae,* and *Bifidobacterium bohemicum* and are disclosed in SEQ ID Nos 31, and 36-52. FIG. 6 shows an alignment of the enzymes' sequences.

(SEQ ID No 25)

```
        10          20          30          40
MYNKTVSINL DSRCNASCDH CCFSSSPTST TRMEKEYIRE 50          60          70          80
LVTEFAKNKT IQVISFTGGE VFLDYKFLKE LMEIIKPYEK 90         100         110         120
QIFLISNGFW GLSKKKVQEY FHDMNSLNVI ALTISYDEYH
```

-continued

```
          130        140        150        160
    APFVKSSSIK NILEHSRKYP DIDISLNMAV TKDKMSNHIL 170        180        190        200
    EELGDSILGV KITKFPMISV GAAKTRIKQE NIHKFYSLED 210        220        230        240
    EDSLHCPGYD IVYHHDGEIY PCCSPAIFET KITLREEYNQ 250        260        270        280
    SFERTVEKLN SNLLLFILRK EGFKWFLNIL KENNKIEEFD 290        300        310
    IPYEFSSICG VCGSLFNSAE KINYFYPYME KYYNENFKV
```

Positions in bold and underlined are perfectly conserved among the list of sequences disclosed above. Positions in bold and italic are conserved between groups of strongly similar properties among the list of sequences disclosed above. Accordingly, it can be observed that even if the identity percentage is around 30%, there are a high number of amino acids that are perfectly conserved and well-conserved.

Accordingly, in a preferred embodiment, the epimerase has an amino acid sequence having at least 30% of identity with SEQ ID No 25 and in which 70, 80 or 90% of the positions in bold and underlined are conserved when the sequence is aligned with SEQ ID No 25 (positions 14-15, 18, 20-24, 27, 58-60, 63, 83, 84, 87-90, 112, 115, 117, 120, 150, 152, 169, 176, 180, 181, 183, 204, 206-208, 214, 217, 220-225, 228, 230, 252, 254, 262, 289, 292, 296, and 309 of SEQ ID No 25). Preferably, 95% of the positions in bold and underlined are conserved. In a particular embodiment, all the positions in bold and underlined are conserved. More preferably, 90 or 95% of the positions 14-15, 18, 20-24, 27, 58-60, 63, 83, 84, 87-90, 112, 115, 117, 120, 204, 206-208, 214, 217, 220-225, 228, and 230 of SEQ ID No 25 are conserved in the epimerase sequence. In a particular embodiment, all the positions 14-15, 18, 20-24, 27, 58-60, 63, 83, 84, 87-90, 112, 115, 117, 120, 204, 206-208, 214, 217, 220-225, 228, and 230 of SEQ ID No 25 are conserved in the epimerase sequence.

In a preferred embodiment, the epimerase has an amino acid sequence having at least 30% of identity with SEQ ID No 25 and one or several segments selected from the segments 13-27, 56-63, 83-90, 112-120, and 204-230 have at least 50% of identity with the sequence of SEQ ID No 25. In this embodiment, the epimerase has in addition, 90 or 95% of the positions 14-15, 18, 20-24, 27, 58-60, 63, 83, 84, 87-90, 112, 115, 117, 120, 204, 206-208, 214, 217, 220-225, 228, and 230 of SEQ ID No 25 are conserved in the epimerase sequence.

In a particular embodiment, the cysteine residues in positions 14, 18, 21, 222 and 223 of SEQ ID No 25 are conserved in the epimerase sequence.

In an embodiment, the epimerase has an amino acid sequence comprising, consisting essentially in, or consisting in a sequence having at least 80, 85, 90 or 95% of identity with a sequence selected among SEQ ID Nos 25-52, preferably among SEQ ID Nos 25-30, 32 and 34, more preferably SEQ ID No 25. The epimerase may have an amino acid sequence comprising, consisting essentially in, or consisting in a sequence selected among SEQ ID Nos 25-52, preferably among SEQ ID Nos 25-30, 32 and 34, more preferably SEQ ID No 25; and having 1, 2, 3, 4, 5, 6, 7, 8, 9 or 10 substitutions, additions or deletions.

A method for testing the capacity of an epimerase to modify the configuration of amino acids contained in a peptide from a L-configuration to a D-configuration is for instance disclosed in details in the example section. For instance, the epimerase is contacted with a peptide having a sequence selected from the group consisting of SEQ ID Nos 1-20 in presence of the co-factor S-adenosyl-L-methionine (SAM) and the production of peptides including a D-configured amino acid is detected. More specifically, the epimerase is contacted with the peptide YydF18-49 of SEQ ID No 20 in presence of the co-factor S-adenosyl-L-methionine (SAM) and the production of peptides including a D-configured amino acid in position 19 and/or 27 is detected.

It is also provided a hybrid polypeptide or fusion polypeptide in which the amino acid sequence of the enzyme as defined above is fused at the N-terminus or the C-terminus of a region of another polypeptide. Techniques for producing fusion polypeptides are known in the art, and include ligating the coding sequences encoding the enzyme and the addition region of another polypeptide so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

The addition region of the fusion polypeptide can be selected in order to enhance the stability of the enzyme according to the present disclosure, to promote the secretion (such as a N-terminal hydrophobic signal peptide) of the fusion protein from a cell (such as a bacterial cell or a yeast cell), or to assist in the purification of the fusion protein. More particularly, the additional region can be a tag useful for purification or immobilization of the enzyme. Such a tag is well-known by the person skilled in the art, for instance a His tag ($His_6$), a FLAG tag, a HA tag (epitope derived from the Influenza protein haemagglutinin), a maltose-binding protein (MPB), a MYC tag (epitope derived from the human proto-oncoprotein MYC), a STREP tag or a GST tag (small glutathione-S-transferase).

A fusion polypeptide can further comprise a cleavage site between the enzyme and the addition region. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13:498-503; and Contreras et al., 1991, Biotechnology 9: 378-381; Eaton et al., 1986, Biochemistry 25:505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

It is further provided a recombinant nucleic acid construct or vector comprising a nucleic acid sequence encoding the epimerase as defined above. More particularly, the nucleic acid construct or vector is suitable for expressing said epimerase. In addition, it is provided a recombinant host cell comprising a nucleic acid, a recombinant nucleic acid construct or a recombinant vector comprising a nucleic acid sequence encoding the epimerase as defined above.

Nucleic Acid Constructs

Indeed, the present invention relates to a polynucleotide encoding an epimerase of the present invention. The nucleic acid can be DNA (cDNA or gDNA), RNA, or a mixture of the two. It can be in single stranded form or in duplex form or a mixture of the two. It can comprise modified nucleotides, comprising for example a modified bond, a modified purine or pyrimidine base, or a modified sugar. It can be prepared by any method known to one skilled in the art, including chemical synthesis, recombination, and mutagenesis.

The present invention also relates to nucleic acid constructs comprising a polynucleotide encoding an epimerase according to the present disclosure operably linked to one or more control sequences that direct the expression of the coding sequence in a suitable host cell under conditions compatible with the control sequences. A polynucleotide may be manipulated in a variety of ways to provide for expression of the epimerase. Manipulation of the polynucleotide prior to its insertion into a vector may be desirable or necessary depending on the expression vector. The techniques for modifying polynucleotides utilizing recombinant DNA methods are well known in the art.

The control sequence may include a promoter that is recognized by a host cell or an in vitro expression system for expression of a polynucleotide encoding an epimerase of the present invention. The promoter contains transcriptional control sequences that mediate the expression of the epimerase. The promoter may be any polynucleotide that shows transcriptional activity in the host cell including mutant, truncated, and hybrid promoters, and may be obtained from genes encoding extracellular or intracellular polypeptides either homologous or heterologous to the host cell. Optionally, the promoter can be inducible.

Examples of suitable promoters in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, Molecular Microbiology 13: 97-107), *E. coli* lac operon, *E. coli* trc promoter (Egon et al., 1988, Gene 69: 301-315), *Streptomyces coelicolor* agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21 -25). Further promoters are described in "Useful proteins from recombinant bacteria" in Gilbert et al., 1980, Scientific American 242: 74-94; and in Sambrook et al., 1989. Examples of tandem promoters are disclosed in WO 99/43835.

Examples of suitable promoters in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus triose* phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene; and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cry111A gene (WO 94/25612) and a *Bacillus subtilis* SP82 gene (Hue et al., 1995, Journal of Bacteriology 177: 3465-3471).

The control sequence may also be a leader, a non-translated region of an mRNA that is important for translation by the host cell. The leader is operably linked to the 5'-terminus of the polynucleotide encoding the epimerase. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide encoding the epimerase and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of the epimerase and directs the epimerase into the cell's secretory pathway. The 5'-end of the coding sequence of the polynucleotide may inherently contain a signal peptide coding sequence naturally linked in translation reading frame with the segment of the coding sequence that encodes the epimerase. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 1 1837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a nucleic acid construct as disclosed above, or a polynucleotide encoding an epimerase of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the epimerase at such sites. Alternatively, the polynucleotide may be expressed by inserting the polynucleotide or a nucleic acid construct comprising the polynucleotide into an appropriate vector for expression.

In a particular embodiment, the expression vector may further comprise a polynucleotide encoding a peptide of the present invention as disclosed above, operably linked with the control sequences necessary for its expression. More particularly, the control sequences used for the expression of the epimerase and the peptide of the present invention are suitable for co-expression in a host cell. Optionally, the polynucleotide encoding the peptide and the polynucleotide encoding the epimerase can be on the control of a single promoter (i.e., operon) or of two promoters which can be the same or different.

Alternatively, the present invention relates to a kit comprising a first expression vector comprising a nucleic acid encoding an epimerase of the present invention and a second expression vector comprising a nucleic acid encoding a peptide of the present invention. In another alternative, the kit can comprise an expression vector comprising a nucleic acid encoding an epimerase of the present invention and a nucleic acid encoding a peptide of the present invention.

In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophy, and the like.

Examples of bacterial selectable markers are *Bacillus licheniformis* or *Bacillus subtilis* genes or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* gene.

The vector preferably contains an element(s) that permits integration of the vector into the host cell's genome or autonomous replication of the vector in the cell independent of the genome.

When integration into the host cell genome occurs, integration of the sequences into the genome may rely on homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo. Examples of bacterial origins of replication are the origins of replication of plasmids pBR322, pUC19, pACYC177, and pACYC184 permitting replication in *E. coli,* and pUB1 10, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. Examples of origins of replication useful in a filamentous fungal cell are AMA1 and ANSI (Gems et al., 1991, Gene 98: 61 -67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells comprising a polynucleotide encoding an epimerase according to the present disclosure operably linked to one or more control sequences that direct the production of the epimerase of the present invention. A construct or vector comprising a polynucleotide encoding an epimerase according to the present disclosure is introduced into a host cell so that the construct or vector is maintained as a chromosomal integrant or as a self-replicating extra-chromosomal vector as described earlier.

The present invention further relates to a recombinant host cell that further comprises a polynucleotide encoding a peptide according to the present disclosure operably linked to one or more control sequences that direct the production of the peptide. In particular, the host cell can co-express the epimerase and the peptide according to the present disclosure. In this embodiment, the host cell both produces a peptide of the present invention and the epimerase which is able to modify the antimicrobial peptide by changing the configuration of peptide's amino acid from a L-configuration to a D-configuration.

In a preferred embodiment, the host cell comprises a nucleic acid encoding an epimerase of the present invention heterologous to the host cell. In an alternative preferred embodiment, the host cell comprises a nucleic acid encoding a peptide heterologous to the host cell. In another preferred embodiment, the host cell comprises nucleic acids encoding a peptide and an epimerase, both heterologous to the host cell.

The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of an epimerase of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*. The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells. The bacterial host cell may also be any *Streptococcus* cell including, but not limited to, *Streptococcus equisimilis, Streptococcus pyogenes, Streptococcus uberis, Streptococcus equi* and *Streptococcus zooepidemicus* cells. The bacterial host cell may further be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, Mol. Gen. Genet. 168:111-115), competent cell transfoiiiiation (see, e.g., Young and Spizizen, 1961, J. Bacteriol. 81 :823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an *E. coli* cell may be effected by protoplast transformation (see, e.g., Hanahan, 1983, J. Mol. Biol. 166: 557-580) or electroporation (see, e.g., Dower et al, 1988, Nucleic Acids Res. 16: 6127-6145). The introduction of DNA into a *Streptomyces* cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a Pseudomonas cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a *Streptococcus* cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell. The host cell may be a fungal cell. "Fungi" as used herein includes the phyla *Ascomycota, Basidiomycota, Chytridiomycota,* and *Zygomycota* as well as the *Oomycota* and all mitosporic fungi (as defined by Hawksworth et al., In, Ainsworth and Bisby's Dictionary of The Fungi, 8th edition, 1995, CAB International, University Press, Cambridge, UK). The fungal host cell may be a yeast cell. "Yeast" as used herein includes ascosporogenous yeast (Endomycetales), basidiosporogenous yeast, and yeast belonging to the *Fungi imperfecti* (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980). The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces corlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell. The fungal host cell may be a filamentous fungal cell. "Filamentous fungi" include all filamentous forms of the subdivision *Eumycota* and *Oomycota* (as defined by Hawksworth et al., 1995, supra). The filamentous fungi are generally characterized by a mycelial wall composed of chitin, cellulose, glucan, chitosan, mannan, and other complex polysaccharides. The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielovia, Tolypocladium, Trametes,* or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium su/phureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

The cell can also be a mammalian cell, for example COS, CHO (U.S. Pat. Nos. 4,889,803; 5,047,335). In a particular embodiment, the cell is non-human and non-embryonic. In addition, the epimerase of the invention could be produce by a non-human transgenic animal, for instance in the milk produces by the animal.

The cell can be a plant cell. Then, the epimerase of the invention could be produce by a transgenic plant.

Alternatively, it is also provided a method for producing an epimerase according to the present invention, comprising culturing the host cell as defined above, under conditions conducive to the production of the epimerase, and recovering and/or purifying the epimerase. Alternatively, it is also provided a method for producing an epimerase according to the present invention, comprising the in vitro expression of the epimerase with a nucleic acid encoding the epimerase as defined above. Optionally, the method further comprises a step of immobilizing the epimerase on a solid support.

The enzyme may be recovered using methods known in the art. For example, the enzyme may be recovered from the nutrient medium by conventional procedures including, but not limited to, collection, centrifugation, filtration, extraction, spray-drying, evaporation, or precipitation.

The enzyme may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides. In an alternative aspect, the enzyme is not recovered, but rather a host cell of the present invention expressing the enzyme is used as a source of the enzyme.

It is also provided a composition or a kit comprising the isolated or recombinant epimerase as defined above. In particular, the composition or kit may include iron (e.g., $(NH_4)_2Fe(SO_4)_2$) and sulfur (e.g., $Na_2S$) as enzyme additives and a reducing agent such as dithiothreitol or beta-mercaptoethanol. In addition the composition may include S-adenosyl L-methionine (SAM), the enzyme cofactor or methionine and ATP when in the presence of SAM synthase. Optionally the epimerase can be immobilized on a solid support.

The present invention also relates to the use of an epimerase as defined above, a composition, kit or solid support comprising the epimerase, or a recombinant host cell comprising a nucleic acid, a recombinant nucleic acid construct or a recombinant vector comprising a nucleic acid sequence encoding the epimerase as defined above, for producing peptide with D-configured amino acids.

Use of the Epimerase for Converting L-amino Acid into D-amino Acid in a Peptide

Accordingly, the present invention relates to the use of an epimerase of the invention for converting L-amino acid into D-amino acid in a peptide. It also relates to a method for converting L-amino acid into D-amino acid in a peptide comprising contacting an epimerase of the present invention with the peptide, and optionally recovering the peptide with at least one amino acid converted from a L-configuration to a D-configuration.

In a preferred embodiment, the present invention relates to a method for preparing a peptide according to the present invention, wherein the method comprises a step of contacting a peptide according to the present invention with an epimerase as defined above. It also relates to the use of an epimerase as defined above for preparing a peptide according to the present invention. In particular, the peptide can have any particular sequence as defined above. Preferably, the method is carried out in vitro. In a first embodiment, the peptide comprises a sequence of 17 residues having at least 40% of identity with the sequence in positions 33 to 49 of SEQ ID No 1 and said sequence comprising the sequences W-Y-F-[V/I/A] (SEQ ID No 71) and W-[I/V/A]-X4-G-S (SEQ ID No 69), wherein X4 is any amino acid, and a connecting sequence between SEQ ID No 69 and SEQ ID No 71 of 4-8 amino acids. In a second embodiment, the peptide comprises a sequence of 24 residues having at least 40% of identity with the sequence in positions 26 to 49 of SEQ ID No 1 and comprising the sequences N/D-D-L-W-Y-F-[V/I/A] (SEQ ID No 21) and W-I/V-X4-G-S (SEQ ID No 22), wherein X4 is any amino acid.

Finally, the present invention relates to a method for preparing a peptide according to the present invention, wherein the method comprises culturing a recombinant host cell according to the present invention in conditions suitable for the co-expression the peptide and the epimerase and recovering the peptide having at least one D-configured amino acid. Preferably, the method is carried out ex vivo. It also relates to the use of a recombinant host cell according to the present invention for preparing a peptide as defined above.

In a particular aspect, the sources of epimerase and peptide can be matched. For instance, an epimerase from *Bacillus subtilis* could be preferably used for preparing a peptide from or derived from *Bacillus subtilis*. In this particular aspect, if the peptide as defined above comprises a sequence having at least 80, 85, 90 or 95% of identity with a sequence selected among SEQ ID Nos 1-5 or a fragment thereof of at least 24 consecutive residues, then the chosen epimerase will have at least 80, 85, 90 or 95% of identity with a sequence selected among SEQ ID Nos 25-35. If the peptide as defined above comprises a sequence having at least 80, 85, 90 or 95% of identity with a sequence selected among SEQ ID Nos 6-9 or a fragment thereof of at least 24 consecutive residues, then the chosen epimerase will have at least 80, 85, 90 or 95% of identity with a sequence selected among SEQ ID Nos 36-38. If the peptide as defined above comprises a sequence having at least 80, 85, 90 or 95% of identity with a sequence of SEQ ID No 10 or a fragment thereof of at least 24 consecutive residues, then the chosen epimerase will have at least 80, 85, 90 or 95% of identity with a sequence selected among SEQ ID Nos 39-40. If the peptide as defined above comprises a sequence having at least 80, 85, 90 or 95% of identity with a sequence selected among SEQ ID Nos 11-13 and 17-18 or a fragment thereof of at least 24 consecutive residues, then the chosen epimerase will have at least 80, 85, 90 or 95% of identity with a sequence selected among SEQ ID Nos 41-50. If the peptide as defined above comprises a sequence having at least 80, 85, 90 or 95% of identity with a sequence selected among SEQ ID Nos 14-16 or a fragment thereof of at least 24 consecutive residues, then the chosen epimerase will have at least 80, 85, 90 or 95% of identity with a sequence of SEQ ID No 51. If the peptide as defined above comprises a sequence having at least 80, 85, 90 or 95% of identity with a sequence of SEQ ID No 19 or a fragment thereof of at least 24 consecutive residues, then the chosen epimerase will have at least 80, 85, 90 or 95% of identity with a sequence of SEQ ID No 52.

Definitions

About: When used herein, "about" means more or less 10%, preferably more or less 5%. For instance, about 100 means between 90 and 110, preferably between 95 and 105.

"consists of", "consists essentially of" or "substantially comprises": The description herein of any aspect or embodiment of the invention using terms such as reference to an element or elements is intended to provide support for a similar aspect or embodiment of the invention that "consists of", "consists essentially of" or "substantially comprises" that particular element or elements, unless otherwise stated or clearly contradicted by context. For instance, a peptide or protein described herein as comprising a particular sequence should be understood as also describing a peptide or protein consisting of that sequence, unless otherwise stated or clearly contradicted by context. By "consists essentially of" is intended that the peptide or protein consists of that sequence, but it may also include 1, 2, 3, 4, 5, 6, 7, 8, 9 or 10 substitutions, additions or deletions. In particular, by "essentially consist in", it may be intended that the peptide may include 1, 2, 3, 4, 5, 6, 7, 8, 9 or 10 additional amino acids at the N or C-terminal end and 1, 2 or 3 substitutions, deletions or additions.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding an epimerase of the present invention. Control sequences may be native (i.e., from the same gene) or heterologous (i.e., from a different gene and/or a different species) to the polynucleotide encoding the epimerase. Preferably, control sequences are heterologous. Well-known control sequences and currently used by the person skilled in the art will be preferred. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding the epimerase. The functional combination of control sequences and coding sequences can be referred as expression cassette.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding the epimerase of the invention and is operably linked to control sequences that provide for its expression. Then the expression vector comprises an expression cassette suitable for expressing the epimerase of the invention.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance).

Recombinant: Recombinant refers to a nucleic acid construct, a vector and a protein produced by genetic engineering.

Heterologous: in the context of a host cell, a vector or a nucleic acid construct, it designates a coding sequence for the epimerase/peptide introduced into the host cell, the vector or the nucleic acid construct by genetic engineering. In the context of a host cell, it can mean that the coding sequence for the epimerase/peptide originates from a source different from the cell in which it is introduced. For instance, an epimerase from Bacillus subtilis is expressed in E. coli. Alternatively, it can also mean that the coding sequence for the epimerase/peptide comes from the same species as the cell in which it is introduced but it is considered heterologous due to its environment which is not natural, for example because it is under the control of a promoter which is not its natural promoter, or is introduced at a location which differs from its natural location.

Nucleic acid construct: The term "nucleic acid construct" means a nucleic acid molecule, either single- or double-stranded, which is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to a coding sequence, in such a way that the control sequence directs expression of the coding sequence.

Sequence identity: The sequence identity between two amino acid sequences is described by the parameter "sequence identity". For purposes of the present invention, the "percentage identity" between two amino acid sequences (A) and (B) is determined by comparing the two sequences aligned in an optimal manner, through a window of comparison. Said alignment of sequences can be carried out by well-known methods, for example, using the algorithm for global alignment of Needleman-Wunsch. Protein analysis software matches similar sequences using measures of similarity assigned to various substitutions, deletions and other modifications, including conservative amino acid substitutions. Once the total alignment is obtained, the percentage of identity can be obtained by dividing the full number of identical amino acid residues aligned by the full number of residues contained in the longest sequence between the sequence (A) and (B).

Sequence identity is typically determined using sequence analysis software. For comparing two amino acid sequences, one can use, for example, the tool "Emboss needle" for pairwise sequence alignment of proteins providing by EMBL-EBI and available on:
see Worldwide Website:
ebi.ac.uk/Tools/services/web/
toolform.ebi?tool=emboss_needle&context=protein,
using default settings: (I) Matrix: BLOSUM62, (ii) Gap open: 10, (iii) gap extend: 0.5, (iv) output format: pair, (v) end gap penalty: false, (vi) end gap open: 10, (vii) end gap extend: 0.5.

Alternatively, Sequence identity can also be typically determined using sequence analysis software Clustal Omega using the HHalign algorithm and its default settings as its core alignment engine. The algorithm is described in Riding, J. (2005) 'Protein homology detection by HMM-HMM comparison'. Bioinformatics 21, 951-960, with the default settings.

Amino acids: The amino acid sequences defined herein are represented by a one-letter symbol as shown below: A , Ala, (alanine); R , Arg, (arginine); N , Asn, (asparagine); D, Asp, (aspartic acid); C, Cys, (cysteine); Q, Gln, (glutamine); E, Glu, (glutamic acid); G, Gly, (glycine); H, His, (histidine); I, Ile, (isoleucine); L, Leu, (leucine); K, Lys, (lysine); M, Met, (methionine); F, Phe, (phenylalanine); P, Pro, (proline); S, Ser, (serine); T, Thr, (threonine); W, Trp, (tryptophan); Y, Tyr, (tyrosine); and V, Val, (valine).

Conserved: By conserved amino acid is intended that a defined sequence is aligned with the reference sequence and the residue of the defined sequence corresponding the position indicated in the reference sequence is identical to the residue present in the reference sequence. The alignment can be performed by any available method, and in particular by the method disclosed for identity determination just above, more preferably by Clustal Omega. The residue position is indicated in the reference sequence.

The term "antimicrobial" as employed herein refers to an antibacterial, antiviral, antifungal and/or antiparasitic activity. Said activity may be evaluated by measuring different parameters such as $IC_{50}$ or MIC.

"$IC_{50}$" or "half maximal inhibitory concentration" is the concentration of a substance needed to reduce the growth in vitro of a population of microorganisms by half.

"MIC" or "minimum inhibitory concentration" is the lowest concentration of a substance that will totally inhibit microbial growth after 18 hours of incubation, generally at 37° C., in the presence of said substance.

The term "lethal concentration, 50%" or "$LC_{50}$" as employed herein refers to the concentration of substance required to kill half a population. $LC_{50}$ is a quantitative indicator of the toxicity of a substance. In particular, $LC_{50}$ is employed herein to evaluate the cytolytic activity of AMP and in this case corresponds to the concentration of peptide inducing lysis of half the cell population.

BRIEF DESCRIPTION OF THE DRAWINGS

FIG. 4—Activity of YydG mutants. (FIG. 4A) Sequence of YydG with cysteine residues highlighted. (FIG. 4B) Gel electrophoresis analysis of the purified mutant enzymes. (FIG. 4C) UV-visible spectra of A3 (i.e. AxxxAxxA) (blue trace), C22A (green trace), C222A (red trace) and C223A (purple trace) mutants after anaerobic reconstitution.

FIG. 5—Activity of YydF18-49 of YydG.

FIG. 6—Multiple alignments of close YydG homologs found in particular in *B. subtilis* and Staphylococci species.

EXAMPLES

Example 1

Here the inventors showed that the common laboratory strain Bacillus subtilis is able to produce a novel type of bioactive peptides containing D-amino acids despite being of ribosomal origin. This peptide is post-translationally modified by a novel enzyme belonging to the superfamily of radical SAM enzymes. They demonstrated that this novel enzyme uses an unprecedented radical-based mechanism to convert L-Isoleucine and L-valine residues into D-allo-Isoleucine and D-valine. They established that this enzyme generates a 5'-deoxyadenosyl radical to catalyze C$_\alpha$ H-atom abstraction leading to the formation of a carbon-centered radical. Mutagenesis experiments support that this enzyme possesses two essential [4Fe-4S] centers and allow identifying a critical H-atom donor, required for the termination of the catalytic cycle. Finally, in a unique manner, they discovered that the presence of D-amino acids is required for the activity of this bioactive peptide which likely induces LiaRS, a major component of the bacterial cell wall integrity.

The Lia system of *Bacillus subtilis* is a cell envelope stress module composed of a two-component system (LiaRS) and an inhibitory protein (LiaF). This genetic system is highly conserved among Firmicutes and part of the complex regulatory network orchestrating the cell wall stress response. Although its regulation has been described in great details, its precise physiological role in *B. subtilis* is not fully understood. LiaRS is specifically and strongly induced by antibiotics targeting the cell wall such as nisin, vancomycin or bacitracin and has thus been developed as a biosensor and high-throughput screen for cell wall antibiotics. Upon antibiotics sensing, LiaRS transduces cell envelop stress signals activating gene expression presumably to maintain cell wall integrity although it does not confer antibiotic resistance.

Figure 1A:
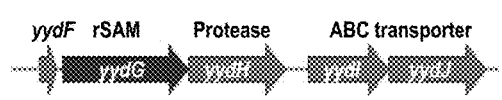
(FIG. 1A) Structure of the yydFGHIJ operon. yydF: Putative peptide, yydG: radical SAM enzyme, yydH: protease, yydIJ ABC-type transporter.

In an attempt to identify genes involved in LiaRS regulation, a mutagenesis study was undertaken in *B. subtilis* and led to the discovery of the yydFGHIJ operon (Butcher et al, 2007, *J Bacteriol*, 189, 8616). This operon shows positive regulation on LiaRS and possesses all the characteristic features of a genetic system encoding a putative peptide (YydF) modified by a radical SAM enzyme and a protease (YydG and YydH respectively) then finally exported in the extracellular medium by an ABC-type transporter (YydIJ) even though none of these components were ever isolated or investigated (FIG. 1A).

Figure 1B:
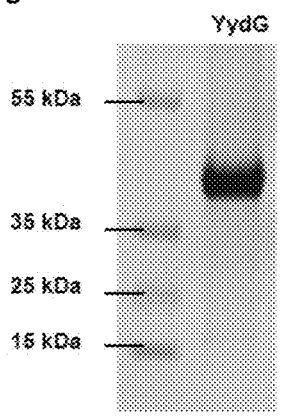
(FIG. 1B) Gel electrophoresis analysis of purified YydG expressed in *E. coli*.
Figure 1C:
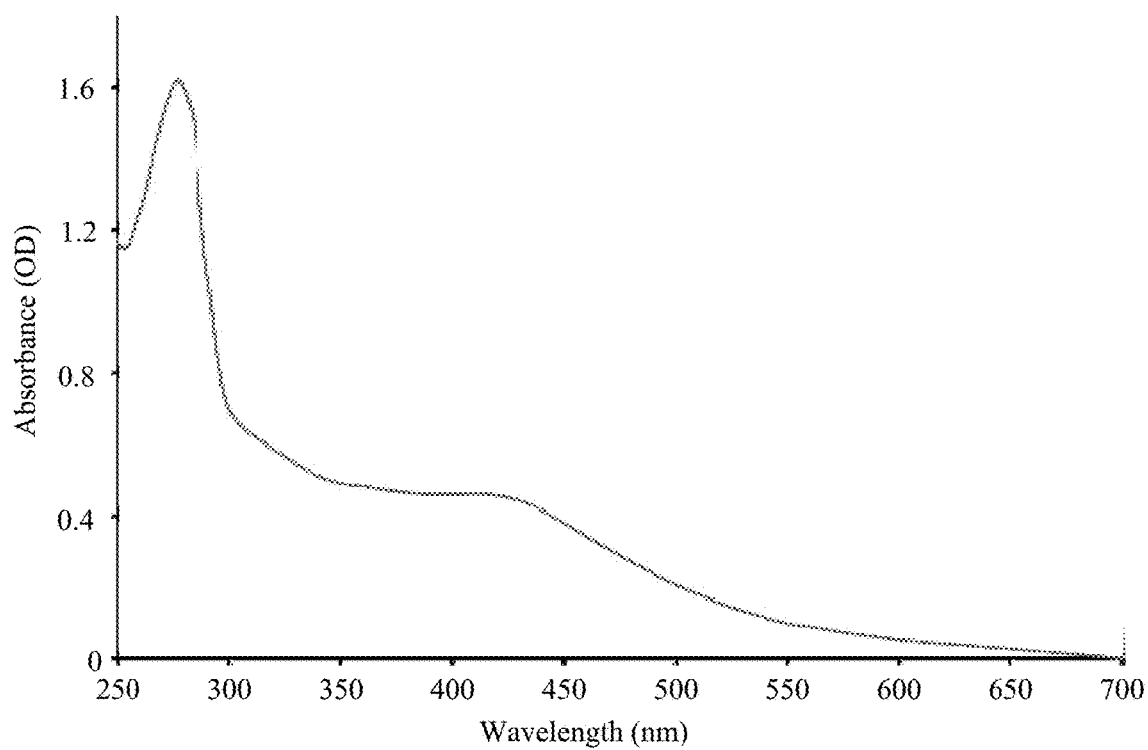
(FIG. 1C) UV-visible spectrum of anaerobically reconstituted YydG.

Radical SAM enzymes are an emerging family of enzymes catalyzing a large diversity of protein and peptide modifications such as oxidation, unusual methyl transfer reaction or thioether bond formation. They have emerged as major players for the biosynthesis of the so called RiPPs (Ribosomally synthesized and post-translationally modified peptides) being involved in chemically challenging reactions, that no other enzymes are able to perform. To investigate the biological role and the catalytic function of the putative radical SAM enzyme YydG, the inventors overexpressed the protein in *E. coli* and assayed its activity against the YydF peptide. The purified protein (FIG. 1B) had the distinctive spectroscopic properties of radical SAM enzyme with charge transfer absorption band at 320 and 420 nm (FIG. 1C). Based on a [4Fe-4S]$^{2+}$ cluster molar extinction coefficient of $\epsilon_{410}$~15,000 M$^{-1}$ cm$^{-1}$, the enzyme appears to possess one to two [4Fe-4S] centers after anaerobic reconstitution (FIG. 1C).

Figure 1G:
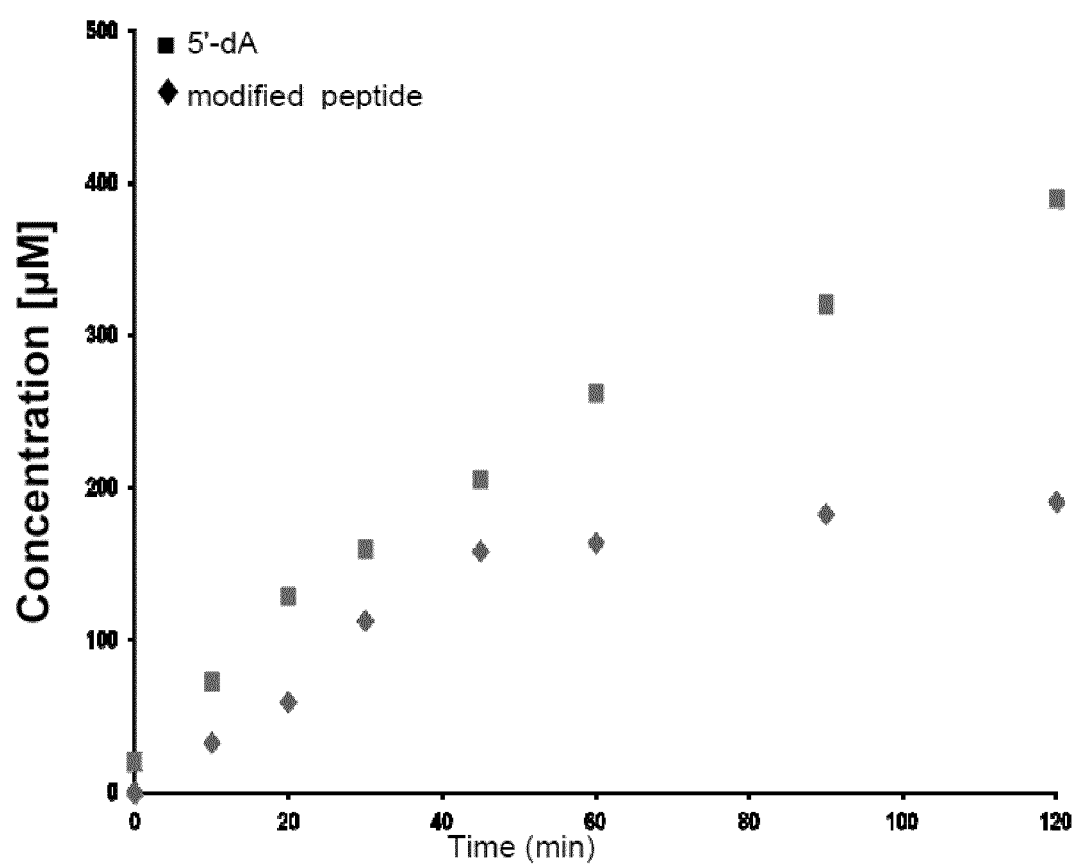
(FIG. 1G) Time course for the production of 5'-dA (■ and modified peptides (♦) quantified by reverse phase HPLC and monitored by UV-visible detection (280 nm). YydG (100 μM) was incubated under anaerobic conditions with sodium dithionite (2 mM) in the presence of 1 mM of substrate $YydF_{18-49}$.
Figure 1H:
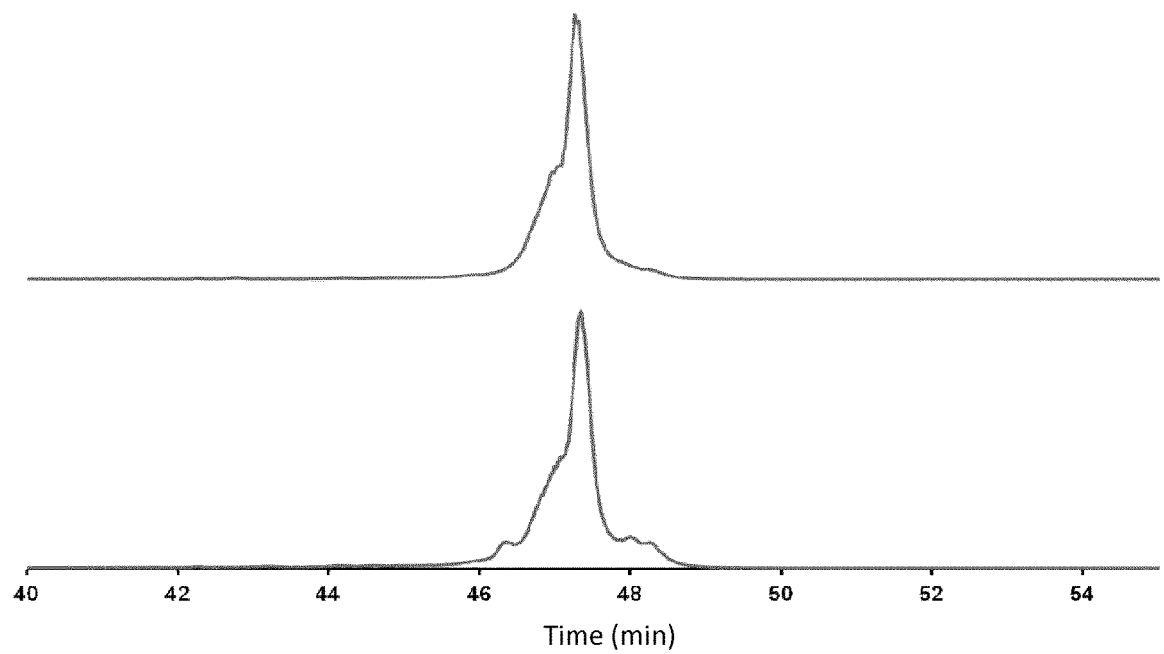
(FIG. 1H & I) HPLC analysis of YydG incubated with (FIG. 1H) YydF or (FIG. 1I) a truncated version of YydF18-49. YydG, after anaerobic reconstitution, was incubated under anaerobic conditions in the presence of DTT (6 mM) and SAM (1 mM) with or without sodium dithionite (2 mM).
Figure 1I:
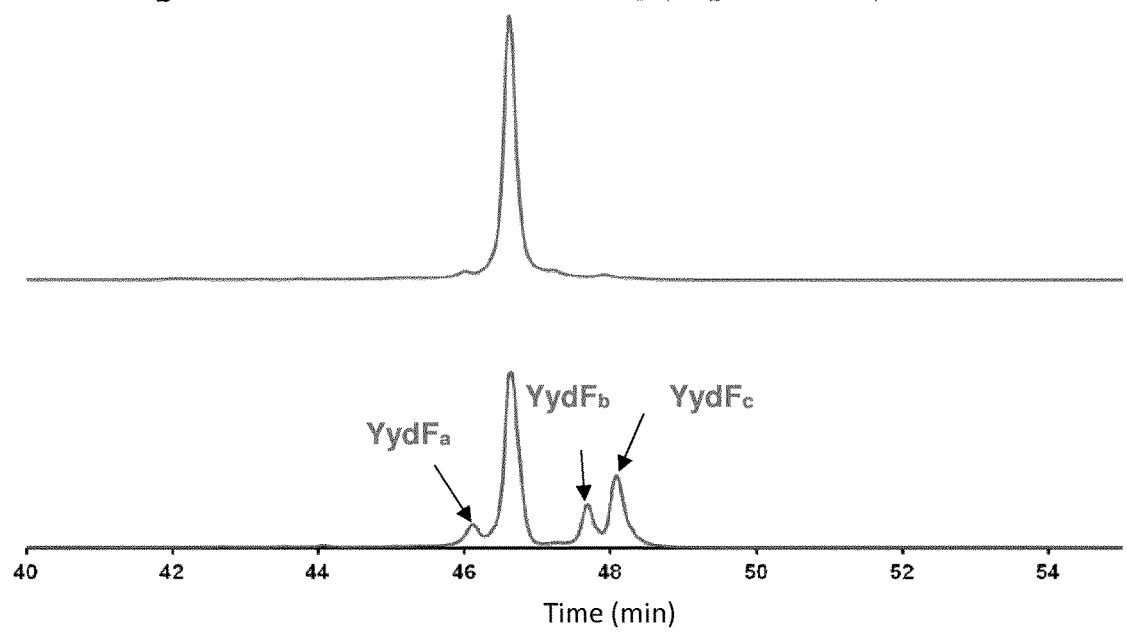
FIG. 1. Purification, spectroscopic analysis and activity of YydG.
(FIG. 1D) Multiple alignments of close YydF homologs found in particular in *B. subtilis* and *Staphylococci* species.
(FIG. 1E) HPLC analysis of SAM cleavage (257 nm) and (FIG. 1F) peptides produced in reaction (280 nm) after 4 hours incubation under anaerobic conditions in the presence or the absence of sodium dithionite (2 mM).

Genome mining revealed that yydF and yydG are also present in several Gram-positive pathogens such as *Enterococcus faecalis* and several *Streptococci* and *Staphylococci* including *S. agalactiae* and *S. epidermidis*. Sequence alignment of the YydF homologs indicated a putative leader-sequence located in the N-terminus part and a highly conserved motif from the residue 17 to the end of the peptide (FIG. 1D). The inventors assayed the reconstituted enzyme either with the full-length YydF peptide or a truncated form, encompassing the conserved amino acid residues from position 18 to 49 that we called YydF$_{18-49}$. As shown (FIG. 1E), under anaerobic and reducing conditions, YydG produced the expected 5'-deoxyadenosine (5'-dA; eluting at 12.3 min) resulting from the S-adenosyl-L-methionine (SAM) homolytic cleavage and also three peptide derivatives: YydF$_a$, YydF$_b$ & YydF$_c$ eluting at 46, 47.6 & 48 min (FIGS. 1E, F, G and H). The formation of the three peptides was strictly dependent of the presence of sodium dithionite as one-electron donor and similar products were obtained using YydF or YydF$_{18-49}$ (FIGS. 1F, G and H). Kinetic analysis of the reaction showed that YydG produced one mole of 5'-dA per mole of modified product and catalyzed several turnovers under in vitro conditions, although uncoupled SAM cleavage occurred as the reaction proceed (FIG. 1G). These results demonstrated that, in vitro, YydG used SAM to modify YydF through a radical-based mechanism. Since YydF$_{18-49}$ proved to be a better substrate and was easier to characterize, we decided to use it to identify the modification catalyzed by YydG.

Figure 2A:
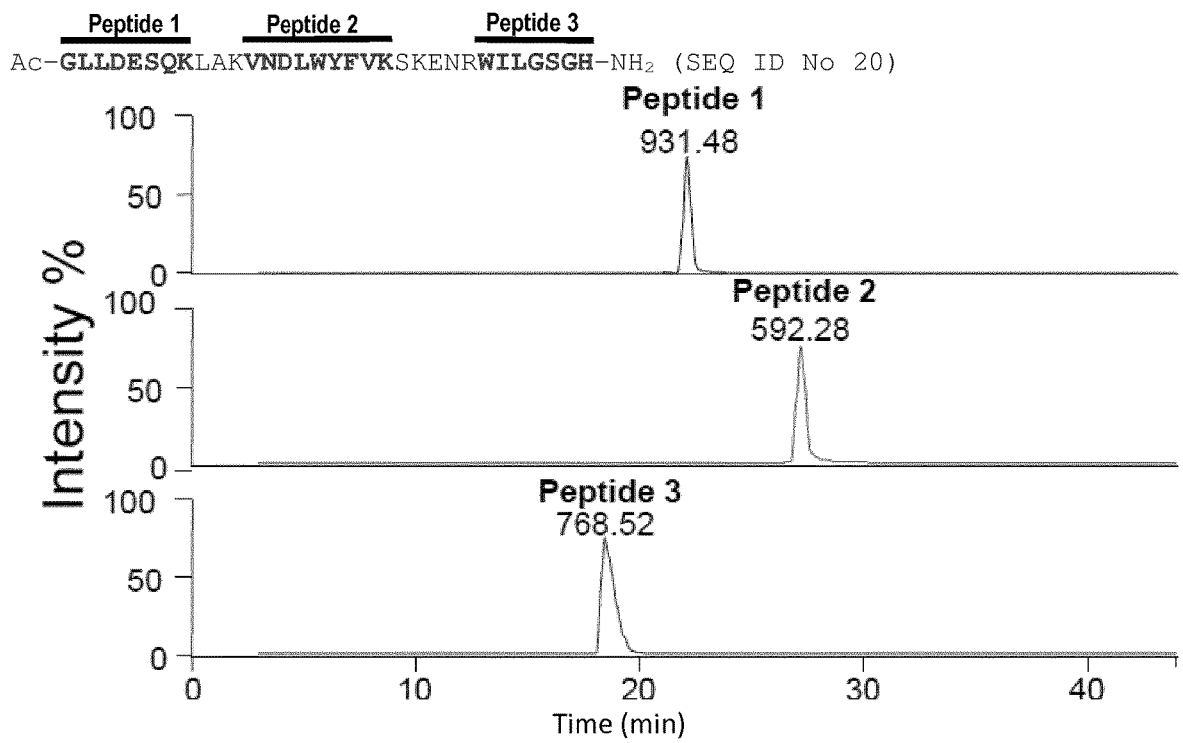
FIG. 2—YydG catalyzes H-atom transfer to the peptide backbone. Tryptic peptide mapping and LC-MS analysis of (FIG. 2A) $YydF_{18-49}$ or (FIG. 2B) $YydF_{18-49}$ after incubation with YydG. Numbers indicate the m/z value for each peptide. Sequence in bold indicates the relevant peptide identified by LC-MS (i.e. Peptide 1: NH$_2$-GLLDESQK, [M+H]$^+$= 931.48; Peptide 2: VNDLWYF [M+2H]$^{2+}$= 592.31; Peptide 3: WILGSGH-Ac, [M+H]$^+$=768.41).
(FIG. 2C) LC-MS analysis of the peptide $YydF_{18-49}$ after incubation with YydG in deuterated buffer.
(FIG. 2D) Tryptic peptide mapping and LC-MS analysis of $YydF_{18-49}$ after incubation with YydG in deuterated buffer.
Figure 2B:
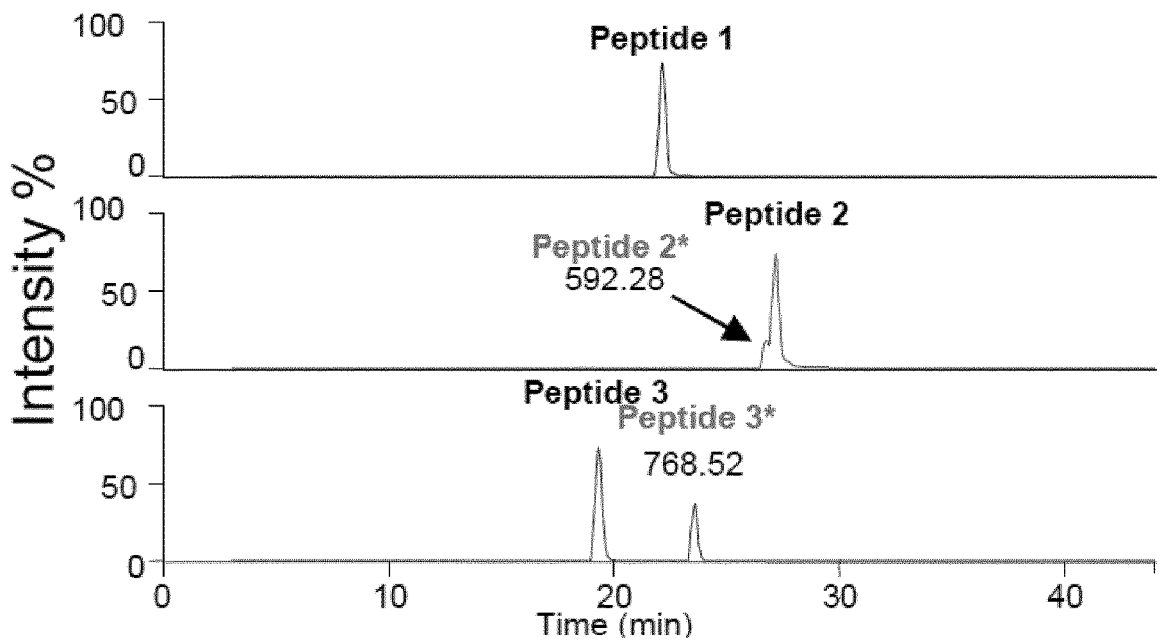

Mass spectrometry inspection of the three peptides formed revealed no mass difference compared with the substrate (YydF$_{18-49}$[M+3H]$^+$=1258.92). This was in contrast with all known rSAM enzymes catalyzing peptide or protein post-translational modifications such as such as cross-linking, oxidation or methylation (7, 9, 14-16). Tryptic peptide mapping of the substrate gave three peptides (Peptide 1 [M+H]$^+$=931.48, Peptide 2 [M+H]$^{2+}$=592.31 and Peptide 3: [M+H]$^+$=768.41) eluting at 22, 27 and 19.2 min) as shown on FIG. 2A. Comparison with the enzymatically modified peptide showed the appearance of two new peptides (i.e. Peptide 2* and Peptide 3*) having the same molecular weight as Peptide 2 & 3 but eluting at 26.5 and 23.5 min, respectively (FIG. 2B). This result supported that YydG had introduced two modifications one located internally (in Peptide 2) and one in the C-terminus end of peptide (in Peptide 3). In all the experiments performed, YydFc was the main product. Tryptic peptide mapping revealed that essential the C-terminus end of the peptide was modified since the Peptide 3*/Peptide 3 ratio was 5 times larger than the Peptide 2*/Peptide 2 ratio (FIG. 2B) indicating that YydG had some preferred sites.

Figure 2C:
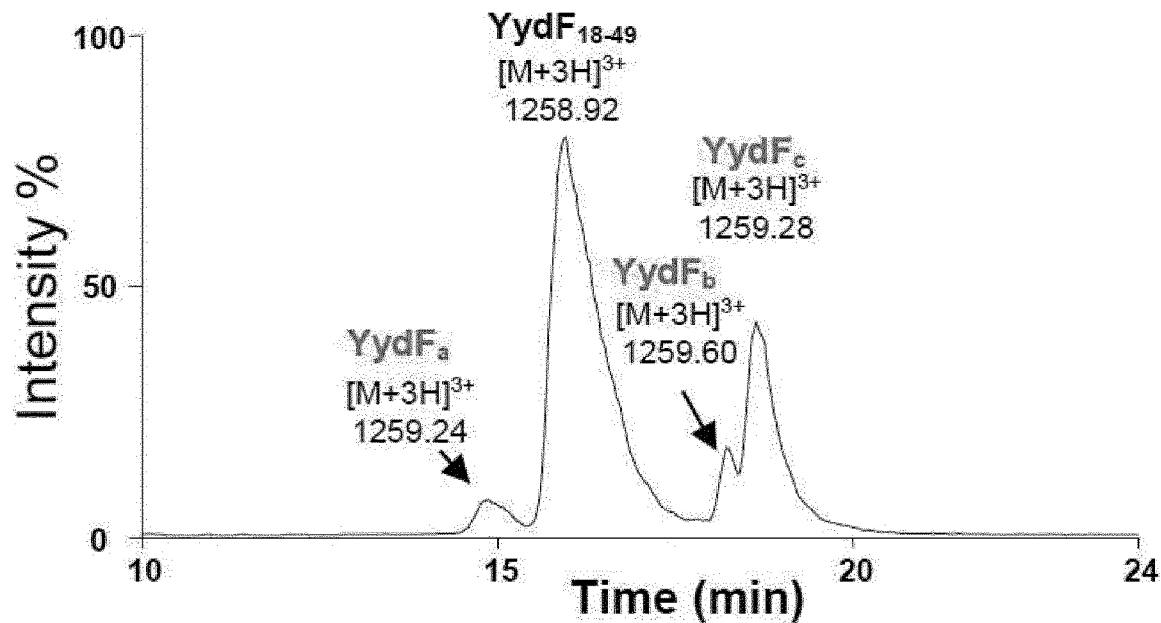
Figure 2D:
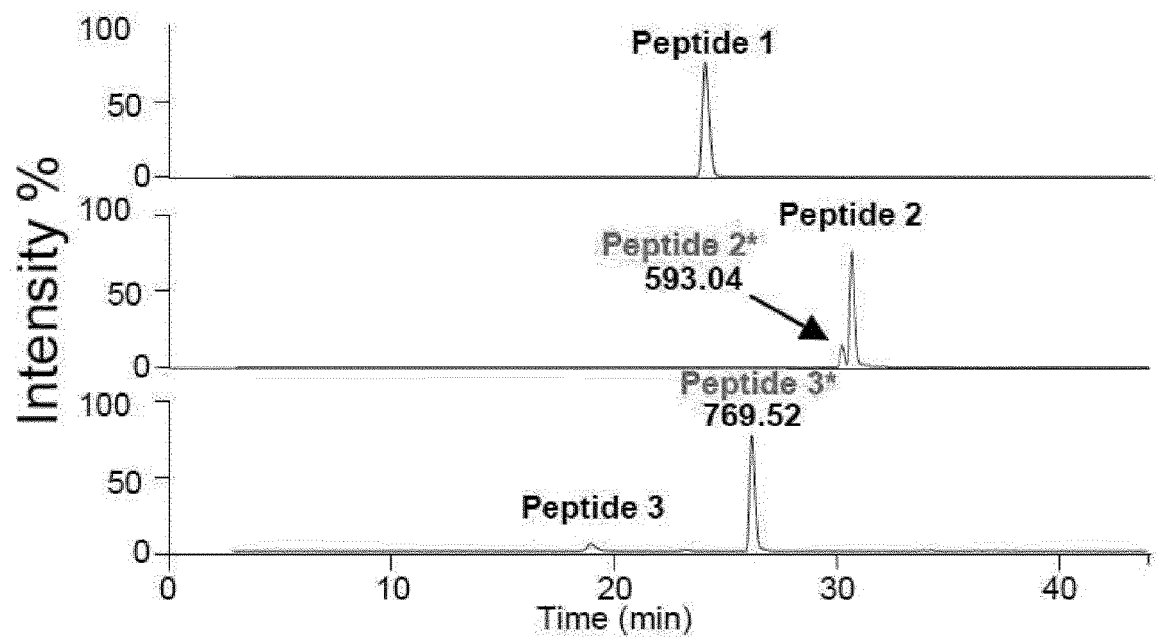

To identify the nature and location of the modifications catalyzed by YydG, the inventors repeated the reaction in >90% deuterated buffer since rSAM enzymes are known to abstract and sometimes exchange, H-atoms during catalysis. In deuterated buffer, YydG produced a similar product pattern with YydFc being always the most abundant product (FIG. 2C). Interestingly, LC-MS analysis of the reaction showed that under these conditions, YydF$_a$ and YydF$_c$ had a molecular weight of $[M+3H]^{3+}=1259.24$ and YydF$_b$ a molecular weight of $[M+3H]^{3+}=1259.6$. This corresponded to one and two Dalton units more than the substrate, YydF$_{18-49}$($[M+3H]^{3+}=1258.92$), unambiguously demonstrating that one deuterium atom was incorporated into YydF$_a$, YydF$_c$ and two deuterium atoms in YydF$_b$, respectively. Tryptic peptide mapping of the reaction allowed to localize deuterium incorporation exclusively in the Peptide 2* and Peptide 3* whose molecular masses shifted from one Dalton unit (i.e. $[M+2H]^{2+}=593.04$ and $[M+2H]^+=769.52$) (FIG. 2D). LC-MS/MS fragmentation of these two peptides demonstrated deuterium incorporation on Val$_{36}$ in Peptide 2* (as shown by the characteristic ions $y_1$, $y_2+1$ and $b_7$, $b_8+1$) and on Ile$_{44}$ in Peptide 3* (as shown by identification of the ions $y_5$ and $y_6+1$). Altogether these results demonstrated that YydG catalyzes the replacement of two peptide H-atoms by two solvent exchangeable H-atoms.

Figure 3A:
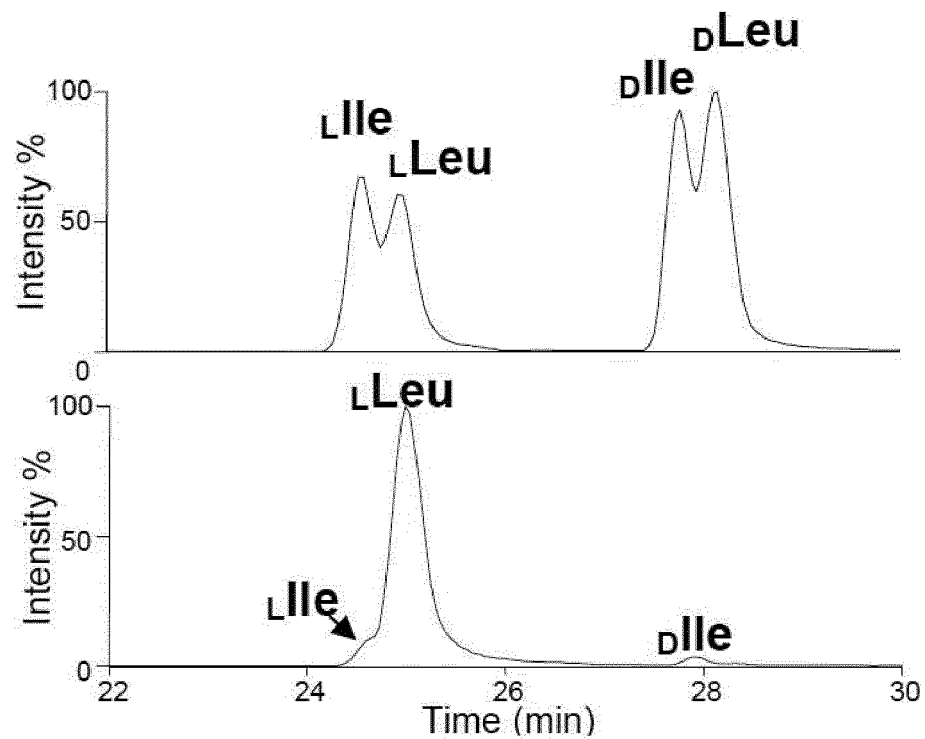
FIG. 3—YydG catalyzes amino acid epimerization. LC-MS/MS analysis of a (FIG. 3A) L-Ile/D-allo-Ile and (FIG. 3B) L-/D-Val (upper traces) compared with the amino acids obtained after incubation of $YydF_{18-49}$ with the rSAM enzyme YydG in deuterated buffer (lower traces). The amino acids were derivatized by N-α-(2,4-dinitro-5-fluorophenyl)-L-valinamide (L-FDVA) and detected by LC-MS as FDVA-derivatives.
Figure 3B:
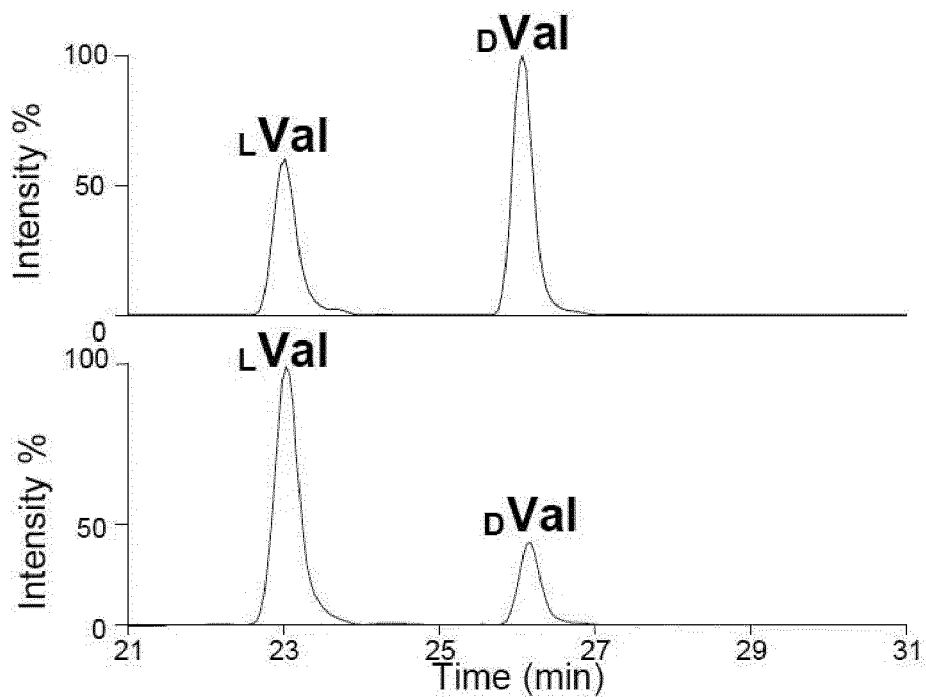

To determine the nature of the modification, the inventors performed acid hydrolysis of the peptide and analyzed its amino acid content, after derivatization with N-α-(2,4-dinitro-5-fluorophenyl)-L-valinamide (L-FDVA), by LC-MS. The YydF$_{18-49}$ peptide contains two Val and one Ile residues but five Leu residues which not only have the same molecular weight than Ile but also eluted at similar retention times. Optimized LC-MS/MS conditions allowed, as shown on FIG. 3A, the separation and characterization of L-Ile and L-Leu but also of their D-configured counterparts (D-allo-Ile and D-Leu). Analysis of the enzymatically modified peptides clearly showed that, in addition of the identification of L-Ile and L-Leu, another product eluting at 27.7 min was formed corresponding to D-allo-Ile. Similarly, the analyses of Val residues (FIG. 3B) showed the presence not only of L-Val but also of D-Val eluting at 26 min.

The inventors hence established that YydG is a radical SAM epimerase, the first one shown to be active in vitro on a peptide backbone. The enzyme catalyzed the epimerization of up to ~35% of the Ile and ~10% of Val residues. Consistent with this conclusion, when one derivatized the amino acids epimerized by incubating YydG in deuterated buffer, their mass analyses revealed a +1 Da increment (FIG. 3C&D), consistent with the analyses performed on the intact peptide and their tryptic derivatives (FIG. 2C&D).

To definitely assert their identity as D-configured amino acids, the inventors synthesized a YydF$_{18-49}$ variant peptide containing one D-Val and one D-allo-Ile in positions 36 and 44, respectively. The tryptic peptide mapping and the amino acid profile of this synthetic peptide perfectly reproduced the ones of the enzymatically modified peptide (data not shown).

Based on these analyses, the inventors were able to assign YydF$_a$ as a peptide containing a D-Val in position 36, YydF$_c$ as peptide containing a D-allo-Ile in position 44 and YydF$_b$ as peptide containing a D-Val and a D-allo-Ile in positions in positions 36 & 44, respectively. Hence YydG, produced a mixture of peptides containing either a single or double modified amino acids, with Ile$_{44}$ being the favored substrate (FIG. 2C).

During the epimerization reaction performed in deuterium buffer, if the inventors have established that a solvent-exchangeable H-atom is incorporated into the peptide backbone, the 5'-dA produced contained no significant labeling as shown by LC-M analysis. These results and the kinetic analysis on FIG. 1G are consistent with YydG producing one 5'-dA radical (5'-dA•) to abstract the C$_α$ H-atom of Val$_{36}$ or Ile$_{44}$ with the concomitant formation of one mole of 5'-dA.

The last questions which remained to be solved, was the origin of exchangeable H-atom introduced during catalysis. Indeed, the carbon-centered radical was unlikely to interact with a buffer component as such highly reactive species must be kept sealed in the enzyme active site. The inventors favored a protein amino acid residue as H-atom donor and radical quencher required to terminate the reaction. Close inspection of the YydG sequence pointed out that, in addition to the three cysteine residues from the radical SAM motif, only six cysteines were present in the sequence (FIG. 4A). Interestingly, two cysteine residues (i.e. Cys22 and Cys223) were adjacent to another cysteine residue, one of which being inside the predicted loop containing the rSAM [4Fe-4S] center. The organization of the five other cysteine residues in the C-terminus end of the protein was reminiscent of motifs involved in the coordination of additional [4Fe-4S] centers in rSAM enzymes. To probe their function, the inventors substituted the three cysteine residues of the CxxxCxxC radical SAM motif, Cys22, Cys222 or Cys223 by alanine residues. The four designed mutants (i.e. A3, C22A, C222A and C223A) were successfully purified although the C222A mutant proved to be recalcitrant to purification and produced partly as a truncated form (FIG. 4B). Spectroscopic analysis showed that, based on its UV-visible spectrum, the AxxxAxxA mutant contained ~1 [4Fe-4S] center while the amount of [4Fe-4S] center was two-times higher in the C22A and the C223A mutants (FIG. 4C). Importantly, the aerobically purified AxxxAxxA mutant already contained high amounts of iron-sulfur center demonstrating that the presence of [4Fe-4S] center in this mutant was independent of the anaerobic reconstitution. The UV-visible spectra of C22A and C223A mutants perfectly superimpose with the wild-type enzyme (FIG. 1B), supporting the fact that YydG likely contains two [4Fe-4S] centers. The C222A mutant appeared to contain no iron-sulfur center, even after anaerobic reconstitution (FIG. 4C). The C222A absorption maximum was shifted toward 250 nm indicating that the protein was likely miss-folded, as it has been repeatedly reported when cysteine residues involved in [4Fe-4S] coordination are mutated in iron-suflur enzymes including rSAM enzymes. It is thus likely than Cys222, is involved in coordination of the second [4Fe-4S] center present in YydG.

Figure 4D:
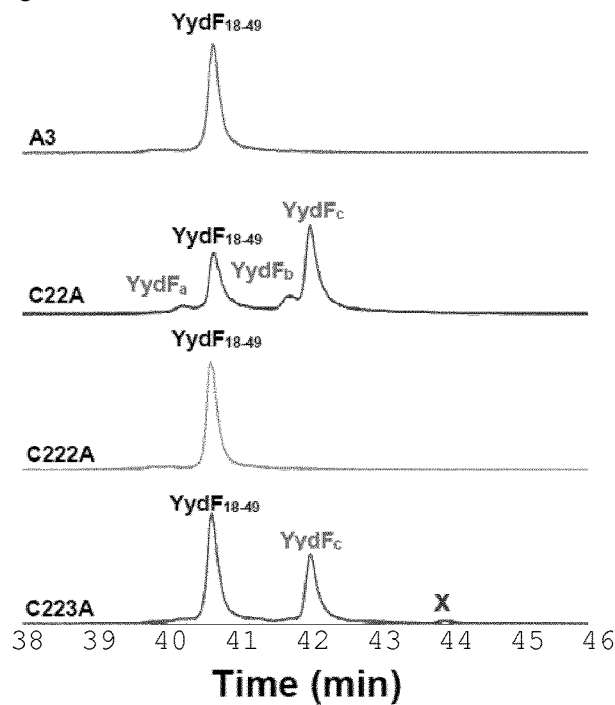
(FIG. 4D) HPLC analysis of the reaction after incubation of YydF18-49 and the four mutants in the presence of SAM (1 mM) and sodium dithionite.
Figure 4E:
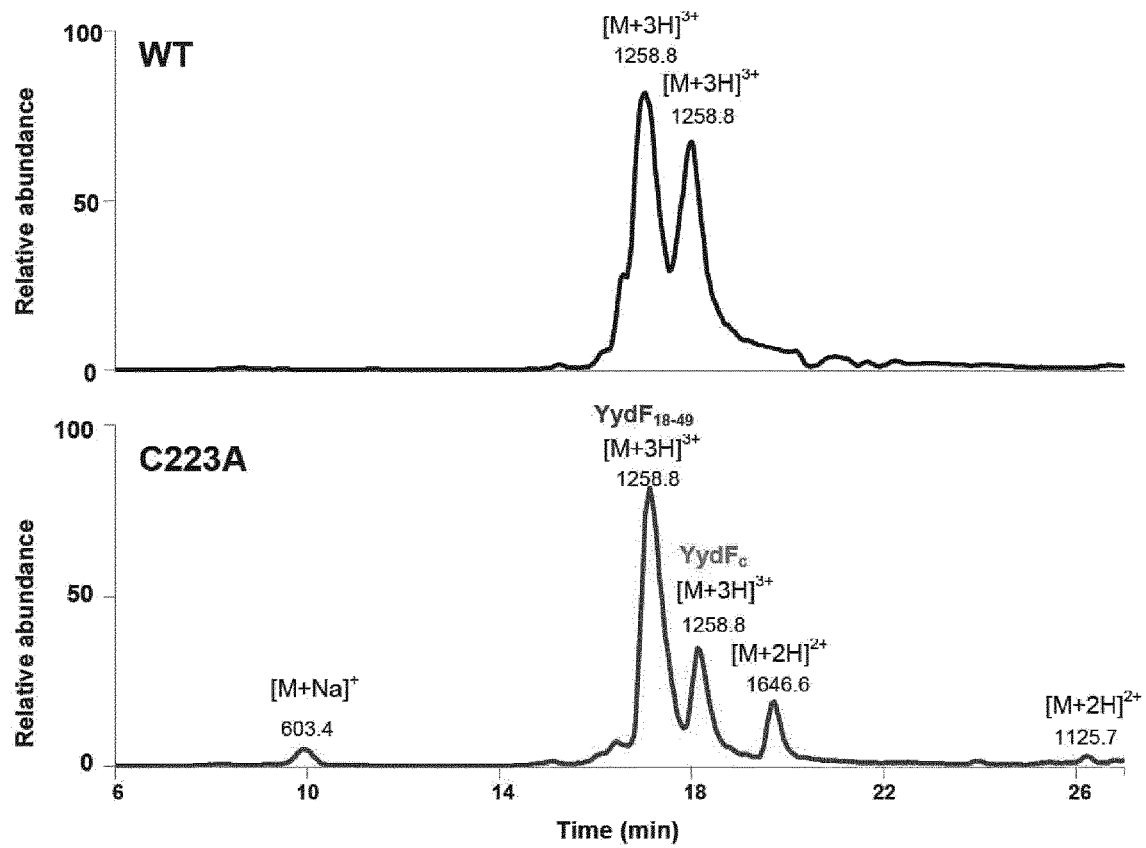
(FIG. 4E) LC-MS analysis of the peptides produced by the C223A mutant and their corresponding masses and sequences.

The activity of all the mutants was assayed with the YydF$_{18-49}$ substrate (FIG. 4D). As expected, the A3 mutant was unable to convert the peptide substrate and to cleave SAM. The C222A mutant was also totally impaired for enzyme activity. In contrasts, the C22A mutation did not affect the activity of the enzyme and the three epimerized peptides were produced (i.e. YydF$_a$, YydF$_b$ and YydF$_c$). The C223A mutation did not either prevent the epimerization activity. However, this enzyme variant produced other peptide derivatives eluting at 10 min, 19.8min and 26 min (FIG. 4E). High-resolution mass spectrometry showed these peptides to have a mass shift of −30.005 Da or −1.032 Da, compared to predicted hydrolytic products. They all contained at their C-terminus or N-terminus ends a truncated Val$_{36}$ or Ile$_{44}$, the targets of the YydG enzyme (FIG. 4E). Their structure was determined as: Ac-GLL-DESQKLAKVNDLWYFVKSKENRWI* (SEQ ID No 53) (peptide G$_{18}$-I$_{44}$*, $[M+2H]^{2+}=1646.3834$); and I*LGSGH—NH$_2$ (SEQ ID No 55) (peptide G$_{18}$-I$_{44}$*, $[M+Na]^+=603.2851$). The truncation was identified as the loss of the amino acid carboxylic or amino group, resulting from the rupture of either the C$_α$—N or the C$_α$—CO bonds, and the addition of an oxygen-atom on the amino acid C$_α$-atom. These results are reminiscent of the substrate fragmentation obtained with another member of the rSAM enzyme family, the pyruvate formate lyase activase, when the reaction was exposed to molecular oxygen. They also definitively established that YydG generates a carbon-centered radical on the C$_α$-atom of Val$_{36}$ and Ile$_{44}$ and that Cys223 plays a critical role for the termination of the reaction.

In light of the previous work of the inventors on another rSAM enzyme, the spore photoproduct lyase (SP lyase), the inventors interpreted the role of Cys223 as the critical H-atom donor. Indeed, while investigating a mutant of the SP lyase, they have shown that in the absence of a suitable protein H-atom donor, the substrate radical intermediate can react with adventitious radical scavengers leading to the formation of various adducts. Here, the stabilized $C_\alpha$ radical, in the absence of the thiol group of Cys223, is free to react with molecular oxygen leading to these unique peptidyl backbone breakages.

Figure 5A:
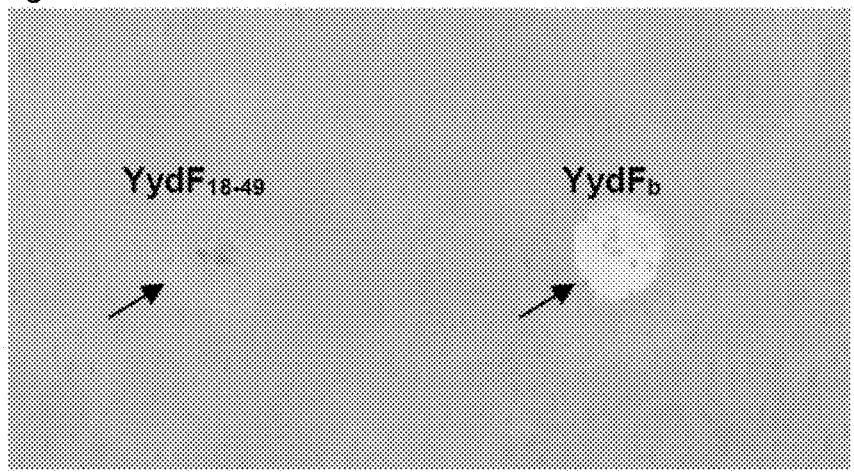
(FIG. 5A) Plate growth inhibition assay of *B. subtilis* in the presence of $YydF_{18-49}$ or the epimerized product YydFb.
Figure 5B:
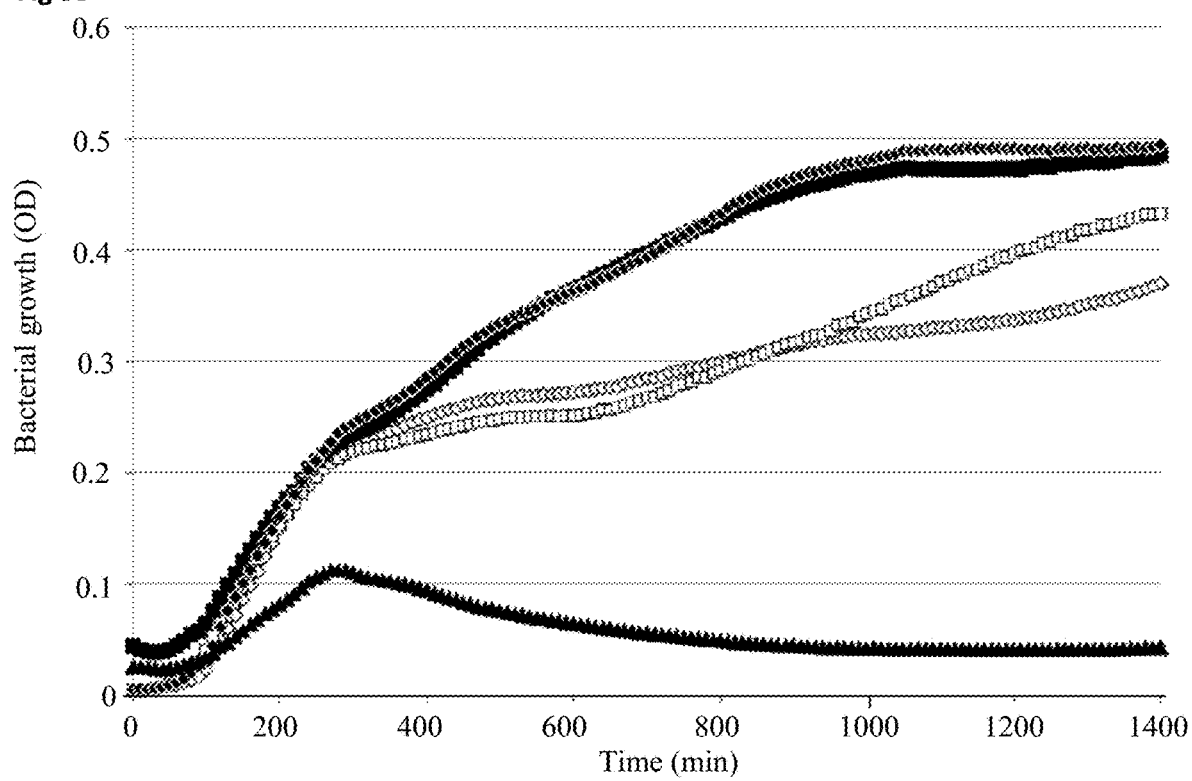
(FIG. 5B) Growth of *Bacillus subtilis* in LB medium in the absence of peptide (□) or in the presence of the $YydF_{18-49}$ peptide with a free C-terminus: Ac-GLLDESQKLAKVNDLWYFVK-SKENRWILGSGH (SEQ ID No 20) containing either no modification (■), a D-allo-Ile (♦), a D-Val (◊) or two-epimerized residues: Ac-GLLDESQKLAKVNDLWYF{d-V}KSKENRW{d-I}LGSGH (SEQ ID No 20) (▲). The OD values are the means of 3 independent cultures.

Finally, since the YydFGHIJ operon (FIG. 1A) was shown to activate the Lia system in *B. subtilis,* the inventors assayed the activity of the $YydF_{18-49}$ peptide before and after enzyme reaction on various bacterial strains. They evidenced strong inhibition growth of *B. subtilis* with either the enzymatically epimerized peptide or the synthetic peptide containing $D-Val_{36}$ and $D-allo-Ile_{44}$. In contrast, the unmodified $YydF_{18-49}$ peptide was devoid of activity (FIG. 5A). Similarly, in liquid medium, only the epimerized peptide proved to be active as a strong and persistent inhibition could be measured (FIG. 5B). Further studies will be required to decipher the molecular basis of this inhibition but according to the inventors' knowledge, it is the first time that a naturally epimerized peptide proved to be the active form of a regulatory or antimicrobial bacterial peptide.

The present study demonstrates that peptides containing D-amino acids, called herein Epipeptides, are much more common than previously anticipated in living organisms including the common laboratory bacterium *Bacillus subtilis* but also many pathogenic species such as *Streptococcus agalactiae, Enterococcus faecails* or *Staphylococcus epidermidis*. Unexpectedly, the inventors demonstrated here that D-amino acids appear not only to provide resistance to proteases but are directly involved in bacterial response.

Example 2

A gene, yydF, was proposed in the literature to encode a peptide produced by *Bacillus subtilis* (SEQ ID No 1). However no proof of its actual synthesis or of any post-translational modification has been reported.

Figure 7:
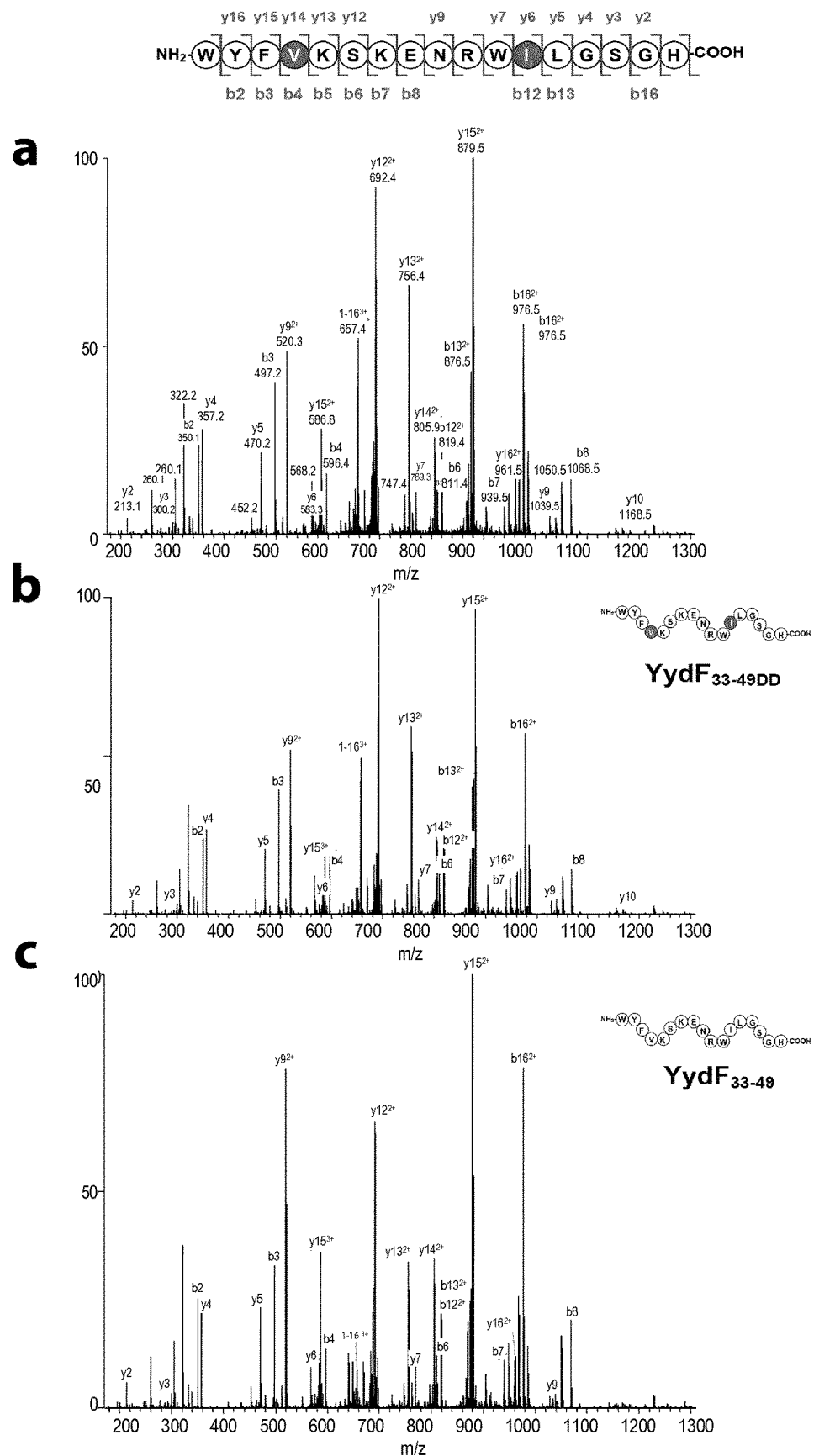
FIG. 7—Mass spectrometry analysis of the YydF peptide isolated from *B. subtilis* and named $YydF_{33-49}$. LC-MS/MS analysis of (a) the peptide secreted by *B. subtilis*, (b) synthetic $YydF_{33-49DD}$ peptide containing two D-amino acids residues and (c) synthetic $YydF_{33-49}$ peptide. Relevant ions are indicated. Tables 1 for full assignment. In the peptide sequence, amino acids with a D-configuration are indicated in grey.

After growth of *B. subtilis* in a synthetic medium (Buffer solution 5× (Na2HPO4: 17 g ; KH2PO4: 7.5 g, NaCl: 1.25 g; NH4Cl: 2.5 g in 500 mL); Trace element solution: $MnCl_2$: 20 mg; $ZnCl_2$: 34 mg; $CuCl_2$: 8.6mg; $CoCl_2$: 12mg; $Na_2MoO_4$ : 12 mg; in 200 mL), the inventors successfully purified a peptide, originating from YydF and encompassing residues 33 to 49 (FIG. 7), as established by mass spectrometry analysis (Table 1). The sequence of the isolated peptide was determined to be (SEQ ID No 61):

Trp Tyr Phe Val Lys Ser Lys Glu Asn Arg Trp Ile
1               5                   10

Leu Gly Ser Gly His
          15

SEQ ID No 61: Sequence of the peptide $YydF_{33\_49}$

In addition, the inventors determined that the peptide $YydF_{33-49}$, produced by *B. subtilis* contained 2 epimerized residues (i.e. D-amino acids) located in position 36 (Val) and 44 (Ile). The peptide was thus called $YydF_{-33-49DD}$. Previous work from the inventors (Example 1) has established that the epimerized residues are the result of the conversion of L-amino acid residues by a unique radical SAM enzyme, YydG, which targets the amino acids $C_\alpha$-atom. Currently, no such short peptides, containing discreet epimerization, are known to be produced by bacteria.

Because the operon YydFGHIJ, was shown to induce the two component system LiaRS, which among other stimuli, sense the bacterial cell-wall integrity, the inventors searched for a putative bacterial growth inhibition triggered by various YydF peptide derivatives. Initial tests were performed with a peptide encompassing residues 18-49 ($YydF_{18-49}$, SEQ ID No 20).

As shown (FIG. 5B), only in the presence of the peptide $YydF_{18-49DD}$ containing two epimerized residues: $Val_{36}$ and $Ile_{44}$ (numbering according to SEQ ID No 61), the inventors monitored bacterial growth inhibition. The presence of one epimerized residues or the absence of epimerized residues did not significantly impacted bacterial growth. This demonstrated, for the first time, that a short peptide with epimerized residues can inhibit bacterial growth.

Figure 8:
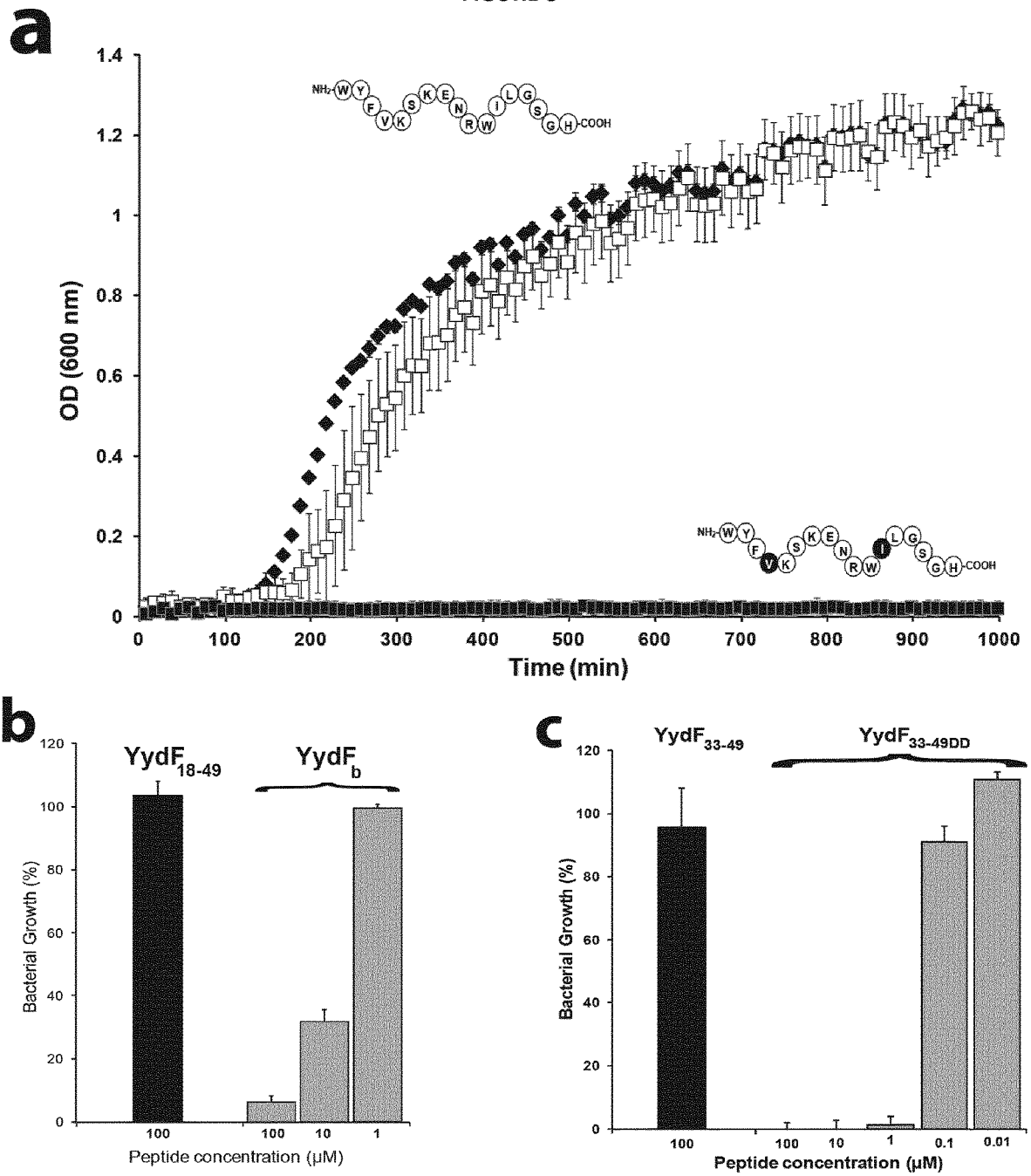
FIG. 8—(A) Growth of *B. subtilis* in liquid LB medium in the presence of $YydF_{33-49}$ or $YydF_{33-49}$DD. *B. subtilis* was grown in LB medium alone (♦), in the presence of $YydF_{33-49}$ (□) (SEQ ID NO: 76, top) or $YydF_{33-49DD}$ (■) (SEQ ID NO: 75, bottom). Each measurement is the mean of three growth experiments with the SD indicated. The epimerized residues are in black. (b) Growth ratio of *B. subtilis* in presence of $YydF_{18-49}$ (100 μM) or $YydF_{18-49DD}$ (100, 10 or 1 μM). Ratios were determined by comparison with growth in the absence of peptide. (c) Growth ratio of *B. subtilis* in presence of $YydF_{33-49}$ or $YydF_{33-49DD}$ (100, 10, 1, 0.1 or 0.01 μM). Ratios were determined by comparison with bacterial growth in the absence of peptide.
Figure 9:
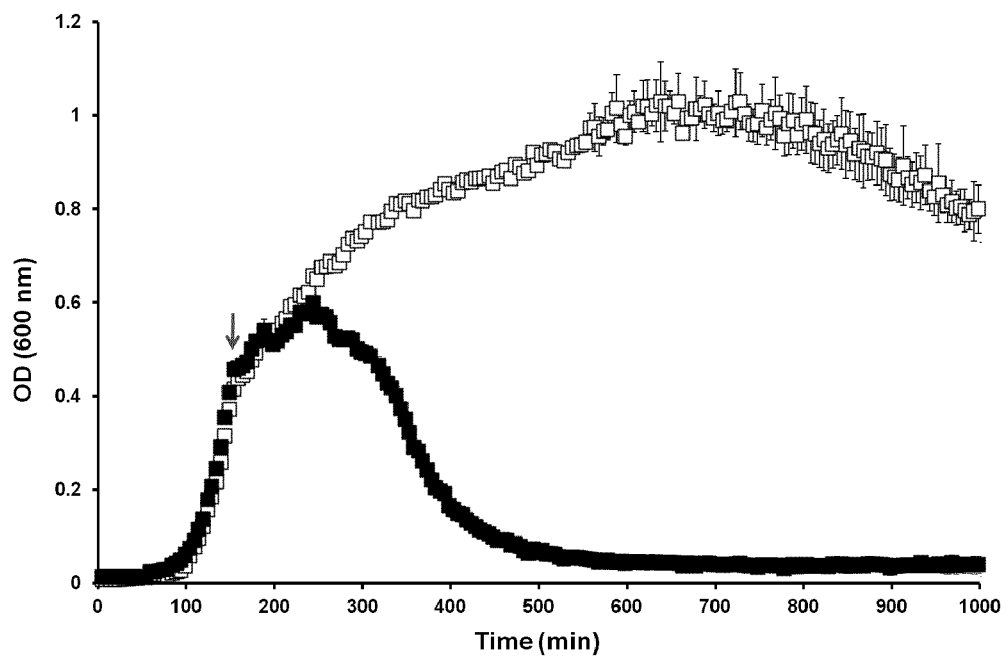
FIG. 9—Growth of *B. subtilis* in liquid LB medium in the presence of $YydF_{18-49}$ (□) or after addition (arrow) of the $YydF_{18-49DD}$ (■) after 3 hours of growth. Each measurement is the mean of three growth experiments with the SD indicated.

Having established that the presence of two key epimerized residues is critical for the inhibitory properties, the inventors synthesized two peptides corresponding to the sequence of the peptide produced by *B. subtilis* (SEQ ID No 61). These two peptides contained either only L-amino acid residues ($YydF_{33-49}$) or the two critical epimerized residues: $D-Val_{36}$ and $D-Ile_{44}$ ($YydF_{33-49DD}$). Only the $YydF_{33-49DD}$ peptide proved to inhibit bacterial growth (FIG. 8*a*). This novel peptide proved to be 100 times more potent than the $YydF_{1849}DD$ peptide previously assayed (FIG. 8*b*&*c*) with a MIC <1 µM. In addition, the inventors showed that these peptides do not only inhibit bacterial growth but they also induce bacterial cell death. Indeed, if after initial growth for 3 hours, the $YydF_{18-49}$ peptide is added at mid-exponential phase (FIG. 9), a clear slow down followed by a decrease of the cell density was measured.

Interestingly, homologs of the YydF peptides are predicted in the genome of several Gram-positive bacteria such as: *Salinibacillus aidingensis, Bacillus coagulans, Paenibacillus* sp and several pathogenic species such as: *Enterococcus faecalis, Enterococcus caccae, Streptococcus agalactiae, Staphylococcus pseudintermedius, Staphylococcus equorum, Staphylococcus condimenti* and *Staphylococcus epidermidis* (FIG. 1D, FIG. 6).

In order to determine if these peptides are bioactive, the inventors synthesized a library of peptides based on the sequences identified in the genomes of *Streptococcus* and *Staphylococcus* species. They hypothesized that these peptides should contain the same post-translational modifications as the ones identified in *B. subtilis,* which means a processed peptide of 17 amino acid residues with two D-amino acids in the positions 4 and 12 (SEQ ID Nos 62-65). The epimerized residues are in bold.

```
Streptococcus agalactiae Peptide-SA1
                                    (SEQ ID No 62)
WYFVRSSKNRWVAGSAH Streptococcus agalactiae Peptide-5A2
                                    (SEQ ID No 63)
WYFVRNSKNRWVAGSAH Staphylococcus equorum Peptide-SE
                                    (SEQ ID No 64)
WYFVKSKQNRWVVGSGH Staphylococcus pseudintermedius Peptide-SP
                                    (SEQ ID No 65)
WYFVKSQSNRWIVGSGH
```

In addition, the inventors also synthesized three unnatural peptides derived from the *B. subtilis* $YydF_{33\_49}$ sequence (SEQ ID No 61) but for which the two epimerized residues (i.e. $Val_{36}$ and $Ile_{44}$) were both substituted by Val, Ile or Ala residues, $YydF_{33\_49VV}$, $YydF_{33\_49II}$ and $YydF_{33\_49AA}$, respectively (SEQ ID Nos 66-68). The epimerized residues are in bold.

YYd F$_{33\_49AA}$     WYFAKSKENRWALGSGH     (SEQ ID No 66)

Yyd F$_{33\_49VV}$     WYFVKSKENRWVLGSGH     (SEQ ID No 67)

Yyd F$_{33\_49II}$     WYFIKSKENRWILGSGH     (SEQ ID No 68)

Figure 10:
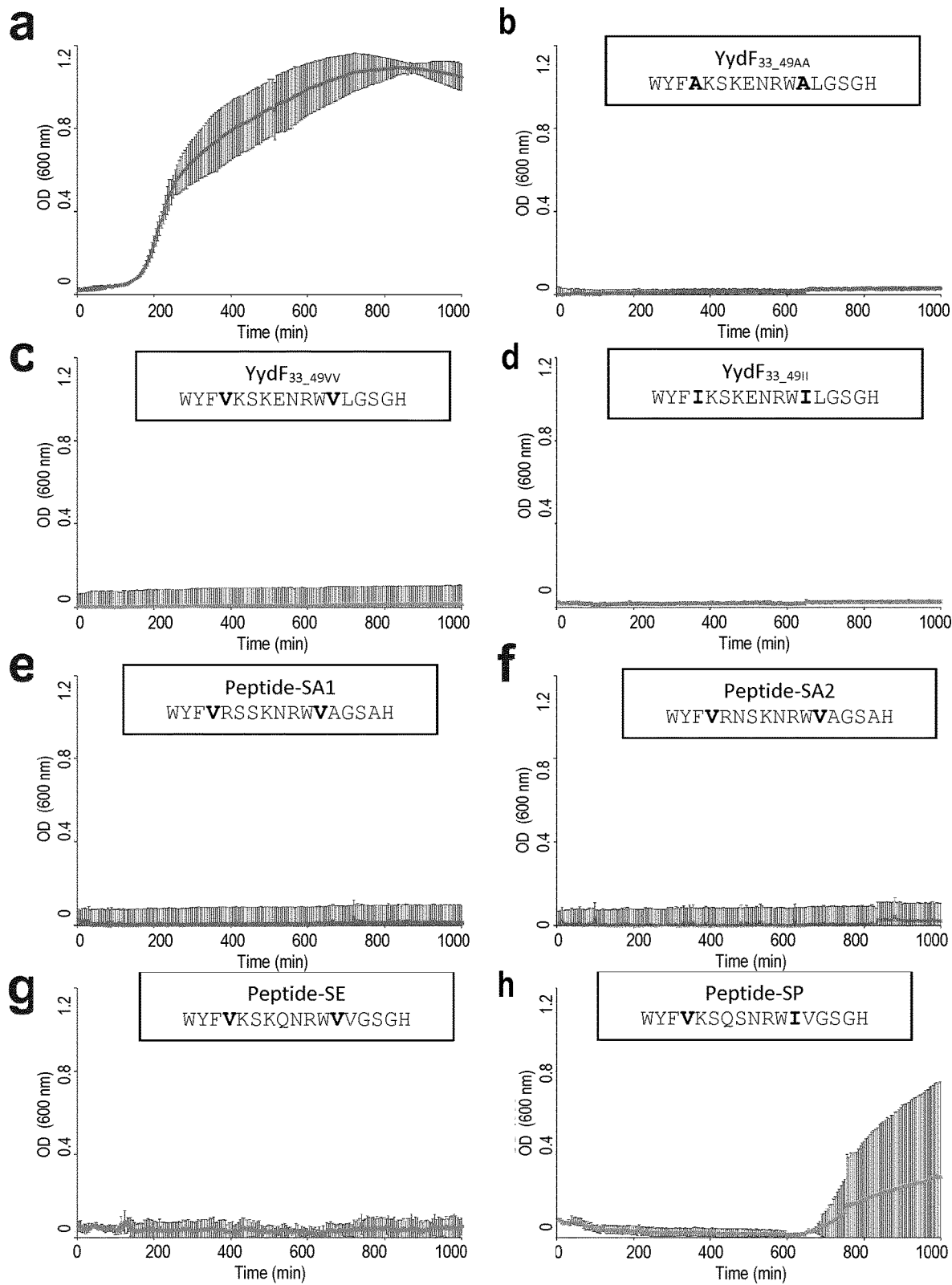
FIG. 10—Growth of *B. subtilis* in liquid LB medium in the presence of $YydF_{33-48}$ (a), $YydF_{33\_49AA}$ (b) (SEQ ID NO: 66), $YydF_{33\_49vv}$ (c) (SEQ ID NO: 67), $YydF_{33\_49II}$ (d) (SEQ ID NO: 68), Peptide-SA1 (e) (SEQ ID NO: 62), Peptide-SA2 (f) (SEQ ID NO: 63), Peptide-SE (g) (SEQ ID NO: 64) or Peptide-SP (h) (SEQ ID NO: 65) at 100 μM. In bold, epimerized residues.
Figure 11:
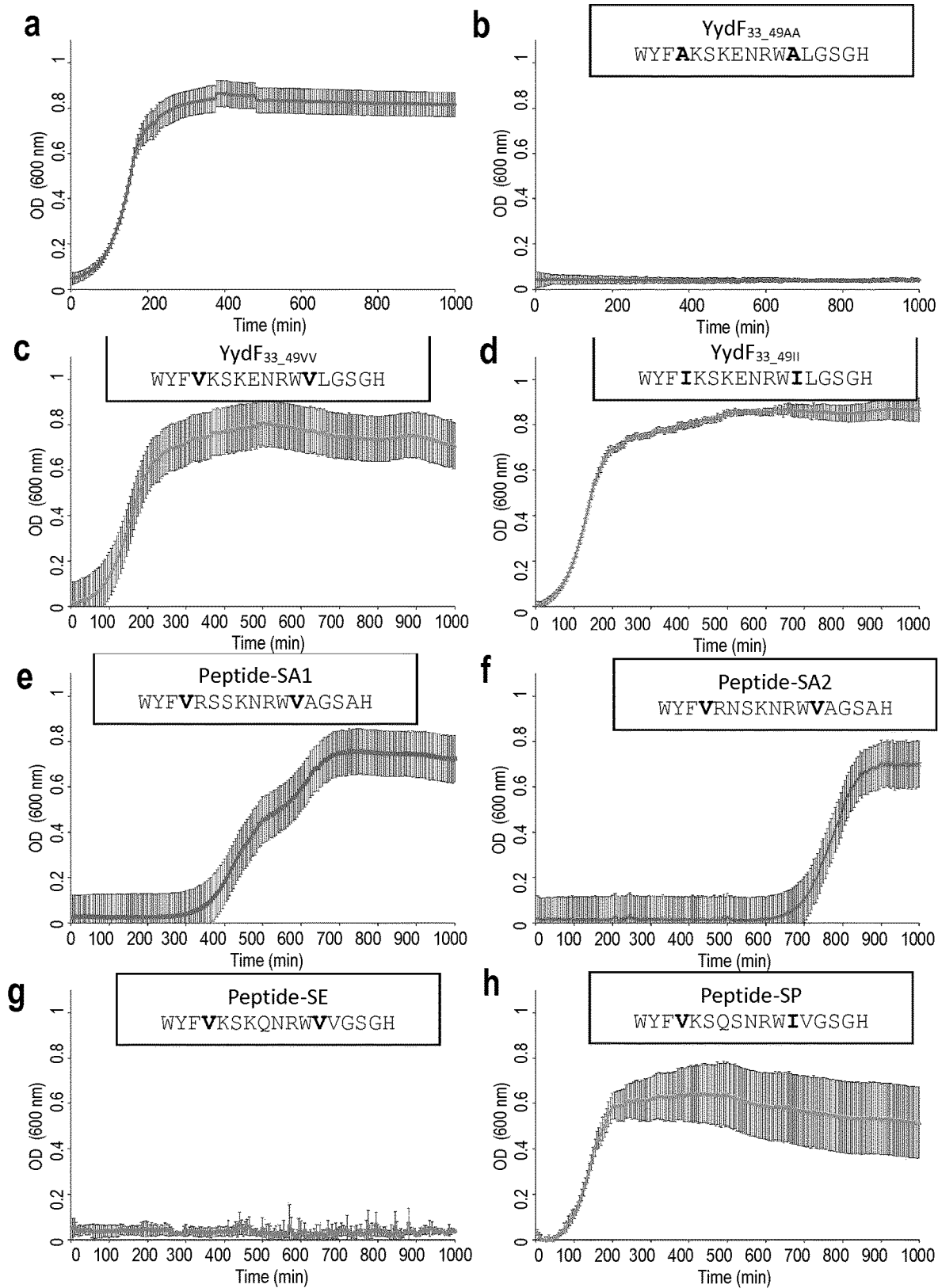
FIG. 11—Growth of *Enterococcus faecalis* in liquid BHI medium in the presence of $YydF_{33-49}$ (a), $YydF_{33\_49AA}$ (b) (SEQ ID NO: 66), $YydF_{33\_49VV}$ (c) (SEQ ID NO: 67), $YydF_{33\_49II}$ (d) (SEQ ID NO: 68), Peptide-SA1 (e) (SEQ ID NO: 62), Peptide-SA2 (f) (SEQ ID NO: 63), Peptide-SE (g) (SEQ ID NO: 64) or Peptide-SP (h) (SEQ ID NO: 65) at 100 μM. In bold, epimerized residues.
Figure 12:
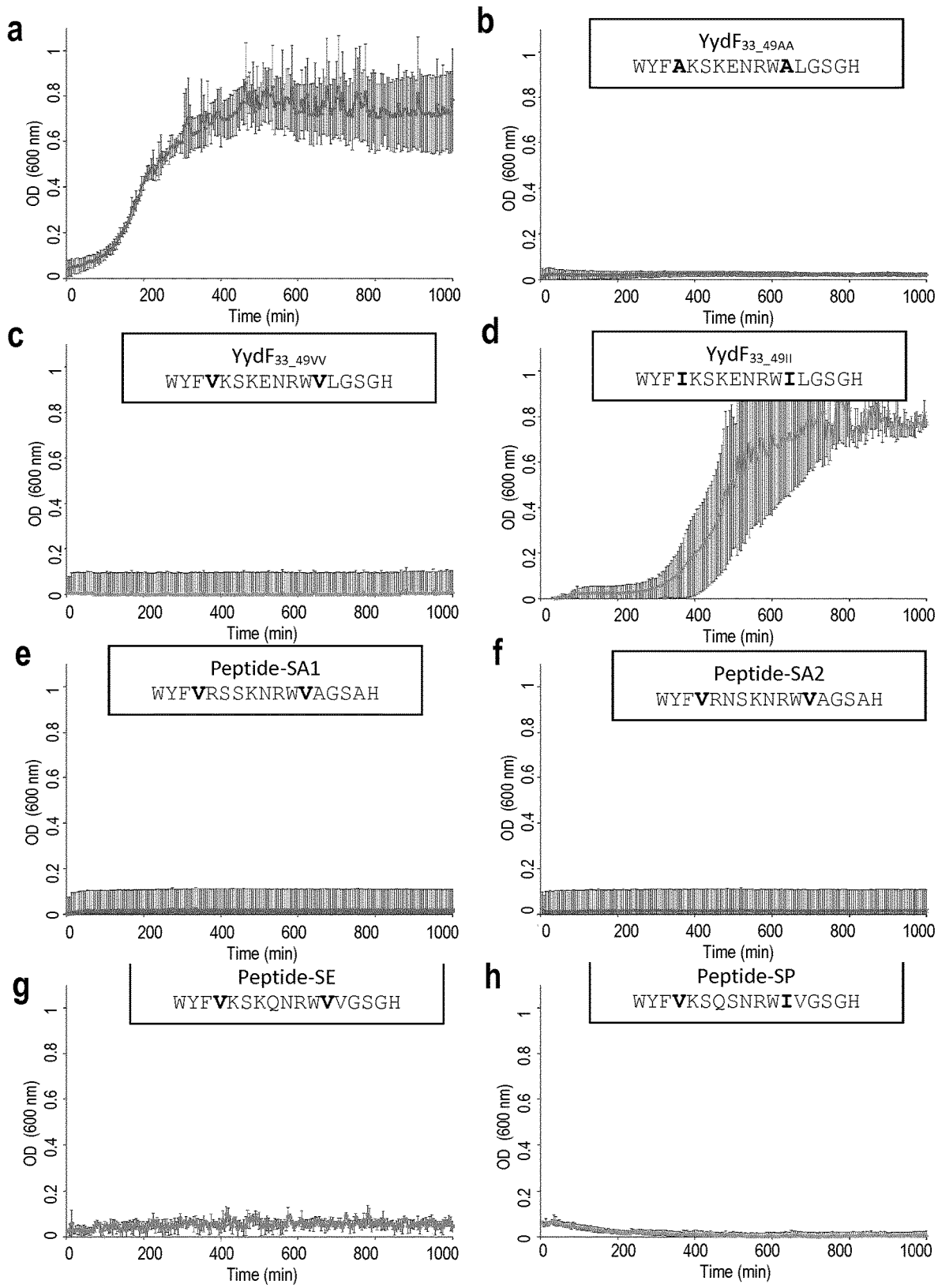
FIG. 12—Growth of *Streptococcus agalactiae* in liquid BHI medium in the presence of YydF$_{33-49}$ (a), YydF$_{33\_49AA}$ (b) (SEQ ID NO: 66), YydF$_{33\_49VV}$ (c) (SEQ ID NO: 67), YydF$_{33\_49II}$ (d) (SEQ ID NO: 68), Peptide-SA1 (e) (SEQ Ill NO: 62), Peptide-SA2 (f) (SEQ ID NO: 63), Peptide-SE (g) (SEQ ID NO: 64) or Peptide-SP (h) (SEQ ID NO: 65) at 100 µM. In bold, epimerized residues.

These 7 peptides (SEQ ID Nos 62-68) were assayed against *B. subtilis* and the two representative Gram-positive pathogens: *S. agalactiae* and *E. faecalis*. As shown, all peptides were effective against *B. subtilis* including the peptides with unnatural sequences (FIG. 10). *E. faecalis* growth was significantly delayed with Peptide-SA1 & Peptide-SA2 and growth totally inhibited with Peptide-SE and the unnatural peptide YydF$_{33\_49}$AA (FIG. 11). *S. agalactiae* was inhibited by YydF$_{33\_49DD}$ and the derivatives YydF$_{33\_49AA}$ and YydF$_{33\_49VV}$ but not by YydF$_{33\_49II}$ (FIG. 12). The peptides: Peptide-SA1, Peptide-SA2, Peptide-SE and Peptide-SP were all inhibitors.

The inventors thus demonstrated that short peptides containing two D-amino acid residues are a novel class of inhibitory peptides able to inhibit the growth of several Gram-positive bacteria including relevant pathogens. They are efficient whether added at the beginning or after bacterial growth at mid-exponential phase. Finally, some discreet modifications in the sequence are able to tune the inhibition properties and the specificities at the genera and species level of these peptides allowing the development of targeted antibiotics. In addition, based on the framework of 17 amino acids and the conserved location of two D-amino acids (in position 4 and 12) downstream to aromatic residues (W or Y), the inventors also demonstrated that it is possible to design peptides with unnatural sequences that proved to be effective against all the Gram-positive bacteria assayed.

The bioactive peptides proved to have sequence identity varying from 100 to 58.8% relative to the original YydF$_{33-49}$ sequence which means at least 7 amino acid residues could be changed without altering their global inhibition properties. It is thus possible to engineer these peptides in an unprecedented manner to target specific bacterial genera and tune their biological properties.

with 6mL of buffer A containing desthiobiotine (0.6 mg/mL) further concentrated with Amicon concentrator (Millipore) with a molecular cut-off of 10 kDa.

Enzyme Reconstitution

YydG was reconstituted under anaerobic conditions in a Bactron IV anaerobic chamber. The protein was mixed with 3 mM of DTT at 12° C. during 15 minutes then Na$_2$S and (NH$_4$)$_2$Fe(SO$_4$)$_2$ were added and the solution was incubated at 12° C. during 4 h.

Enzyme Assays

YydG was incubated with 3 mM DTT, 1 mM SAM and 1 mM peptide substrate unless otherwise indicated. Incubations were performed at 25° C. under strict anaerobic conditions and 10 µL aliquots sampled overtime.

HPLC Analysis

HPLC analysis was performed on an Agilent 1200 series infinity equipped with a reversed phase column (LiChroSphere 100 RP-18e 5 µm) (Merck Millipore). A gradient from solvent A (H$_2$O, 0.1% TFA) to B (80% CH$_3$CN, 19.9% H$_2$O, 0.1% TFA) was applied as follow: 0-1 min: 100% A/0% B; 1-45 min: a linear gradient with 1% of solvent B per minute at a flow rate of 1 ml.min$^{-1}$. Detection was made at 257 & 278 nm with a diode array detector and by fluorescence (excitation at 278 nm and emission at 350 nm).

Liquid Chromatography—Mass Spectrometry/Mass Spectrometry Analysis

High resolution liquid chromatography—mass spectrometry/mass spectrometry analysis were performed using an LTQ-Orbitrap Discovery mass spectrometer (ThermoFisher) with a nanoelectrospray ion source and an Ultimate 3000 LC system (Dionex). A LTQ mass spectrometer (ThermoFisher) with a nanoelectrospray ion source was used for routine analysis. Peptide analysis was performed on a nanocolumn Pepmap 100 C18 (0.075 by 15 cm, 100 Å, 3 µm).

Inhibition Assay on Solid Medium

An overnight culture of the bacterial strain to be assayed was freshly inoculated to sterile BHI liquid medium. After 4 hours of bacterial growth at 37° C., the medium was diluted to 1/1000 and inoculated into a soft agarose medium pre-heated at 42° C. The agarose medium containing bacteria was overlaid on a previously jellified sterile BHI

| # Percent Identity | Matrix # | | | | | | |
|---|---|---|---|---|---|---|---|
| 1: Peptide-SA1 | 100.00 | 94.12 | 64.71 | 70.59 | 58.82 | 58.82 | 64.71 | 70.59 |
| 2: Peptide-SA2 | 94.12 | 100.00 | 58.82 | 64.71 | 52.94 | 52.94 | 58.82 | 64.71 |
| 3: Peptide-SP | 64.71 | 58.82 | 100.00 | 82.35 | 70.59 | 76.47 | 82.35 | 76.47 |
| 4: Peptide-SE | 70.59 | 64.71 | 82.35 | 100.00 | 76.47 | 76.47 | 82.35 | 88.24 |
| 5: YydF33_49AA | 58.82 | 52.94 | 70.59 | 76.47 | 100.00 | 88.24 | 88.24 | 88.24 |
| 6: YydF33_49II | 58.82 | 52.94 | 76.47 | 76.47 | 88.24 | 100.00 | 94.12 | 88.24 |
| 7: YydF33_49DD | 64.71 | 58.82 | 82.35 | 82.35 | 88.24 | 94.12 | 100.00 | 94.12 |
| 8: YydF33_49VV | 70.59 | 64.71 | 76.47 | 88.24 | 88.24 | 88.24 | 94.12 | 100.00 |

Materials and Methods

YydG Expression

The yydG genes was synthesized (Life Technologies) and cloned into a pASK plasmid. The plasmid was expressed in *E. coli* BL21 (DE3) star (Life Technologies) and protein expression was performed in LB medium containing ampicillin (100 µg.mL-1). After overnight growth at 21° C., the cells were collected and disrupted by ultra-sonication in buffer A (Tris 50 mM, KCl 300 mM, Glycerol 10% pH 7.5). The bacterial suspension was centrifuged at 45,000×g for 1.5 hours and the protein supernatant was loaded onto a Streptactin high capacity (IBA GmbH) column previously equilibrated with buffer A. The YydG protein was eluted agarose layer. 200 µg of peptide was spotted onto the plate and bacterial growth proceeded at 37° C.

Inhibition Assay on Liquid Medium

An overnight culture of the bacterial strain to be assayed was freshly inoculated to sterile LB liquid medium. After 4 hours of bacterial growth at 37° C., the medium was diluted to 1/10,000 and inoculated into sterile liquid LB or BHI medium. Peptide solution was added (1/100) to a final concentration ranging from 0.01 to 100 µM and OD at 600 nm was recorded continuously using a Tecan microplate reader (Infinite® 200 PRO series).

TABLE 1

Mass fragments for peptide YydF$_{33-49}$ isolated from *B. subtilis*

| Sequence | | b+ | b++ | y+ | y++ | |
|---|---|---|---|---|---|---|
| W | 1 | 187.08718 | 94.04753 | 2107.08779 | 1054.04783 | 17 |
| Y | 2 | 350.15051 | 175.57919 | 1921.00848 | 961.00818 | 16 |
| F | 3 | 497.21892 | 249.11340 | 1757.94515 | 879.47651 | 15 |
| V | 4 | 596.28734 | 298.64760 | 1610.87674 | 805.94230 | 14 |
| K | 5 | 724.38230 | 362.69509 | 1511.80833 | 756.40810 | 13 |
| S | 6 | 811.41433 | 406.21110 | 1383.71336 | 692.36062 | 12 |
| K | 7 | 939.50929 | 470.25858 | 1296.68133 | 648.84460 | 11 |
| E | 8 | 1068.55188 | 534.77988 | 1168.58637 | 584.79712 | 10 |
| N | 9 | 1182.59481 | 591.80134 | 1039.54378 | 520.27582 | 9 |
| R | 10 | 1338.69592 | 669.85190 | 925.50035 | 463.25436 | 8 |
| W | 11 | 1524.77523 | 762.89155 | 769.39974 | 385.20381 | 7 |
| I | 12 | 1637.85930 | 819.43358 | 583.32043 | 292.16415 | 6 |
| L | 13 | 1750.94336 | 875.97562 | 470.23637 | 235.62212 | 5 |
| G | 14 | 1807.96483 | 904.48635 | 357.15230 | 179.08009 | 4 |
| S | 15 | 1894.99685 | 948.00236 | 300.13084 | 150.56935 | 3 |
| G | 16 | 1952.01832 | 976.51309 | 213.09881 | 107.05334 | 2 |
| H | 17 | 2089.07723 | 1045.04255 | 156.07735 | 78.54261 | 1 |

(M) 2106.07997
$(M + H)^+$ 2107.08779
$(M + 2H)^{2+}$ 1054.04783
$(M + 3H)^{3+}$ 703.03451
$(M + 4H)^{4+}$ 527.52785

The invention claimed is:

1. A peptide 17 to 25 amino acids in length and in which the amino acids [V/I/A] in position 4 and 12 of the sequence as set forth in the following SEQ ID NOs have a D-configuration, wherein:
   a) the peptide contains SEQ ID NO: 66, 67, or 68;
   b) the peptide contains SEQ ID NO: 77;
   c) the peptide contains SEQ ID NO: 78;
   d) the peptide contains SEQ ID NO: 79; or
   e) the peptide contains SEQ ID NO: 73 and the peptide has at least one modification selected from the group consisting of N-acetylation, acylation, C-amidation, a (CH$_2$NH) reduced bond, a (NHCO) retro-inverso bond, a (CH$_2$-O) methylene-oxy bond, a (CH$_2$-S) thiomethylene bond, a (CH$_2$CH$_2$) carba bond, a (CO—CH$_2$) cetomethylene bond, a (CHOH—CH$_2$) hydroxyethylene bond, a (N—N) bound, a E-alcene bond and a —CH=CH-bond.

2. The peptide according to claim 1, wherein the peptide contains SEQ ID NO: 66.

3. The peptide according to claim 1, wherein the peptide contains SEQ ID NO: 67.

4. The peptide according to claim 1, wherein the peptide contains SEQ ID NO: 68.

5. The peptide according to claim 1, wherein the peptide contains SEQ ID NO: 77.

6. The peptide according to claim 1, wherein the peptide contains SEQ ID NO: 78.

7. The peptide according to claim 1, wherein the peptide contains SEQ ID NO: 79.

8. The peptide of claim 1, wherein the peptide is between 17 to 25 amino acids in length, has at least two D-configured amino acids and contains SEQ ID NO: 73, wherein the amino acids [V/I/A] in position 4 and 12 have a D-configuration and the peptide has at least one modification selected from the group consisting of N-acetylation, acylation, C-amidation, a ($CH_2NH$) reduced bond, a (NHCO) retro-inverso bond, a ($CH_2$-O) methylene-oxy bond, a ($CH_2$-S) thiomethylene bond, a ($CH_2CH_2$) carba bond, a (CO—$CH_2$) cetomethylene bond, a (CHOH—$CH_2$) hydroxyethylene bond, a (N—N) bound, a E-alcene bond and a —C=CH-bond.

9. A pharmaceutical or veterinary composition comprising the peptide according to claim 1.

10. A medical device or implant comprising a body having at least one surface coated with or including the peptide of claim 1.

11. A disinfectant or preservative composition comprising the peptide of claim 1.

\* \* \* \* \*

UNITED STATES PATENT AND TRADEMARK OFFICE
CERTIFICATE OF CORRECTION

PATENT NO. : 10,981,957 B2
APPLICATION NO. : 15/781153
DATED : April 20, 2021
INVENTOR(S) : Alhosna Benjdia, Alain Guillot and Olivier Berteau It is certified that error appears in the above-identified patent and that said Letters Patent is hereby corrected as shown below:

In the Specification

Column 6,
Line 58, "W-[V/I/A]-X4-G-S" should read --W-[I/V/A]-X4-G-S--.

Column 21,
Lines 53-54, "*corlsbergensis,*" should read --*carlsbergensis,*--.

Column 22,
Line 22, "*su/phureum,*" should read --*sulphureum,*--.

Column 26,
Line 49, "Riding," should read --Söding,--.

Column 28,
Line 30, "*B. subtilis*, (b)" should read --*B. subtilis* (SEQ ID NO: 74), (b)--.
Lines 31-32, "D-amino acids residues and" should read --D-amino acids residues (SEQ ID NO: 75) and--.
Line 32, "peptide. Relevant" should read --peptide (SEQ ID NO: 76). Relevant--.

Column 30,
Line 40, "(YydF$_{18-49}$[M+3H]$^+$=1258.92)." should read --(YydF$_{18-49}$[M+3H]$^{3+}$=1258.92).--.

Column 34,
Line 22, "YydF$_{1849}$DD" should read --YydF$_{18-49DD}$--.

Column 35,
Line 16, "YydF$_{33\_49}$AA" should read --YydF$_{33\_49AA}$--.

Signed and Sealed this
Second Day of November, 2021

Drew Hirshfeld
*Performing the Functions and Duties of the
Under Secretary of Commerce for Intellectual Property and
Director of the United States Patent and Trademark Office*

In the Claims

Column 115,
Lines 9-10, "a –C=CH-bond." should read --a –CH=CH-bond.--.